United States Patent [19]

Johnson et al.

[11] Patent Number: 5,238,832

[45] Date of Patent: Aug. 24, 1993

[54] ARYL ALIPHATIC ACIDS

[75] Inventors: Carl R. Johnson, Detroit; Gilles Gorins, Southfield; Kenneth V. Honn, Grosse Pointe Woods, all of Mich.; Lawrence J. Marnett, Brentwood, Tenn.

[73] Assignees: Board of Governors of Wayne State University, Detroit, Mich.; Vanderbilt University, Nashville, Tenn.

[21] Appl. No.: 894,952

[22] Filed: Jun. 8, 1992

[51] Int. Cl.$^5$ .................. C12N 9/00; A61K 31/19; C07C 321/20; C07C 59/64
[52] U.S. Cl. .................................. 435/183; 435/184; 435/963; 514/532; 514/570; 514/571; 560/9; 560/55; 562/426; 562/465
[58] Field of Search ............ 560/9, 55; 562/426, 562/465; 435/183, 184, 963; 514/532, 570, 571

[56] References Cited

PUBLICATIONS

*Cancer Res.*, vol. 47, pp. 6751–6762, (1987).
*Cancer Res.*, vol. 49, pp. 1029–1037, (1989).
*Advances in Prostaglandins, Thromboxane and Leukotriene Research*, vol. 19, Raven Press Ltd., New York, pp. 439–443, (1989).
Tamaru et al., *Organic Syntheses*, vol. 67, pp. 98–104, (1988).
Pasto, *Tetrahedron*, vol. 40, No. 15, pp. 2805–2827, (1984).
Elsevier et al., *J. Org. Chem.* vol. 54, pp. 3726–3730, (1989).
Gooding et al. *J. Org. Chem.* vol. 56, No. 3, pp. 1083–1088, (1991).
Burgess et al., *J. Am. Chem. Soc.*, vol. 113, No. 16, pp. 6129–6139, (1991).

*Primary Examiner*—José G. Dees
*Assistant Examiner*—Vera C. Clarke
*Attorney, Agent, or Firm*—Ian C. McLeod

[57] ABSTRACT

Novel aryl aliphatic acids or derivatives thereof of the general formula $$R-(C_x-C_y)-(C_mH_{2m})-G-C(R^1)_2-Ar-(C_nH_{2n})-COOR^2$$

are described which exhibit inhibiting activity against 12-lipoxygenase. The compounds are characterized by having a low level of toxicity. Also included are salts and esters of the aliphatic acids.

70 Claims, No Drawings

ARYL ALIPHATIC ACIDS

BACKGROUND OF THE INVENTION (1) Field of the Invention

SUMMARY: This invention relates to novel compounds having an inhibitory activity against 12-lipoxygenase.

More particularly, this invention is related to (1) aryl aliphatic acids or derivatives thereof having an inhibitory activity against 12-lipoxygenase, of the following general formula:

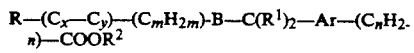

including the acid, pharmaceutically acceptable salts thereof and esters and (2) process for the preparation of them, and (3) 12-lipoxygenase inhibiting agents containing them as an active ingredient.

(2) Prior Art

Lipoxygenases are the enzymes related to the oxidative metabolic pathway of unsaturated fatty acids. 5-,8-, 11-, 12- and 15-Lipoxygenases are rather well characterized examples of these enzymes. A particular lipoxygenase oxidizes a particular position of arachidonic acid to produce a particular metabolite. For example, 5(X)-lipoxygenae produces 5-HETE (5(S)-5-hydroxyeicosa-6(E), 8(Z)-14(Z)-tetraenoic acid or LTs (so called leukotrienes) through 5-HPETE (5(S)-5-hydroperoxyeicosa-6(E), 8(Z), 11(Z), 14(Z)-tetraenoic acid). In spite of being found in mammalian tissue the role of 12-lipoxygenase is not well known.

12(S)-HETE (12(S)-hyroxyeicosa-5(Z), 8(Z), 10(E), 14(Z)-tetraenoic acid), a metabolite of arachidonic acid, is produced by 12-lipoxygenase and possesses a variety of biological characteristics, e.g. antagonism of LTB$_4$ and enhancement of the enzyme activity of 5-lipoxygenase. It is thought that 12-lipoxygenase is involved in inflammation and immunity. Further, it is also thought that lipoxygenases are closely related to ischemic heart diseases and ischemic brain diseases.

It has been reported that 12-HETE induces a chemotactic reaction of smooth muscle cells in rat (Atherosclerosis, 44, 339, (1982)). It was thought that such chemotactic action of 12(S)-HETE produced by 12-lipoxygenase in plasma platelets might be related to the induction of arteriosclerosis.

Recent studies have shown that some types of cancer cells can induce aggregation of plasma platelets. Cancer cells activate plasma platelets, in such a way that metabolites of arachidonate are released. Among these metabolites, a considerable amount of 12-HETE was detected (Cancer Res., 47, 6751, (1987)).

It has also been found that a process of cancer metastasis involves adhesion of a cancer cell(s) to subendothelial matrices through receptors, the expression of which is enhanced by 12-HETE (Cancer Res., 49, 1029, (1989)). Various inhibitors are known as shown by (1) Hamberg, M., Samuelson, B. Proc. Natl. Acad. Sci. U.S.A., 71, 3400 (1974); and (2) Honn, K. V., Grossi, I. M., Steinert, B. W., Chopra, H., Onoda, J., Nelson, K. K., Taylor, J. D., Advances in Prostaglandins, Thromboxane, and Leukotriene Research, Vol. 19, Raven Press, Ltd., New York, 439-443 (1989).

A 12-lipoxygenase inhibitor inhibits the production of 12-HETE by 12-lipoxygenase. Therefore, 12-lipoxygenase inhibitors may be useful for the treatment and/or prevention of inflammation, cancer metastasis, immune diseases, psoriasis, arteriosclerosis and/or ischaemic cardiovascular diseases.

OBJECTS

It is therefore an object of the present invention to provide compounds which inhibit 12-lipoxygenase. These and other objects will become increasingly apparent by reference to the following description.

GENERAL DESCRIPTION

The present invention relates to aryl aliphatic acids, and finds the compounds possess inhibitory activities against 12-lipoxygenase. The compounds of the present invention suppress the production of 12-HETE by binding 12-lipoxygenase and thus are useful for the treating and/or prevention of inflammation, immune diseases, psoriasis, arteriosclerosis and/or ischaemic cardiovascular diseases and also can act as suppressing agents of metastasis of cancer.

In particular, the present invention is related to aryl aliphatic acids of the formula

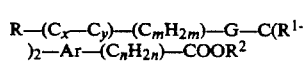

wherein n and m are independently 1-6;

wherein the pattern of substitution in the aryl ring (Ar) is independently ortho-, meta- or para-;

wherein G is O or S;

wherein each $R^1$ is independently H or lower alkyl or a combination thereof;

wherein $[C_x.C_y]$ is independently ethynylene, cis-vinylene, trans-vinylene, ethylene, propadienylene or arylene, particularly phenylene and other monocyclic unsaturated groups containing 3 to 6 carbon atoms;

wherein R is independently pentyl, hexyl, heptyl, octyl, nonyl, decyl, undecyl, dodecyl, tridecyl, tetradecyl, phenyl, benzyl, phenethyl, phenylpropyl, phenylbutyl or phenylpentyl or isomeric groups thereof;

wherein $R^2$ is H, a salt, lower alkyl, or alkylaryl, preferably containing 1 to 8 carbon atoms.

In the general formula $[C_nH_{2n}]$ and $[C_mH_{2m}]$ means methylene, ethylene, trimethylene, tetramethylene, pentamethylene, hexamethylene and isomeric groups thereof. For example, it may be easily understood that alkyl, alkoxy, alkenyl, alkylene, and alkenylene groups include straight-chained and also branched-chained ones, to those skilled in the art.

The compounds of the general formula can be converted into the corresponding salts. Non-toxic and water-soluble salts are preferable. Suitable salts, for example, are follows: salts of alkaline metal (sodium, potassium, etc.), salts of alkaline earth metal (calcium, magnesium, etc.) ammonium salts, salts of pharmaceutically acceptable organic amine (tetramethylammonium, trimethylamine, dimethylamine, cyclopentylamine, benzylamine, phenethylamine, piperidine, monoethanolamine, diethanolamine, tris(hydroxymethyl)amine, lysine, arginine, N-methyl-Dglucamine, etc.).

The compounds of the general formula or salts thereof can be in a form of hydrate without affecting activity.

SPECIFIC DESCRIPTION

Each symbol in the scheme(s) is as described hereinbefore. Various known methods were used for synthesizing the compounds of the present invention, included are:

1. Tamaru, Y., et al., Organic Syntheses, Vol. 67, 98 (1988).
2. Pasto, D. J., Tetrahedron, 40, 15, 2804 (1984); Elsevier C. J., Vermeer, P. J. Org. Chem. 54, 3726 (1989).
3. Gooding, O. W., Beard, C. C., Jackson, D. Y., Wren, D. L., Cooper, G. F. J. Org. Chem. 56, 1083 (1991)
4. Appel, R. Angew. Chem., Int. Ed. Engl. 14, 801 (1975).
5. Burgess, K., Jennings, L. D., J. Am. Chem. Soc., 113, 6129 (1991).
6. Theis, A. B., Townsend, C. A. Synth. Commun. 11, 157 (1981).

In each reaction in the present specification, the intermediates or products can be purified by conventional means, for example, by distillation at atmospheric or reduced pressure, high performance liquid chromatography, thin layer chromatography or column chromatography using silica gel or magnesium silicate, washing or recrystallization. Purification can be carried out after each reaction, or after a series of reactions.

Starting materials and reagents in the present invention are known per se or may be prepared by known methods.

In the first approach (Method A), benzenedimethanols (I) were monoprotected by treatment with one equivalent of t-butyldimethylsilyl chloride (TBSCl) and iodinated to afford II.

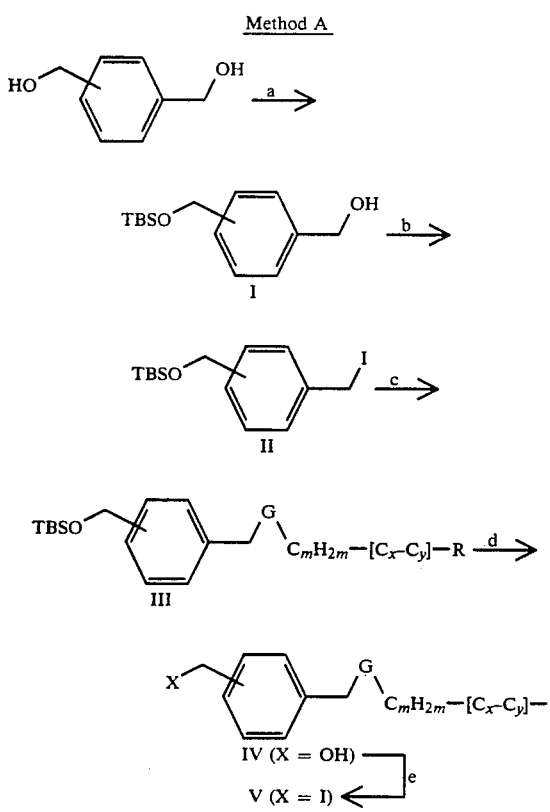

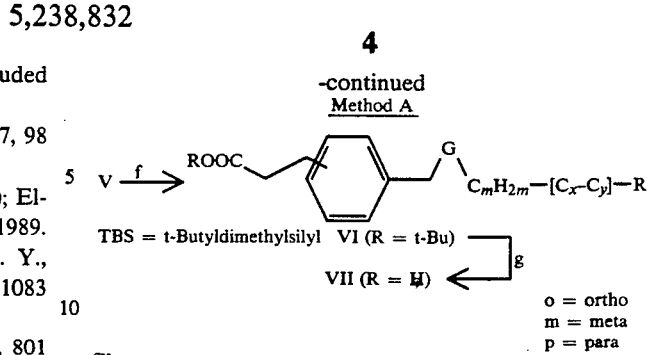

Key:
[a] TBSCl, imidazole, DMF, 12 h, 25° C.;
[b] Ph$_3$P, imidazole, I$_2$, CH$_3$CN—Et$_2$O, 1 h, 25° C.;
[c] R—[C$_x$–C$_y$]—(C$_m$H$_{2m}$) GNa, THF, 12 h, 25° C.;
[d] HF, Pyridine, CH$_3$CN, 12 h, 25° C.;
[e] PH$_3$P, imidazole, I$_2$, CH$_3$CN—Et$_2$O, 1 h, 25° C.;
[f] CH$_3$COO-t-Bu, lithium diisopropylamide, THF, −78° C., 1 h;
[g] CF$_3$CO$_2$H, CH$_2$Cl$_2$, 20 h, 25° C.

Ethers III were prepared by a standard Williamson synthesis. Subsequent treatment of III with hydrofluoric acid in acetonitrile followed by iodination of the resulting alcohols IV provided V. The final elongations were carried out in tetrahydrofuran (THF) at −78° C. using a two fold excess of the lithium enolate of tert-butyl acetate and quenching at the same temperature after 1 hour. The resulting esters VI were hydrolysed by treatment with trifluoroacetic acid to afford the desired acids VII.

In the second approach (Method B), bromobenzyl bromides VIII were converted to ethers or sulfides utilizing previously prepared long chain alcohols or thiols.

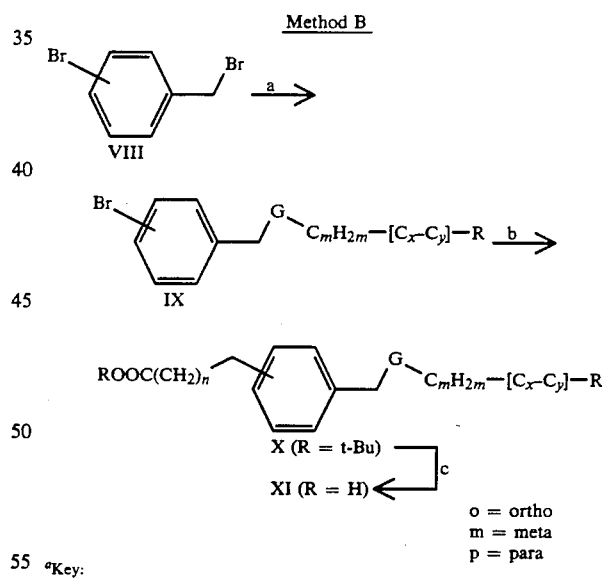

Key:
[a] R—[C$_x$–C$_y$]—(C$_m$H$_{2m}$)GNa, THF, 12 h, 25° C.;
[b] I(CH$_2$)$_n$COOEt, ZnCU$^3$, Toluene-Dimethylacetamide, 4 h, 60° C., Pd(Ph$_3$P)$_4$, 24 h, Δ;
[c] NaOH, MeOH, 5 h, 25° C.

The zinc reagents from ethyl 3-iodopropanoate or ethyl 4-iodobutanoate were prepared by treatment of these iodo-esters with an excess of zinc-copper couple (Tamaru, Y., et al., Organic Syntheses, Vol. 67, 98 (1988)). This was followed by the addition of 9 and a catalytic amount of palladium(O). The reaction mixture was stirred at reflux of toluene for a 12 hour period. A reasonable amount of the desired coupled products could be isolated. The success of this palladium(O)- mediated coupling procedure was found to be strongly dependent upon the length and position of the lipophilic chain. The best results were obtained for the smallest lipophilic chains in a para position relative to the bromide. These very convenient syntheses of phenylpropionic acid derivatives 11 were completed by alkaline hydrolyses of the corresponding esters 10 in methanol.

Table I shows structural variations of compounds prepared.

For the synthesis of arylpropionic acid derivatives, convenient transformations were developed to build various side chains that were not available from commercial sources. Our approaches to these side chains are described in Methods C, D, E and F.

Method C

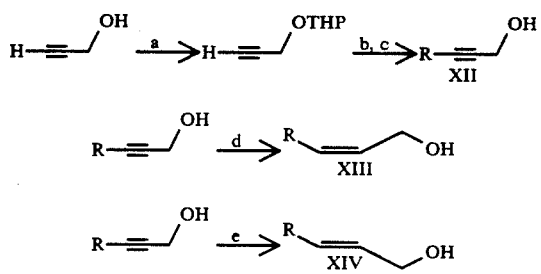

<sup>a</sup>Key:
<sup>a</sup>Dihydropyran, pTsOH, CH$_2$Cl$_2$, 25° C.;
<sup>b</sup>n-BuLi, RI, THF, Hexamethylphosphoramide (HMPA), 1 h, 0° C.; pTsOH, MeOH, 25° C.;
<sup>d</sup>H$_2$, Pd/CaCO$_3$ Lead poisoned, EtOAc, 25° C., 10 h;
<sup>e</sup>LiAlH$_4$, Et$_2$O, reflux, 24 h.

Method D

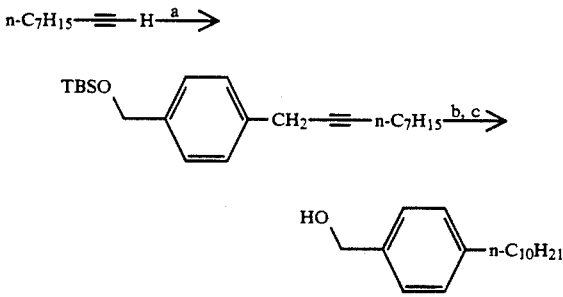

<sup>a</sup>Key:
<sup>a</sup>n-BuLi, THF, −78° C., 0.5 h, II, Hexamethylphosphoramide (HMPA), 0° C., 1 h
<sup>b</sup>H$_2$, 10% Pd/C, EtOAc, 25° C.;
<sup>c</sup>10% HF, CH$_3$CN, 25° C., 1 h.

Method E

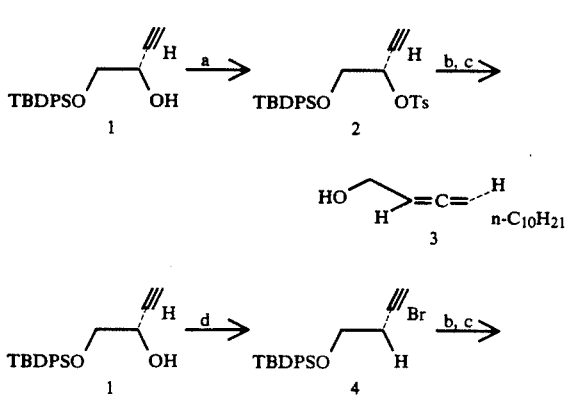

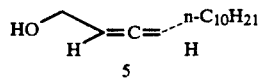

<sup>a</sup>Key:
<sup>a</sup>TsCl, Et$_3$N, CH$_2$Cl$_2$, 25° C., 17 h;
<sup>b</sup>n-C$_{10}$H$_{21}$MgBr, CuBr-Dimethyl sulfide Tetrahydrofuran, 0° C., 0.25 h;
<sup>c</sup>Tetrabutylammonium Fluoride, THF, 25° C., 2 h;
<sup>d</sup>Ph$_3$P, Pyridine, CBr$_4$, THF, 25° C., 1 h.

A first set of long chain alcohols was easily attainable through the use of the readily available propargylic alcohol (Method C). Cis alkenes XIII were obtained by partial hydrogenation of the corresponding alkynes. The trans isomers XIV were prepared by alkyne reduction with a two fold excess of LiAlH$_4$.

Aryl-containing side chain construction (Method D) was achieved by Method D. Allenyl side chains were prepared according to Method E. Based on the knowledge that various organometallic reagents react with chiral propagylic derivatives to form optically active allenes, (Pasto, D. J., Tetrahedon 40, 15 2804 (1984)); and Elsevier, C. J., et al., J. Organic Chem. 54, 3726 (1989)) it was decided to start the approach with previously described alcohol 1 (Gooding, O. W., et al., J. Org. Chem. 56, 1083 (1991)). To prepare the dextrorotatory allene 3, the alcohol 1 was treated with p-toluenesulfonyl chloride and triethylamine in dichloromethane giving tosylate 2. Subsequent copper-catalyzed Grignard addition of decylmagnesium bromide to 2 afforded the protected α-allenic alcohol. Further treatment with tetrabutylammonium fluoride in THF gave 3. The levorotatory form was prepared by bromination of 1 using carbon tetrabromide-triphenylphosphine (Appel, R., Angew. Chem., Int. Ed. Engl. 14, 801 (1975)) in THF containing pyridine. The resulting bromide 4 was converted to 5 by the same procedure as the one described above for the synthesis of 3.

Enzymatic resolution of racemate 6 (Method F) provided the two enantiomeric series of alcohols 7 and 8 in high enantiomeric excess (ee>95% determined by :H NMR of the corresponding Mosher esters). The absolute configuration of those alcohols was assigned by correlation with previous studies on related substrates (Burgess, K., Jennings, L. D., J. Am. Chem. Soc. 113, 6129 (1991)).

Method F n-C$_{10}$H$_{21}$—≡—⟨OH⟩ —<sup>a</sup>→ n-C$_{10}$H$_{21}$—≡—/OH +
6      7 [α]$_D^{25}$ = −16.3° n-C$_{10}$H$_{21}$—≡—/OAc n-C$_{10}$H$_{21}$—≡—/OAc —<sup>b</sup>→ n-C$_{10}$H$_{21}$—≡—/OH

8 [α]$_D^{25}$ = +15.8°

<sup>a</sup>Key:
<sup>a</sup>lipase P 30, isopropenyl acetate, 40° C., 24 h;
<sup>b</sup>potassium carbonate, MeOH, 25° C. 1 h.

TABLE I

Variations on the General Structure:
R—($C_x$—$C_y$)—($C_mH_{2m}$)—G—$CH_2$—Ar—($C_nH_{2n}$)—COOH

| Cpd | R | ($C_x$—$C_y$) | ($C_mH_{2m}$) | G | Ar | ($C_nH_{2n}$) | Method |
|---|---|---|---|---|---|---|---|
| 9 | n-$C_{10}H_{21}$ | C≡C | $CH_2$ | O | m-$C_6H_4$ | $(CH_2)_2$ | B |
| 10 | n-$C_8H_{17}$ | C≡C | $CH_2$ | O | m-$C_6H_4$ | $(CH_2)_2$ | A |
| 11 | n-$C_{10}H_{21}$ | C≡C | $CH_2$ | O | m-$C_6H_4$ | $(CH_2)_3$ | B |
| 12 | n-$C_8H_{17}$ | C≡C | $CH_2$ | S | m-$C_6H_4$ | $(CH_2)_2$ | A |
| 13 | n-$C_8H_{17}$ | CH=CH (cis) | $CH_2$ | O | m-$C_6H_4$ | $(CH_2)_2$ | A |
| 14 | n-$C_5H_{11}$ | C≡C | $(CH_2)_2$ | O | m-$C_6H_4$ | $(CH_2)_2$ | B |
| 15 | n-$C_6H_{13}$ | C≡C | $CH_2$ | O | m-$C_6H_4$ | $(CH_2)_2$ | B |
| 16 | n-$C_7H_{15}$ | C≡C | $CH_2$ | O | m-$C_6H_4$ | $(CH_2)_2$ | B |
| 17 | n-$C_{10}H_{21}$ | C≡C | $C(CH_3)_2$ | O | p-$C_6H_4$ | $(CH_2)_2$ | A |
| 18 | n-$C_{10}H_{21}$ | C≡C | $CH_2$ | O | p-$C_6H_4$ | $CH_2C(CH_3)_2$ | A |
| (±)-19 | n-$C_{10}H_{21}$ | C≡C | $CH_2$ | O | p-$C_6H_4$ | $CH_2CH(CH_3)$ | A |
| (±)-20 | n-$C_{10}H_{21}$ | C≡C | $CH(CH_3)$ | O | p-$C_6H_4$ | $(CH_2)_2$ | A |
| (+)-21 | n-$C_{10}H_{21}$ | C≡C | $CH(CH_3)$ | O | p-$C_6H_4$ | $(CH_2)_2$ | A |
| (−)-22 | n-$C_{10}H_{21}$ | C≡C | $CH(CH_3)$ | O | p-$C_6H_4$ | $(CH_2)_2$ | A |
| 23 | n-$C_{10}H_{21}$ | C≡C | $CH_2$ | O | o-$C_6H_4$ | $(CH_2)_2$ | A |
| 24 | n-$C_{10}H_{21}$ | C≡C | $CH_2$ | O | p-$C_6H_4$ | $(CH_2)_2$ | B |
| 25 | n-$C_6H_{13}$ | C≡C | $CH_2$ | O | p-$C_6H_4$ | $(CH_2)_2$ | A |
| 26 | n-$C_8H_{17}$ | C≡C | $CH_2$ | O | p-$C_6H_4$ | $(CH_2)_2$ | A |
| 27 | n-$C_{12}H_{25}$ | C≡C | $CH_2$ | O | p-$C_6H_4$ | $(CH_2)_2$ | A |
| 28 | n-$C_{14}H_{29}$ | C≡C | $CH_2$ | O | p-$C_6H_4$ | $(CH_2)_2$ | A |
| 29 | Ph—$(CH_2)_4$ | C≡C | $CH_2$ | O | p-$C_6H_4$ | $(CH_2)_2$ | A |
| 30 | n-$C_{10}H_{21}$ | p-$C_6H_4$ | $CH_2$ | O | p-$C_6H_4$ | $(CH_2)_2$ | A |
| 31 | n-$C_{10}H_{21}$ | CH=CH (cis) | $CH_2$ | O | p-$C_6H_4$ | $(CH_2)_2$ | A |
| 32 | n-$C_{10}H_{21}$ | CH=CH (trans) | $CH_2$ | O | p-$C_6H_4$ | $(CH_2)_2$ | A |
| 33 | n-$C_{10}H_{21}$ | $CH_2$—$CH_2$ | $CH_2$ | O | p-$C_6H_4$ | $(CH_2)_2$ | A |
| (+)-34 | n-$C_{10}H_{21}$ | CH=C=CH | $CH_2$ | O | p-$C_6H_4$ | $(CH_2)_2$ | A |
| (−)-35 | n-$C_{10}H_{21}$ | CH=C=CH | $CH_2$ | O | p-$C_6H_4$ | $(CH_2)_2$ | A |
| 36 | n-$C_{10}H_{21}$ | CH=CH (trans) | $CH_2$ | O | m-$C_6H_4$ | $(CH_2)_2$ | A |
| 37 | n-$C_{10}H_{21}$ | $CH_2$—$CH_2$ | $CH_2$ | O | m-$C_6H_4$ | $(CH_2)_2$ | A |
| 38 | Ph | C≡C | $CH_2$ | O | m-$C_6H_4$ | $(CH_2)_2$ | B |

Experimental Section

General Procedures. All air-sensitive reactions were conducted in flame- or oven dried apparatus under a positive pressure of argon. Air-sensitive liquids were transferred by syringe or double-ended needle and introduced into the reaction vessel through rubber septum caps. Commercial CuBr was purified by continuous extraction with tetrahydrofuran. CuBr-dimethyl sulfide complex was prepared by the literature method (Theis, A. B., Townsend, C. A., Synth. Commun. 157 (1981)). Zn-Cu couple was prepared according to literature (Tamaru, Y., et al., Organic Syntheses, Vol. 67, 98 (1988)). Lipase P-30 was obtained from the Amano Enzyme Co.

$^1$H NMR spectra were recorded at 300 MHz. $^{13}$C NMR spectra were measured at 75.48 MHz. Infrared spectra were recorded on a FT spectrometer. Optical rotations were determined with a Perkin-Elmer polarimeter.

Column chromatography was carried out with silica gel (230–400 mesh). All chromatographic separations were monitored by TLC analyses on silica gel. Yields are reported for chromatographically pure compounds.

Arylpropionic Acid Derivatives. Method A:

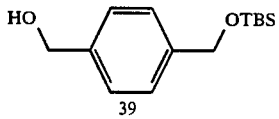

39

4-[(tert-Butyldimethylsilyl)oxymethyl phenylmethanol (39). A flask was charged with 3.00 g of a 60% dispersion of NaH in oil. The dispersion was washed with three 10-mL portions of THF. The NaH was suspended in 70 mL of THF and cooled to 0° C, followed by the slow addition of a solution of 1,4-benzenedimethanol (Aldrich) (8.50 g, 62 mmol) in THF (10 mL) to the mixture. After 25 minutes at 0° C, an additional 40-mL portion of THF was added to the mixture, and the cold bath was removed. The reaction mixture was stirred at 25° C. for 30 minutes and was then recooled to 0° C. At this time, tert-butyldimethylsilyl chloride (10.19 g, 68.20 mmol, 1.1 equiv) was added to the mixture. The solution was allowed to warm to 25° C. over a 1 hour period and was stirred at this temperature for an additional 12 hours. The mixture was poured into 50 mL of water and extracted with three 50-mL portions of ether. The combined ether extracts were dried over $MgSO_4$, filtered, and concentrated in vacuo to yield a yellow oil. Purification by flash silica gel chromatography (85:15 petroleum ether/EtOAc) yielded 9.6g (50%) of monoprotected material (39) as a clear oil: $R_f$ 0.62 (8:2 petroleum ether/EtOAc); IR (neat) 3550–3100 (b, OH), 3000, 2800, 1600, 1493, 1256, 1192, 1131, 1087 cm$^{-1}$; $^1$H NMR (CDCl$_3$) δ 7.31 (s, 4 H), 4.75 (s, 2 H), 4.60 (d, J=5.4 Ha, 2 H), 2.60 (s, 1 H), 0.97 (s, 9 H), 0.13 (s, 6 H); $^{13}$C NMR (CDCl$_3$) δ 140.89, 139.77, 127.12, 126.39, 65.07, 64.95, 26.11, 18.57, −5.08.

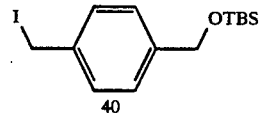

40

1-[(tert-Butyldimethylsilyl)oxymethyl]-4-iodomethylbenzene (40). A flask was charged with Ph$_3$P (3.93 g, 15 mmol, 1.5 equiv), imidazole (1.24 g, 20 mmol, 2 equiv) and a 3/1 mixture of Et$_2$O/CH$_3$CN (100 mL). The mixture was stirred until dissolution was complete. At this time, I$_2$ (3.81 g, 15 mmol, 1.5 equiv) was added and vigorous stirring was continued until a yellow suspension formed. A solution of (39) (3.58 g, 10 mmol) in 10 mL of the same solvent was then added. After 1 hour, the mixture was concentrated in vacuo and the resulting crude material was taken up into 100 mL of hexane, the solution was washed with 100 mL of a saturated solution of sodium bisulfite. The aqueous solutions were back extracted with two 100-mL portions of hexane. The combined organic extracts were dried over MgSO$_4$, filtered, and concentrated in vacuo to yield a yellow oil. Purification by flash silica gel chromatography (95:05 petroleum ether/EtOAc) afforded 4.40 g (93%) of the iodo derivative (40) as a clear colorless oil: R$_f$ 0.85 (9:1 petroleum ether/EtOAc); $^1$H NMR (CDCl$_3$) δ 7.35 (d, J=8.1 Hz, 2 H), 7.26 (d, J=8.1 Hz, 2 H), 4.71 (s, 2 H), 4.47 (s, 2 H), 0.96 (s, 9 H), 0.11 (s, 6 H); $^{13}$C NMR (CDCl$_3$) δ 141.28, 137.78, 128.63, 126.39, 64.60, 25.95, 5.89, −5.25.

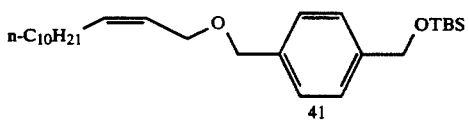

41 cis-1-(tert-Butyldimethylsilyloxymethyl)-4-(2-tridecenyloxymethyl)benzene (41). A flask was charged with 60 mg of a 60% dispersion of NaH in oil. The dispersion was washed with three 2-mL portions of THF. The NaH was suspended in 5 mL of THF and cooled to 0° C. A solution Of cis-2-tridecen-1-ol (206 mg, 1.1 mmol, 1.1 equiv) in THF (1 mL) was slowly added to the mixture. After 25 minutes the cold bath was removed and stirring was continued for an additional 10 minutes. At this time a solution of (40) (361 mg, 1 mmol) in THF (1 mL) was added and stirring was continued for 12 hours. The mixture was poured into water (20 mL) and ether (25 mL). The organic layer was separated and washed with three 10-mL portions of water. The ether extract was dried (MgSO$_4$) filtered and concentrated by rotary evaporation to yield a yellow oil. Purification by flash silica gel chromatography (95:05 petroleum ether/EtOAc) afforded 341 mg (85%) of the coupled produced (41) as a clear colorless oil: R$_f$ 0.80 (9:1 petroleum ether/EtOAc); $^1$H NMR (CDCl$_3$) δ 7.20 (s, 4 H), 5.61 (m, 2H), 4.76 (s, 2H), 4.52 (s, 2H), 4.08 (d, J=4.8 Hz, 2H), 2.05 (m, 2H), 1.29 (m, 16 H), 0.97 (s, 9 H), 0.91 (t, J=6.9 Hz, 3 H), 0.12 (s, 6 H); $^{13}$C NMR (CDCl$_3$) δ 140.76, 137.04, 127.71, 126.04, 125.98, 71.86, 65.58, 64.80, 31.92, 29.62, 29.56, 29.52, 29.24, 29.36, 27.61, 25.94, 22.69, 18.57, 14.12, −5.25.

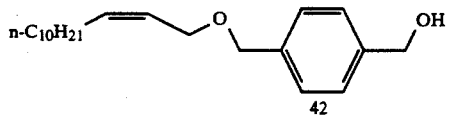

42 cis-4-(2-Trideceny1oxymethyl)phenylmethanol (42). To a solution of silyl ether (41) (341 mg, 0.84 mmol) in CH$_3$CN (10 mL) was added 50% aqueous HF (1 mL) the mixture was stirred at room temperature for 15 minutes. The reaction mixture was poured into saturated aqueous NaHCO$_3$ (50 mL) and ether (75 mL). The organic layer was separated and washed with two 50-mL portions of water, dried (MgSO$_4$), and concentrated to yield (42) (290 mg, 98%) as a colorless oil: R$_f$ 0.24 (9:1 petroleum ether/EtOAc); $^1$H NMR (CDCl$_3$) δ 7.30 (s, 4 H), 5.60 (m, 2 H), 4.63 (s, 2 H), 4.49 (s, 2 H), 4.07 (d, J=5.1 Hz, 2 H), 239 (s, 2 H), 2.04 (q, J=6.6 Hz, 2 H), 1.27 (m, 16 H), 0.89 (t, J 6.6 Hz, 2 H); $^{13}$C NMR (CDCl$_3$) δ 140.49, 137.82, 134.24, 128.10, 127.12, 125.94, 71.88, 65.85, 65.03, 32.03, 29.76, 29.66, 29.48, 29.37, 27.73, 22.82, 14.24.

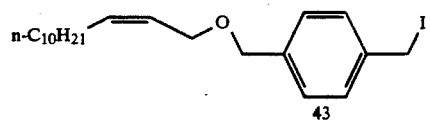

43 cis-1-Iodomethyl-4-(z-tridecenyoxymethyl) benzene (43). A flask was charged with Ph$_3$P (314 mg, 1.2 mmol, 1.5 equiv), imidazole (109 mg, 1.6 mmol, 2 equiv) and 10 mL of a 3/1 mixture of Et$_2$O/CH$_3$CN. The resulting mixture was stirred until dissolution was complete. At this time, I$_2$ (305 mg, 1.2 mmol, 1.5 equiv) was added and vigorous stirring was continued until a yellow suspension formed, a solution of (42) (250 mg, 0.8 mmol) in 1 mL of the same solvent was then added. After 1 hour, the mixture was concentrated in vacuo and the resulting yellow oil was taken up into 50 mL of hexane and 30 mL of a saturated solution of sodiumbisulfite this was extracted with two 30-mL portions of hexane. The combined organic extracts were dried over MgSO$_4$, filtered, and concentrated in vacuo to yield a yellow oil. Purification by flash silica gel chromatography (95:05 petroleum ether/EtOAc) afforded 350 mg (93%) of the iodo derivative (43) as a clear colorless oil: R$_f$ 0.75 (9:1 petroleum ether/EtOAc); $^1$H NMR (CDCl$_3$) δ 7.33 (d, J=8.1 Hz, 2 H), 7.18 (d, J=8.1 Hz, 2 H), 5.62 (m, 2 H), 4.45 (s, 2 H), 4.40 (s, 2 H), 4.05 (d, J=5.1 Hz, 2 H), 2.05 (m, 2 H), 1.37 (m, 16 H), 0.91 (t, J=6.6 Hz, 3 H); $^{13}$C NMR (CDCl$_3$) δ 138.50, 138.69, 134.26, 128.91, 128.28, 125.97, 71.74, 66.02, 32.06, 29.78, 29.70, 29.51, 29.38, 27.78, 22.86, 14.30, 5.66.

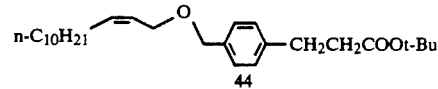

44 tert-Butyl cis-3-[4-(z-Tridecenyloxymethyl) phenyl]-propanoate (44). A solution of tert-butyl acetate (0.2 mL, 1.5 mmol, 2 equiv) in dry THF (1 mL) was added to a solution of LDA. (The latter was prepared by adding n-BuLi (0.68 mL, 2.5 M in hexane, 1.72 mmol) to a solution of diisopropylamine (0.10 mL, 1.89 mmol) in THF (4 mL) at −78° C. and stirring for 30 minutes). The resulting mixture was stirred for 30 minutes at −78° C. and (43) (350 mg, 0.75 mmol) in THF (1 mL) was added. After 1 hour, the reaction mixture was allowed to warm to 0° C. and immediately poured into water (20 mL) and ether (30 mL). The organic layer was separated and washed with three 15-mL portions of water. The other extract was dried (MgSO$_4$) filtered and concentrated by rotary evaporation. Flash chromatography eluted by 95:05 petroleum ether/EtOAc furnished (44) (250 mg, 78%) as a colorless oil: R$_f$0.68 (9:1 petroleum ether/EtOAc); $^1$H NMR (CDCl$_3$) δ 7.27 (d, J =8.1 Hz, 2H), 7.17 (d, J=8.1 Hz, 2 H), 5.59 (m, 2 H), 4.47 (s, 2 H), 4.06 (d, J=4.5 Hz, 2 H), 2.90 (t, J=7.8 Hz, 2 H), 2.53 (t, J=7.8 Hz, 2 H), 2.04 (m, 2 H), 1.42 (s, 9 H), 1.27 (m, 16 H), 0.89 (t, J=6.9 Hz, 3 H); $^{13}$C NMR (CDCl$_3$) δ 172.32, 140.26, 136.38, 134.02, 128.44, 128.07, 126.13, 80.38, 71.96, 65.78, 37.18, 32.03, 30.95, 29.74, 29.67, 29.63, 29.47, 29.36, 28.18, 27.73, 22.79, 14.24.

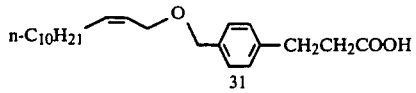

cis-3-[4-(2-Tridecenyloxymethyl)-phenyl]propanoic Acid (31). A solution of (44) (250 mg, 0.6 mmol) in a 1:5 mixture of trifluoroacetic acid and $CH_2Cl_2$ (10 mL) was stirred at 25° C. for 12 hours and evaporated to dryness in vacuo at room temperature. Purification by flash silica gel chromatography (25:01 $CH_2Cl_2$/MeOH) afforded 205 mg (95%) of the arylpropionic acid derivative (31) as a white solid: mp 35–36° C.; $R_f$ 0.35 (20:01 $CH_2Cl_2$/MeOH); $^1H$ NMR ($CDCl_3$) δ 10.50 (s, 1 H), 7.30 (d, J=7.8 Hz, 2 H), 7.20 (d, J=7.8 Hz, 2 H), 5.61 (m, 2H), 4.50 (s, 2 H), 4.09 (d, J=4.8 Hz, 2 H), 2.97 (t, J=7.8 Hz, 2 H), 2.68 (t, J=7.8 Hz, 2 H), 2.05 (m, 2 H), 1.28 (m, 16 H), 0.90 (t, J=6.6 Hz, 3 H); $^{13}C$ NMR ($CDCl_3$) δ 179.06, 139.71, 136.59, 134.22, 128.42, 128.28, 125.98, 71.89, 65.83, 35.75, 32.04, 30.43, 29.75, 29.67, 29.47, 29.37, 27.74, 22.81, 14.24; HRMS calcd for $C_{23}H_{36}O_3$ (M+), 360.2664 found 360.2658.

Arylpropionic Acid Derivatives. Method B:

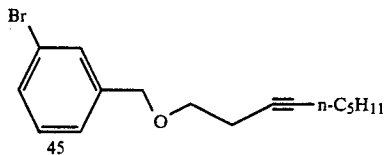

1-Bromo-3-(3-nonynyloxymethyl)benzene (45). A flask was charged with 50 mg of a 60% dispersion of NaH in oil. The dispersion was washed with three 2-mL portions of THF. The NaH was suspended in 5 mL of THF and cooled to 0° C. A solution of 3-nonyn-1-ol (152 mg, 1.1 mmol, 1.1 equiv) in THF (1 mL) was slowly added. After 25 minutes the cold bath was removed and stirring was continued for an additional 10 minutes. At this time a solution of 3-bromobenzyl bromide (250 mg, mmol) in THF (1 mL) was added and stirring continued for 12 hours. The mixture was poured into water (20 ml) and ether (25 mL). The organic layer was separated and washed with three 10-ml portions of water. The ether extract was dried ($MgSO_4$) filtered and concentrated by rotary evaporation to yield a yellow oil. Purification by flash silica gel chromatography (95:05 petroleum ether/EtOAc) afforded 262 mg (85%) of the coupled product (45) as a clear colorless oil: $R_f$ 0.88 (9:1 petroleum ether/EtOAc); $^1H$ NMR ($CDCl_3$) δ 7.40 (m, 4 H), 4.55 (s, 2 H), 3.56 (t, J=6.9 Hz, 2 H), 2.48 (tt, $J_1$=6.9 Hz, $J_2$=2.4 Hz, 2 H), 2.15 (tt, $J_1$=7.2 Hz, $J_2$=2.4 Hz, 2 H), 1.40 (m, 6 H), 0.89 (t, J=7.2 Hz, 3 H); $^{13}C$ NMR ($CDCl_3$) δ 140.82, 130.78, 130.65, 130.09, 126.12, 122.68, 81.81, 72.74, 69.29, 31.20, 28.80, 22.35, 20.29, 18.86, 14.12.

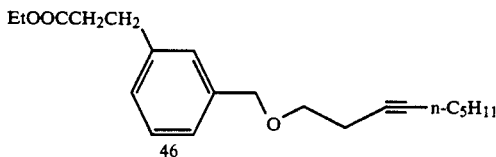

Ethyl 3-[4-(3-Nonynyloxymethyl) phenyl]propanoate (46). A flask was charged with Zn-Cu couple (200 mg, 3 mmol) solution of ethyl 3-iodopropanoate (510 mg, 2 mmol) in dry toluene (4 mL) and dry N,N-dimethylacetamide (2mL) was added. The mixture was vigorously stirred for 1 hour at room temperature and then heated at gentle reflux for 4.5 hours. After the mixture was cooled to 60° C, a solution of tetrakis(triphenylphosphine)palladium(0)(30 mg, 0.026 mmol) in toluene (2 mL) was added over 1 minute and stirring was continued for 5 minutes at the same temperature. A solution of (45) (309 mg, 1 mmol) in dry toluene (2 mL) was added and the mixture was refluxed for 12 hours. The reaction mixture was allowed to cool to 25° C. and filtered through a Celite pad. The filter cake was washed with ether (50 mL). The filtrate was successively washed with a solution of i N ammonium chloride (10 mL), a solution of saturated sodium hydrogen carbonate (10 mL) and a solution of saturated sodium chloride (10 mL). The aqueous phases were back extracted with ether (30 mL), the combined organic extracts were dried ($MgSO_4$), filtered, concentrated by rotary evaporation to yield a yellow oil. Purification by flash silica gel chromatography (97:03 petroleum ether/EtOAc) afforded (46) (165 mg, 51%) as a colorless oil: $R_f$ 0.44 (95:05 petroleum ether/EtOAc); $^1H$ NMR ($CDCl_3$) δ 7.19 (m, 4 H), 4.51 (s, 2 H), 4.12 (q, J=7.2 Hz, 2 H), 3.55 (t, J=7.2 Hz, 2 H), 2.94 (t, J=8.1 Hz, 2 H), 2.61 (t, J=8.1 Hz, 2 H), 2.46 (tt, $J_1$=6.9 Hz, $J_2$=2.1 Hz, 2 H), 2.13 (tt, $J_1$=7.2 Hz, $J_2$=2.4 Hz, 2 H), 1.40 (m, 6 H), 1.22 (t, J=7.2 Hz, 3 H), 0.88 (t, J=6.9 Hz, 3 H); $^{13}C$ NMR ($CDCl_3$) δ 173.01, 140.87, 138.58, 128.68, 127.75, 81.64, 76.67, 72.99, 69.15, 60.53, 36.02, 31.01, 31.18, 28.81, 22.34, 20.28, 18.85, 14.32, 14.12.

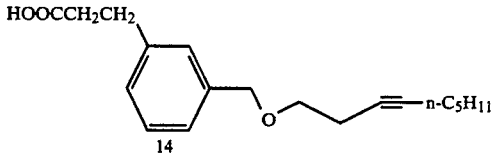

3-[4-(3=Nonynloxymethyl)phenyl]propanoic Acid (14). A solution of (46) (150 mg, 0.45 mmol) in a mixture of MeOH (4 mL) and 1 N NaOH (1 mL) was stirred at room temperature for 3 hours. The reaction mixture was concentrated in vacuo, $H_2O$ (20 mL) was added, and the pH was adjusted to 4 with 10% AcOH. Ether (30mL) was added. The organic layer was separated and washed with water (20mL). The ether extract was dried ($MgSO_4$) and concentrated by rotary evaporation. Purification by flash silica gel chromatography (20:01 $CH_2Cl_2$/MeOH) afforded (14) (129 mg, 95%) as a colorless oil: $R_f$ 0.31 (20:01 $CH_2Cl_2$/MeOH); $^1H$ NMR ($CDCl_3$) δ 10.5 (s, 1 H), 7.21 (m, 4 H), 4.55 (s, 2 H), 3.57 (t, J=6.9 Hz, 2 H), 2.97 (t, J=8.1; Hz, 2 H), 2.69 (t, J=8.1 Hz, 2 H), 2.49 (tt, $J_1$=7.2 Hz, $J_2$=2.4 Hz, 2 H), 2.15 (tt, $J_1$=6.9 Hz, $J_2$=2.1 Hz, 2 H), 1.40 (m, 6 H), 0.90 (t, J=6.9 Hz, 3H); $^{13}C$ NMR ($CDCl_3$) δ 179.20, 140.47, 138.62, 128.78, 127.73, 125.93, 81.69, 76.67, 72.95, 69.15, 35.70, 31.21, 30.63, 28.83, 22.36, 20.27, 18.86, 14.12.

General procedures for the preparation of the different lipophilic sidechains.

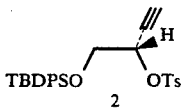

(S)-1-[tert=Butyldiphenylsilyl)oxy]-3-butyn-2-yl p-Toluenesulfonate (1). A solution of (S)-i-[tert-Butyldiphenylsilyl)oxy]-3-butyn-2-yl (1) (1.62 g, 5 mmol) of p-toluenesulfonyl chloride (1.14g, 6.00 mmol, 1.25 equiv) of triethylamine (631 mg, 6.25 mmol, 1.25 equiv), and $CH_2Cl_2$ (20 mL), was purged with argon and stirred for 17 hours. The mixture was diluted with ether (100 mL), washed twice with saturated aqueous $NaHCO_3$ (40 mL), and once with saturated NaCl (40 mL). The ether extracts were dried ($MgSO_4$), concentrated by rotary evaporation to yield a yellow oil. Purification by flash silica gel chromatography (92:08 hexane/$Et_2O$); afforded (2) (2.46 g, 99%) as a colorless oil: $R_f$ 0.34 (93:07 hexane/$Et_2O$); IR (neat) 3145, 2135, 1371, 1113,;$^1$H NMR ($CDCl_3$) δ 7.81 (m, 2H), 7.61 (m, 4 H), 7.30 (m, 8 H), 5.15 (m, 1 H), 3.83 (ddd, $J_1$=11.3 Hz, $J_2$=7.2 Hz, $J_3$=4.5 Hz, 2 H), 2.42 (s, 3 H) 2.40 (d, J=2.3 Hz, 1 H), 1.02 (m, 9 H); $^{13}$C NMR ($CDCl_3$)δ 145.00, 135.58, 134.78, 129.88, 129.65, 128.07, 127.77, 76.98, 71.21, 65.39, 26.63, 21.66.

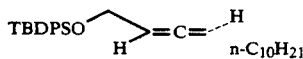

(S)-1-[tert-Butyldiphenylsilyl)oxy]-2,3-tetradecadiene. A THF suspension of $CuBr-Me_2S$ complex (60 mg, 5 mol % based on grignard reagent) was cooled to −78° C., and decylmagnesium bromide (1 M in $Et_2O$, 6 mL, 6 mmol, 2 equiv) was added. The resulting mixture was allowed to warm t 0° C., stirred for 3 minutes before being recooled to −78° C. A solution of (S)-1-[tert-butyldiphenylsilyl)oxy]-3-butyn-2-1 p-toluenesulfonate (2) (1.43 g, 3 mmol) in THF (5 mL) Was added. The reaction mixture was maintained at −78° C. for 1 hours and then was allowed to warm to 0° C. and stirred at this temperature for an additional 15 minutes. At this time it was quenched with saturated $NH_4Cl$ and stirred at room temperature for 10 minutes. The mixture was diluted with ether (100 mL) washed with 0.5 N HCl and aqueous $NaHCO_3$. The ether extracts were dried ($MgSO_4$) and concentrated by rotary evaporation to yield a yellow oil. Purification by flash silica gel chromatography (95:05 hexane/EtOAc) afforded (S)-1-[tert-butyldiphenyl silyl)oxy]-2,3-teradecadiene (1.08 g, 75%) as a colorless oil: $R_f$ (90:10 hexane/EtOAc); IR (neat) 3145, 2135, 1371, 1113 cm$^{-1}$; $^1$H NMR ($CDCl_3$) δ 7.74 (m, 4 H), 7.43 (m, 6 H), 5.27 (m, 1 H), 5.19 (m, 1 H), 4.25 (m, 2 H), 2.00 (m, 2 H), 1 29 (m, 16 H), 1.09 (s 9 H) 0.91 (m, 3 H); $^{13}$C NMR ($CDCl_3$) δ 203.20, 137.05, 134.10, 130.00, 127.30, 94.02, 91.80, 60.91, 32.02, 31.00, 29.73, 29.55, 29.44, 29.22, 28.77, 27.23, 22.79,14.21.

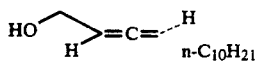

(S)-2,3-Tetradecadien-1-ol (3). To a solution of (S)-1-[tert-butyldiphenylsilyloxy]-2,3-tetradecadiene (900 mg, 2 mmol) in THF (15 mL) was added tetrabutylammonium fluoride (3 mmol, 1.5 equiv). The resulting mixture was stirred for hour and concentrated by rotary evaporation. The residue was taken up into ether (100 mL) and washed with water (50 mL). The organic extract was dried ($MgSO_4$), concentrated by rotary evaporation to yield a yellow oil. Purification by flash silica gel chromatography (90:10 hexane/EtOAc) afforded (S)-2,3-tetradecadien-1-ol (3) 30 (0.33 g, 80%) as a colorless oil: $R_f$ 0.32 (85:15 hexane/EtOAc); IR (neat) 3300, 2924, 2853, 1960, 1468, 1110, 1053, 1011, 871 cm$^{-1}$; $^1$H NMR ($CDCl_3$) δ 5.28 (m, 2 H), 4.09 (dd, $J_1$=5.4 Hz, $J_2$=3.3 Hz, 2 H), 2.01 (m, 2H), 1.90 (s, 1 H), 1.25 (m, 16 H), 0.87 (t, J=6.9 Hz, 3 H); $^{13}$C NMR ($CDCl_3$) δ 203.17, 94.02, 91.80, 60.92, 32.02, 29.73, 29.55, 29.44, 29.22, 28.77, 22.79, 14.21

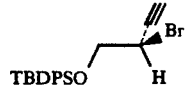

(R)-2-Bromo-1-[tert-butyldiphenylsilyloxyl]-3-butyne (4). A flask was charged with (S)-1-[(tert-Butyldiphenylsilyl)oxy]-3-butyn-2-ol (1) (1.30 g, 4 mmol), triphenylphosphine (2.52 g, 9.60 mmol), THF (30 mL), pyridine (360 mg, 4.56 mmol). To this mixture was added carbon tetrabromide (1.53 g, 4.60 mmol) in THF (10 ml) over a 5 minute period. The resulting reaction mixture was stirred for 45 minutes. Hexanes (50 mL) was added, and the mixture was filtered and concentrated in vacuo. The residue was taken up into hexanes (50 mL), washed with 1 M HCl (40 mL), saturated NaCl (40 mL). The organic extracts were dried ($MgSO_4$) and concentrated by rotary evaporation to yield a yellow oil. Purification by flash silica gel chromatography (98:02 hexane/EtOAc) afforded (R)-2-bromo-1-[tert-butyldiphenylsilyloxy]-3-butyne (4) (1.50 g, 97%) as a colorless oil (Note: this material is unstable and should be used immediately): $R_f$ 0.74 (90:10 hexane/EtOAc); IR (neat) 3308, 1437, 1112, 701 cm$^{-1}$; $^1$H NMR ($CDCl_3$) δ 7.70 (m, 4 H), 7.42 (m, 6 H), 4.46 (dt, $J_1$ =6.66 Hz, $J_2$=2.36 Hz, 1 H), 3.91 (ddd, $J_1$=10.7 Hz, $J_2$=6.32, Hz, $J_3$=3.78 Hz, 2H), 2.59 (d, J=2.4 Hz, 2 H), 1.08 (m, 9H); $^{13}$C NMR ($CDCl_3$); δ 135.8, 132.8, 129.6, 127.6, 80.3, 75.6, 67.5, 36.2, 26.8, 19.3.

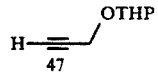

Tetrahydro-2-(2-propynyloxy)-2H-pyran (47). To a stirred solution of propargyl alcohol (5g, 90 mmol) and dihydropyran (37.5 g, 0.44 mol, 5 equiv) in $CH_2Cl_2$ (300 ML), was added p-toluenesufonic acid (30 mg). The mixture was stirred at 20° C. for 1.5 hours. The solvent was removed by rotary evaporation. The residue was taken up in ether (150 mL) and washed with aqueous saturated $NaHCO_3$ (120 mL), saturated NaCl (120 mL), water (200 mL). The organic layer was dried ($MgSO_4$) and concentrated to yield a yellow oil. Purification by distillation under reduced pressure gave Tetrahydro-2-(2-propynyloxy)-2H-pyran (47) (12 g, 97%) as a colorless oil: bp: (40° C., 0.05 mm Hg).

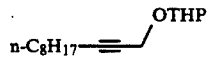

Tetrahydro-2-(2-undecynyloxy)-2H-pyran. A solution of tetrahydro-2-(2-propynyloxy)-2H-pyran (47) (2.8 g, 20 mmol) in THF (30 mL) was cooled to −78° C. and n-BuLi (2.5 M, 8 mL) was added over 15 minutes. The mixture was stirred for 30 minutes at which time octyl bromide (4.24 g, 2.2 mmol, 1.1 equiv) in THF (10 mL) was added. The reaction mixture was then stirred at −78° C. for 1 hour, allowed to warm to 0° C. and stirred for an additional 30 minutes. The reaction mixture was quenched with NH4Cl (10 mL) and poured into ether (150 mL) and water (150 mL). The organic layer was separated, dried (MgSO4) and concentrated by rotary evaporation to yield a yellow oil used in the next step without purification.

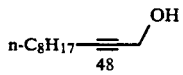

2-Undecyn-1-ol (48). To a solution of tetrahydro-2-(2-undecynyloxy)-2H-pyran in methanol (100 mL), was added p-toluenesulfonic acid (30 mg). The mixture was stirred at room temperature for 4 hours. The solvent was removed by rotary evaporation. The residue was taken up in ether (150 mL) and washed with aqueous saturated NaHCO3 (120 mL), saturated NaCl (120 mL) and water (200 mL). The organic layer was dried (MgSO4) and concentrated to yield a yellow oil. Purification by flash silica gel chromatography (90:10 hexane/EtOAc) afforded 2-undecyn-1-ol (48) (2.6 g, 77% overall) as a colorless oil: $R_f$ 0.27 (90:10 hexane/EtOAc); IR (neat) 3300, 2925, 2855, 1437, 1110 Cm$^{-1}$; $^1$H NMR (CDCl3) δ 4.18 (t, J=2.4 Hz, 2 H), 2.8 (s, 1 H), 2.14 (tt, $J_1$=7.2 Hz, $J_2$=2.4 Hz, 2 H), 1.35 (m, 12 H), 0.82 (t, J=6.9 Hz, 3 H); $^{13}$C NMR (CDCl3) δ 86.15, 78.28, 50.93, 31.76, 29.09, 29.04, 28.82, 28.56, 22.56, 18.63, 13.95.

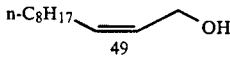

cis-2-Undecen-1-ol (49). To a solution of 2-Undecyn-1-ol (48) (0.5 g, 3 mmol) in EtOAc (10 mL) was added Lindlar catalyst (25 mg). Hydrogen was bubbled through the reaction mixture. After 2 hours, the reaction was judged complete by TLC (90:10 EtOAc/Petroleum ether, $R_f$(13)=0.61, $R_f$(14)=0.55). The reaction mixture was filtered and the filtrate was concentrated by rotary evaporation to yield cis-2-Undecen-1-ol (14) as a colorless oil: $^1$H NMR (CDCl3) δ 5.60 (m, 2 H), 4.21 (s, 2 H), 2.14 (m, 2 H), 1.35 (m, 12 H), 0.82 (t, J=6.9 Hz, 3 H); $^{13}$C NMR (CDCl3) δ 132.98, 128.32, 58.42, 31.85, 29.57, 29.29, 29.19, 27.38, 22.63, 14.04.

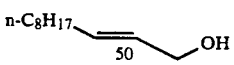

trans-2-Undecen-1-ol (50). To a solution of 2-tridecyn-1-ol (2 g, 10 mmol) in Et2O (50 mL) was added LiAlH4 (1 g, 26 mmol, 2.6 equiv). The resulting mixture was refluxed for 12 hours and allowed to cool to 25° C. A saturated solution of sodium-potassium tartrate was then added and the resulting mixture was stirred for an additional 3 hours. The organic layer was separated, dried (MgSO2) and concentrated by rotary evaporation to yield trans-2-tridecen-1-ol (50) as a colorless oil: $^1$H NMR (CDCl3) δ 5.62 (dt, $J_1$=15.3 Hz, $J_2$=5.1 Hz, 1 H), 5.70 (dt, $J_1$=15.3 Hz, $J_2$=5.7 Hz, 1 H), 4.08 (t, J=4.2 Hz, 2 H), 2.04 (q, J=6 Hz, 2 H), 1 30 (m, 16 H), 0.88 (t, J=6.9 Hz, 3 H); $^{13}$C NMR (CDCl3) δ 133.72, 128.92, 63.96, 32.31, 32.01, 29.72, 29.60, 29.43, 29.28, 29.24, 22.78, 14.20.

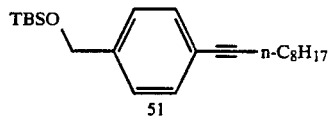

1-(tert-Butyldimethylsilyoxymethyl)-4-(2-decynyl)-benzene (51). To a solution of 1; -nonyne (150 mg, 1.2 mmol) in THF (5 mL) at −78° C., was added n-BuLi (0.47 mL, 1.19 mmol). The resulting mixture was stirred for 30 minutes and a solution of [(tertButyldimethylsilyl)oxymethyl]-4-iodomethyl benzene (40) (361 mg, 2 mmol) in THF (1 mL) was added. The reaction mixture was then stirred at −78° C. for 1 hour, allowed to warm to 0° C. and stirred for an additional 30 minutes. At this time, water (2 mL) was slowly added and the mixture was poured into water (50 mL) and Et2O (50 mL). The organic layer was separated, dried (MgSO4) and concentrated in vacuo to yield a yellow oil. Purification by flash silica gel chromatography (95:05 hexane/EtOAc) afforded (51) (313 mg, 87%) as a colorless oil: $R_f$ 0.85 (95:05 hexane/EtOAc); $^1$H NMR (CDCl3) δ 7.34 (d, J=8.7 Hz, 2 H), 7.29 (d, J=7.8 Hz, 2 H), 4.75 (s, 2 H), 3.59 (t, J=2.4 Hz, 2 H), 2.24 (tt, $J_1$=7.2 Hz, $J_2$=2.4 Hz, 2 H), 1.55 (m, 2 H), 1.42 (m, 2 H), 1.32 (m, 6 H), 0.97 (s, 9 H), 0.92 (t, J=6.9 Hz, 3 H), 0.12 (s, 6 H); $^{13}$C NMR (CDCl3) δ 139.68, 136,38, 127.83, 126.32, 82.74, 77.76, 64.93, 31.91, 29.18, 29.98, 26.08, 24.97, 22.77, 18.97, 14.23, −5.11.

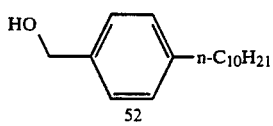

4-Decylphenylmethanol (52). To a solution of 1-(tert-butyldimethylsilyoxymethyl)-4-(2-decynyl)benzene (51) (313 mg, 0.87 mmol) in CH:CN (10 mL) was added 50% aqueous HF (1 mL), the mixture was stirred at room temperature for 15 minutes. The reaction mixture was poured in saturated NaHCO3 (50 mL) and ether (75 mL). The organic layer was separated and washed with two 50-mL portions of water, dried (MgSO4) and concentrated to yield the alcohol derivative. The latter was dissolved in EtOAc (10 mL) and 5% Pd/C was added. Hydrogen was then bubbled through the reaction mixture for 2 hours. The reaction mixture was filtered and the filtrate was concentrated in vacuo to yield 4-decylphenylmethanol (52) is a clear oil; $^1$H NMR (CDCl3) δ7.28 (d, J=7.8 Hz, 2 H), 7.18 (d, J=8.1 Hz, 2 H), 4.65 (s, 2 H), 2.61 (t, J=7.8 Hz, 2 H), 1.83 (s, 1 H), 1.61 (m, 2 H), 1.25 (m, 16 H), 0.90 (t, J=6.9 Hz, 3 H); $^{13}$C NMR (CDCl3) δ 142.68, 138.25, 128.76, 127.27, 65.41, 35.80, 32.04, 31.69, 29.65, 29.75, 29.46, 26.06, 22.83, 14.27.

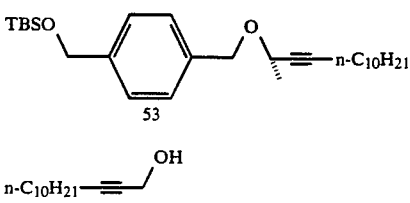

(S)-(−)-3-Tetradecyn-2-ol (7). Racemate 7 (700 mg), was added to a suspension of Amano P30 enzyme (175 mg) in isopropenyl acetate (12 mL). The resulting mixture was stirred at 40° C. for 41h. At this time the conversion was 50% by $^1$H NMR. The mixture was then filtered over silica gel and the solvent was removed by rotary evaporation. The enzymatically produced (R)-acetate and unreacted (S)-alcohol were separated by chromatography on silica gel. Alcohol (−)-7 (348 mg, 49%, ee >95%) was obtained as a clear oil: $[\alpha]^{25}_D$-16.2° (c 1.10, CHCl$_3$); $^1$H NMR (CDCl$_3$) δ 4.48 (s, 1 H), 2.16 (m, 2 H), 1.39 (m, 19 H), 0.85 (t, J=6.9 Hz, 3 H); $^{13}$C NMR (CDCl$_3$) δ 84.57, 82.19, 58.44, 31.85, 29.49, 29.27, 29.08, 28.81, 28.60, 24.66, 22.63, 18.58, 14.04.

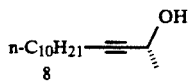

(R)-(+)-3-Tetradecyn-2-ol (8). The acetate isolated from the previous enzymatic reaction (376 mg) was dissolved in MeOH (2 mL). Potassium carbonate (50 mg) was added and the resulting mixture was stirred at 25° C. for 1 hour. After the usual treatment, purification by silica gel chromatography afforded (+)-8 (345 mg, 48%, ee>95%) as a clear oil; $[\alpha]^{25}_D$+15.8° (c 1.05, CHCl$_3$); $^1$H NMR (CDCl$_3$) δ 4.48 (s, 1 H), 2.16 (m, 2 H), 1.39 (m, 19 H), 085 (t, J=6.9 Hz, 3 H); $^{13}$C NMR (CDCl$_3$) δ 84.57, 82.19, 58.44, 31.85, 29.49, 29.27, 29.08, 28.81, 28.60, 24.66, 22.63, 18.58, 14.04.

1-[tert-Butyldimethylsilyloxy)methyl]-4-[(1,1-dimethyl-2-tridecynyloxy)methyl]benzene (53): Method A: colorless oil; $^1$H NMR (CDCl$_3$) δ 7.38 (d, J=8.1 Hz, 2 H), 7.33 (d, J=8.1 Hz, 2 H), 4.78 (s, 2 H), 4.66 (s, 2 H), 2.67 (t, J=6.9 Hz, 2 H), 1.56 (s, 6 H), 1.33 (m, 16 H), 1.00 (s, 9 H), 0.94 (m, 3 H), 0.15 (s, 6 H); $^{13}$C NMR (CDCl$_3$) δ 140.39, 138 04, 127.62, 125.97, 84.74, 82.48, 70.74, 66.16, 64.86, 31.94, 29.60, 29.31, 29.16, 28.84, 25.96, 22.71, 18.63, 18.39, 14.13.

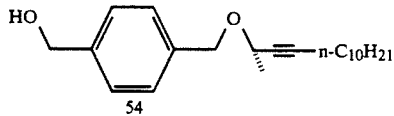

4-[(1,1-Dimethyl-2=tridecynyloxy)methyl]phenylmethanol (54). To a solution of (53) (914 mg, 2 mmol) in THF (15 mL), was added tetrabutylammonium fluoride (3 mmol, 1.5 equiv). The resulting mixture was stirred for 1 hour. The mixture was diluted with ether (100 mL) and washed with water (100 mL). The organic extract was dried (MgSO$_4$) and concentrated by rotary evaporation to yield (54) as a yellow oil: $^1$H NMR (CDCl$_3$) δ 7.37 (d, J=8.1 Hz, 2 H), 7.29 (d, J=8.1 Hz, 2 H), 4.62 (s, 2 H), 4.59 (s, 2 H), 2.31 (s, 1 H), 2.22 (t, J =6.9 Hz, 2 H), 1.52 (s, 6 H), 1.28 (m, 16 H), 0.89 (t, J=6.9 Hz, 3 H); $^{13}$C NMR (CDCl$_3$) δ 139.98, 138.65, 127.89, 12687, 84.89, 82.35, 70.87, 66.06, 64.91, 31.89, 29.55, 29.24, 29.10, 28.78, 22.67, 18.59, 14.10.

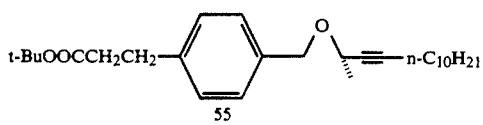

tert-Butyl 3-[4-[(1,1-Dimethyl-2-tridecynyl oxy)methyl]phenyl]propanoate (55) colorless oil; $^1$H NMR (CDCl$_3$) δ 7.29 (d, J=8.1 Hz, 2 H), 7.17 (d, J=8.1 Hz, 2 H), 4.60 (s, 2 H), 2.90 (t, J=8.1 Hz, 2 H), 2.52 (t, J=7.5 Hz, 2 H), 2.22 (t, J=6.9 Hz, 2 H), 1.51 (s, 6 3 H); $^{13}$C NMR (CDCl$_3$) δ 172.40, 139.94, 137.32, 128.35, 128.07, 84.93, 82.59, 80.40, 70.86, 66.22, 37.29, 32.03, 30.96, 29.69, 29.42, 29.24, 28.93, 28.20, 22 80, 18.74, 14.23.

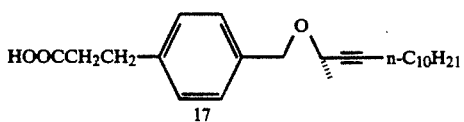

3-[4-[(1,1-Dimethyl-2-tridecynyloxy)methyl]phenyl]propanoic Acid (17). To a solution of (55) (442 mg, 1 mmol) in MeOH (20 mL), was added LiOH (10 equiv). The resulting mixture was refluxed for 12 hours and then allowed to cool to 25° C. The reaction mixture was poured into a saturated solution of NH$_4$Cl (50 mL) and Et$_2$O (70 mL). The organic layer was separated, dried (MgSO$_4$) and concentrated by rotary evaporation to yield 17) (349 mg, 90%) as a yellow oil; $^1$H NMR (CDCl$_3$) δ 9.00 (s, 1 H), 7.30 (d, J=7.8 Hz, 2H), 7.18 (d, J=7.8 Hz, 2 H), 4.60 (s, 2 H), 2.94 (t, J=7.8 Hz, 2 H), 2.66 (t, J=7.5 Hz, 2 H), 2.23 (t, J=6.9 Hz, 2 H), 1.52 (s, 6 H), 1.28 (m, 16 H), 0.89 (t, J=6.9 Hz, 3 H); $^{13}$; C NMR (CDCl$_3$) δ 179.25, 139.24, 137.31, 128.17, 128.08, 84.85, 82.37, 70.79, 6.06, 35.89, 31.89, 30.36, 29.55, 29.32, 29.24, 29.11, 28.82, 28.78, 22.68, 18.60, 14.13.

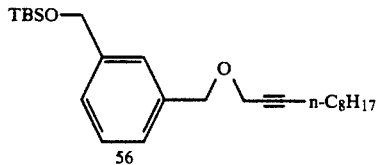

1-[tert-Butyldimethyl-silyoxy)methyl]-3-[(2-undecynyloxy)methyl]benzene (56): Method A: colorless oil; $^1$H NMR (CDCl$_3$) δ 7.30 (m, 4 H), 4.76 (s, 2 H), 4.60 (s, 2 H), 4.16 (t, J=2.1 Hz, 2 H), 2.26 (tt, J$_1$=6.9 Hz, J$_2$=2.1 Hz, 2 H), 1.4 (m, 12 H), 0.97 (s, 9 H), 0.91 (t, J=6.6 Hz, 3 H), 0.11 (s, 6 H); $^{13}$C NMR (CDCl$_3$) δ 139.57, 138.62, 129.05, 128.32, 127.65, 87.72, 75.85, 71.08, 64.77, 57.54, 31.98, 29.34, 29.24, 29.04, 28.76, 22.80, 18.93, 14.24, 5.63.

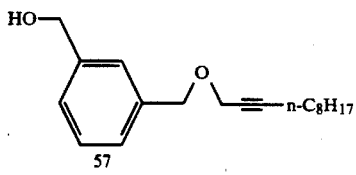

3-[(2-Undecynyloxy)methyl]phenylmethanol (57): colorless oil; $^1$H NMR (CDCl$_3$) δ 7.30 (m, 4 H), 4.69 (d, J=5.7 Hz, 2 H), 4.59 (s, 2 H), 4.17 (t, 2.1 Hz, 2 H), 2.24 (tt, J$_1$=7.2 Hz, J$_2$=2.1 Hz, 2 H), 1.86 (t, J=5.7 Hz, 1 H), 1.4 (m, 12 H), 0.90 (t, J=6.6 Hz, 3 H); $^{13}$C NMR (CDCl$_3$) δ 141.24, 139.19, 128.80, 127.49, 126.75, 126.53, 87.64, 75.81, 71.53, 65.34, 58.03, 31.97, 29.03, 29.23, 29.33, 28.76, 22.77, 18.92, 14.24.

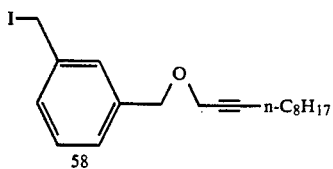

1-Iodomethyl-3-(2-Undecynyloxymethyl)benzene (58): yellow oil; $^1$H NMR (CDCl$_3$) δ 7.30 (m, 4 H), 4.57 (s, 2 H), 4.46 (s, 2 H), 4.18 (t, J=2.1 Hz, 2 H), 2.25 (tt, J$_1$=7.2 Hz, J$_2$=2.1 Hz, 2 H), 1.4 (m, 12 H), 0.89 (t, J=6.9 Hz, 3 H); $^{13}$C NMR (CDCl$_3$) δ 139.57, 139.61, 129.05, 128.32, 127.65, 87.72, 75.75, 71.06, 58.11, 31.98, 29.34, 29.24, 29.03, 28.76, 22.79, 18.92, 14.24, 5.62.

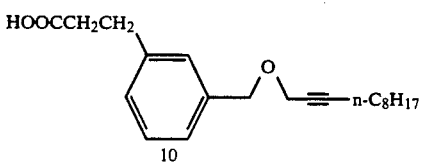

3-[3=(2-Undecynyloxymethyl)phenyl]propanoic Acid (lo): colorless oil; 3200 (s), 2928, 2856, 1710, 1457, 1437, 1078 (s), 3057, 3028 cm$^{-1}$; $^1$H NMR (CDCl$_3$) δ 7.30 (m, 4 H), 4.57 (s, 2 H), 4.17 (t, J=2 Hz, 2 H), 2.97 (t, J=7.55 Hz, 2 H), 2.69 (t, J=7.55 Hz, 2 H), 2.24 (tt, J$_1$=6.92 Hz, J$_2$=2.01 Hz, 2H), 1.4 (m, 12 H), 0.88 (t, J=6.9 Hz, 3 H); $^{13}$C NMR (CDCl$_3$) δ 178.80, 140.36, 137.98, 128.62, 127.95, 127.69, 126.15, 87.57, 75.84, 71.24, 57.82, 35.43, 31.80, 30.50, 29.17, 29.07, 28.88, 28.62, 22.63, 18.77, 14.07; HRMS calcd for C$_{21}$H$_{30}$O$_3$ (M+) 330.2195, found 330.2199.

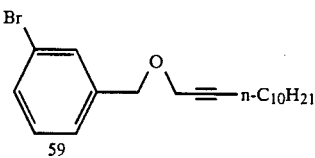

1-Bromo-3-(2-tridecynyloxymethyl)benzene (59): Method B: colorless oil; $^1$H NMR (CDCl$_3$) δ 7.36 (m, 4 H), 4.56 (s, 2 H), 4.18 (t, J=2.1 Hz, 2 H), 2.24 (tt, J$_1$=6.9 Hz, J$_2$=2.1 Hz, 2 H), 1.4 (m, 16 H), 0.88 (t, J=6.9 Hz, 3 H); $^{13}$C NMR (CDCl$_3$) δ 141.00, 131.07, 130.92, 130.06, 126.53, 121.05, 87.65, 75.60, 70.55, 58.15, 32.023, 29.70, 29.45, 29.27, 29.03, 28.735, 22.80, 18.90, 14.24.

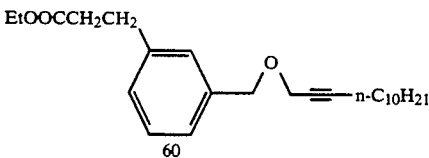

Ethyl 3-[(2-Tridecynyloxymethyl)phenyl]Propanoate (60): colorless oil; $^1$H NMR (CDCl$_3$) δ 7.21 (m, 4 H), 4.56 (s, 2 H), 4.16 (t, J=2.1 Hz, 2 H), 4.13 (q, J=7.2 Hz, 2 H), 2.95 (t, J=8.1 Hz, 2 H), 2.62 (t, J=8.1 Hz, 2 H), 2.24 (tt, J$_1$=7.2 Hz, J$_2$=2.1 Hz, 2 H), 1.4 (m, 19 H), 0.88 (t, J=6.9 Hz, 3 H); $^{13}$C NMR (CDCl$_3$) δ 173.03, 138.06, 128.66, 128.14, 127.86, 126.15, 87.51, 75.90, 71.43, 60.53, 57.96, 36.02, 32.00, 31.00, 29.66, 29.43, 29.26, 29.02, 28.77, 22.79, 18.91, 14.31, 14.21.

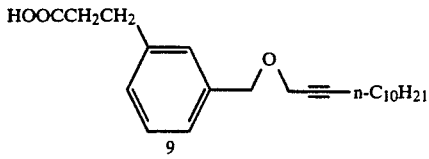

3-[3-(2-Tridecynyloxymethyl)phenyl]propanoic Acid (9: oil; IR (neat) 3200 (s), 2928, 2856, 1710, 1457, 1437, 1078 (s), 3057, 3028 cm$^{-1}$; $^1$H NMR (CDCl$_3$) δ 9.50 (s, 1 H), 7.21 (m, 4 H), 4.57 (s, 2 H), 4.17 (t, J=2.1 Hz, 2 H), 2.97 (t, J=8.1 Hz, 2 H), 2.62 (t, J=8.1 Hz, 2 H), 2.24 (tt, J=6.9 Hz, J:=2.1 Hz, 2 H), 1.4 (m, 19H), 0.88 (t, J=6.9 Hz, 3 H); $^{13}$C NMR (CDCl$_3$) δ 188.13, 140.48, 138.16, 128.76, 128.10, 127.82, 126.31, 87.57, 75.84, 71.38, 57.97, 35.58, 32.01, 30.62, 29.70, 29.44, 29.02, 28.76, 22.80, 18.92, 14.21; HRMS calcd for C$_{23}$H$_{34}$O$_3$ M+) 358.2507, found 358.2513.

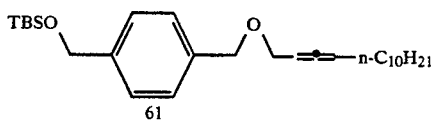

(S)-1-(tert-Butyldimethylsilyloxymethyl)-4(2,3-Tetradecadienyloxymethyl)benzene (61): Method A: colorless oil; $^1$H NMR (CDCl$_3$) δ 7.3 (s, 4 H), 5.23 (m, 2 H), 4.75 (s, 2 H), 4.53 (s, 2H), 4.04 (dd, J$_1$=6.3 Hz, J$_2$ 2.4 Hz, 2 H), 2.03 (m, 2 H), 1.27 (m, 16 H), 0.95 (s, 9 H), 0.89 (t, J=6.9 Hz, 3 H), 0.10 (s, 6H); $^{13}$C NMR (CDCl$_3$) δ 205.21, 140.98, 137.01, 127.95, 126.22, 92.07, 88.46, 71.57, 68.68, 64.93, 32.04, 29.64, 29.76, 29.58, 29.26, 29.21, 28.71, 26.06, 22.80, 18.536, 14.241, −5.13.

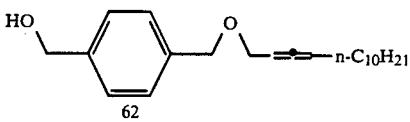

(S)-4- (2,3-Tetradecadienyloxymethyl) phenylmethanol (62): colorless oil; $^1$H NMR (CDCl$_3$) δ 7.2 (s, 4 H), 5.23 (m, 2 H), 4.68 (s, 2 H), 4.53 (s, 2 H), 4.04 (dd, J$_1$=6 Hz, J:=2.7 Hz, 2 H), 2.03 (m, 2 H), 1.8 (s, 1 H), 1.27 (m, 16 H), 0.88 (t, J=6.9 Hz, 3 H); $^{13}$C NMR (CDCl$_3$) δ 205.26, 140.41, 137.86, 128.22, 127.18, 92.13, 88.37, 71.41, 68.78, 65.25, 32.038, 29.75, 29.58, 29.46, 29.26, 29.21, 28.76, 22.813, 14.24.

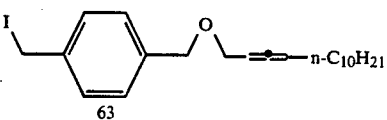

(S)-1-Iodomethyl-4-(2,3-tetradecadienyloxymethyl)benzene (63): yellow oil; $^1$H NMR (CDCl$_3$) δ 7.29 (d, J=8.1 Hz, 2 H), 7.36 (d, J=8.1 Hz, 2 H), 5.23 (m, 2 H), 4.50 (s, 2 H), 4.46 (s, 2 H), 4.04 (dd, J$_1$=6 Hz, J$_2$=3 Hz, 2 H), 2.02 (m, 2 H), 1.27 (m, 16 H), 0.89 (t, J=6.9 Hz, 2 H); $^{13}$C NMR (CDCl$_3$) δ 205.28, 138.71, 138.30, 128.92, 128.36, 92.16, 88.34, 71.27, 68.93, 32.04, 29.75, 29.58, 29.47, 29.21, 29.25, 28.70, 22.82, 14.27, 5.62.

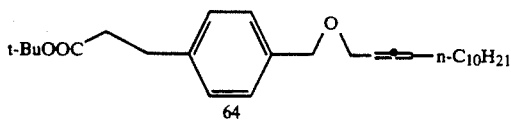

(S)-tert-Butyl 3-[4-(2,3-Tetradecadienyloxymethyl)-phenyl]propanoate (64): yellow oil [α]$^{23}$D +5.08° (c 1.18, CHCl$_3$); IR (neat) 3029, 2924, 2854, 1968, 1728, 1454, 1370, 1300, 1370, 1259, 1145, 1082, 850, 814 cm$^{-1}$; $^1$H NMR (CDCl$_3$) δ 7.27 (d, J=8.1 Hz, 2 H), 7.18 (d, J=8.1 Hz, 2 H), 5.22 (m, 2 H}, 4.50 (s, 2 H), 4.03 (dd, J$_1$=6.3 Hz, J$_2$=3.6 Hz, 2 H), 2.91 (t, J=8.1 Hz, 2 H}, 2.52 (t, J=8.1 Hz, 2 H), 2.02 (m, 2 H), 1.42 (s, 9 H), 1.27 (m, 16 H), 0.89 (t, J=7.2 Hz, 3 H); $^{13}$C NMR (CDCl$_3$) δ 205.22, 172.33, 140.33, 136.21, 128.47, 128.15, 92.04, 88.49, 80.40, 71.52, 68.70, 37.18, 32.05, 30.45, 29.59, 29.47, 29.76, 29.26, 29.21, 28.71, 22.82, 14.25.

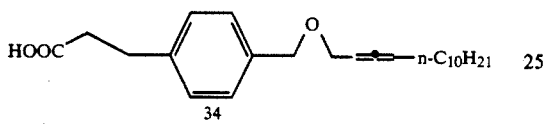

(S)-(+)-3-[4-(2,3-Tetradecadienyloxymethyl)-phenyl]propanoic Acid ((+)-34): colorless oil; [α]$^{23}$D +5.40° (c 1.074, CHC$_3$l); IR (neat) 3100, 3019, 2924, 2852, 1964, 1714, 1517, 1457, 1416, 1088, 909, 826, 736 cm$^{-1}$; $^1$H NMR (CDCl$_3$) δ 11.05 (s, 1 H), 7.29 (d, J=8.1 Hz, 2 H), 7.20 (d, J=8.1 Hz, 2 H), 5.23 (m, 2 H), 4.52 (s, 2 H), 4.05 (dd, J$_1$=6.0 Hz, J$_2$=2.7 Hz, H), 2.96 (t, J=7.5 Hz, 2 H), 2.69 (t, J=7.5 Hz, 2 H), 2.03 (m, 2 H), 1.27 (m, 16 H), 0.90 (t, J=6.9 Hz, 3 H); $^{13}$C NMR (CDCl$_3$) δ 205.29, 179.06, 139.76, 136.44, 128.44, 128.36, 92.10, 88.40, 71.45, 68.76, 37.18, 32.05, 30.45, 29.59, 29.47, 29.76, 29.26, 29.21, 28.71, 22.82, 14.25; HRMS calcd for C$_{24}$H$_{34}$O$_3$(M+) 372.2664, (M+-CH$_2$CH$_2$COOH) 299.2374, found 299.2369.

(R)-3-[4-(2,3-Tetradecadienyloxymethyl). The synthesis, isolation, and purification were performed as described above for compound (+)-34: [α]$^{23}$D −3.80° (c 1.010, CHCl$_3$); IR, $^1$H NMR, $^{13}$C NMR, MS were all identical with those of (+)-34 above.

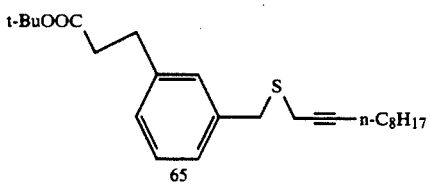

tert-Butyl 3-[3-(2-undecynylthiomethyl)phenyl]propanoate (65): Method A: colorless oil; $^1$H NMR (CDCl$_3$) δ 7.20 (m, 4 H), 3.82 (s, 2 H), 3.07 (t, J=2.4 Hz, 2 H), 2.88 (t, J=7.8 Hz, 2 H), 2.52 (t, J=7.8 Hz, 2 H), 2.20 (m, 2 H), 1.40 (s, 9H), 1.27 (m, 12 H), 0.89 (t, J=7.2 Hz, 2 H); $^{13}$C NMR (CDCl$_3$) δ 172.09, 141.00, 137.91, 128.86, 128.44, 127.01, 126.75, 83.87, 80.24, 75.45, 36.92, 35.24, 31.80, 30.96, 29.16, 29.07, 28.87, 28.02, 22.60, 19.17, 18.81, 14.05.

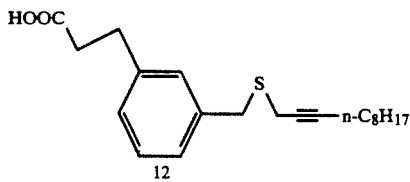

3-[3-(2-Undecynylthiomethyl)phenyl]propanoic Acid (12): colorless oil; IR (neat) 3100, 2953, 2923, 2853, 1709, 1607, 1589, 1297, 1240, 1222 cm$^{-1}$; $^1$H NMR (CDCl$_3$) δ 7.18 (m, 2 H), 3.81 (s, 2 H), 3.08 (t, J=2.1 Hz, 2 H), 2.95 (t, J=7.8 Hz, 2 H), 2.68 (t, J=7.8 Hz, 2 H), 2.23 (tt, J$_1$=6.9 Hz, J$_2$=2.1 Hz, 2 H), 1.27 (m, 12 H), 0.89 (t, J=7.2 Hz, 2 H); $^{13}$C NMR (CDCl$_3$) δ 178.76, 140.44, 138.22, 128.89, 128.72, 127.10, 126.99, 84.07, 75.46, 35.52, 35.24, 31.87, 30.52, 29.25, 29.16, 28.97, 28.93, 22.69, 19.23, 18.89, 14.13; HRMS calcd for C$_{21}$H$_{30}$O$_2$S (M+) 346.1966, found 346.1971.

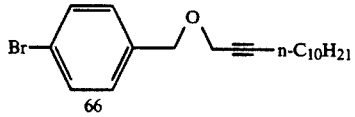

1-Bromo-4-(2-tridecynyloxymethyl)benzene (66): Method B: colorless oil; $^1$H NMR (CDCl$_3$) δ 7.46 (d, J=8.4 Hz, 2 H), 7.23 (d, J=8.4 Hz, 2 H), 4.53 (s, 2 H), 4.15 (t, J=2.1 Hz, 2 H), 2.23 (tt, J$_1$=7.2 Hz, J$_2$=2.1 Hz, 2H), 1.40 (m, 16 H), 0.88 (t, J=6.9 Hz, 2 H); $^{13}$C NMR (CDCl$_3$) δ 136.74, 131.44, 129.59, 121.57, 87.60, 75.50, 70.45, 57.84, 31.86, 29.53, 29.30, 29.10, 28.86, 28.59, 22.65, 18.74, 14.10; HRMS calcd for C$_{20}$H$_{29}$OBr (M+) 364.1402, found 364.1408.

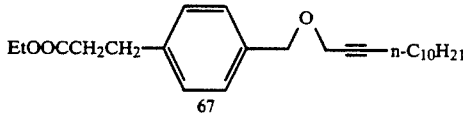

Ethyl 3-[4-(2-Tridecynyloxymethyl) phenyl]-propanoate (67): colorless oil; $^1$H NMR (CDCl$_3$)δ 7.28 (d, J=7.8 Hz, 2 H), 7.19 (d, J=7.8 Hz, 2 H), 4.55 (s, 2 H), 4.14 (m, 4 H), 2.95 (t, J=8.1 Hz, 2 H), 2.60 (t, J=8.1 Hz, 2 H), 2.23 (m, 2 H), 1.27 (m, 19 H), 0.88 (t, J=6.6 Hz, 2 H); $^{13}$C NMR (CDCl$_3$) δ 173.03, 140.14, 135.54, 128.32, 87.15, 75.90, 71.04, 60.39, 57.63, 35.88, 31.85, 30.64, 29.52, 29.30, 29.11, 28.86, 28.60, 22.65, 18.76, 14.16, 14.09; HRMS calcd for C$_{25}$H$_{38}$O$_3$(M+) 386.2821, found 386.2826.

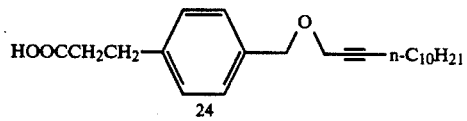

3-[4-(2-Tridecynyloxymethyl)phenyl]propanoic Acid (z4): colorless oil; $^1$H NMR (CDCl$_3$) δ 10.50 (s, 1 H), 7.30 (d, J=8.1 Hz, 2 H), 7.19 (d, J=8.1 Hz, 2 H), 4.56 (s, 2 H), 4.15 (t, J=1.8 Hz, 2 H), 2.96 (t, J=7.8 Hz, 2 H), 2.68 (t, J=7.8 Hz, 2 H), 2.23 (tt, J$_1$7.2 Hz, J$_2$=2.1 Hz, 2 H), 1.27 (m, 16 H), 0.88 (t, J=6.9 Hz, 2 H); $^{13}$C NMR (CDCl$_3$) δ 178.86, 139.88, 135.88, 128.59, 128.45, 87.52, 75.90, 71.16, 57.81, 35.66, 32.02, 30.41, 29.89, 29.44, 29.27, 29.02, 28.77, 22.80, 18.91, 14.24; HRMS calcd for C$_{23}$H$_{34}$O$_3$ (M+) 358.2507, found 358.2511.

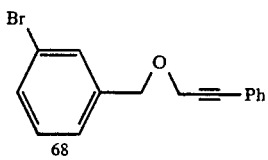

1-Bromo-3-(Propynylphenyloxymethyl)benzene (68): Method B: colorless oil; $^1$H NMR (CDCl$_3$) δ 7.40 (m, 9H), 4.67 (s, 2 H), 4.45 (s, 2 H); $^{13}$C NMR (CDCl$_3$) δ 140.01, 132.10, 132.05, 130.01, 129.05, 128.02, 127.12, 125.10, 85.12, 87.15, 71.16, 58.18.

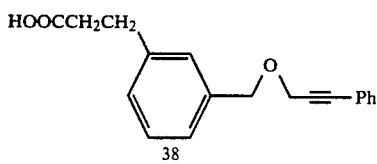

3[3-Phenyl-2-propynyloxymethyl)phenyl]propanoic Acid (3s): colorless oil; $^1$H NMR (CDCl$_3$) δ 7.35 (m, 9 H), 4.69 (s, 2 H), 4.44 (s, 2 H), 3.00 (t, J = 8.1 Hz, 2 H), 2.71 (t, J=8.1 Hz, 2 H), $^{13}$C NMR (CDCl$_3$) δ 179.42, 140.61, 137.92, 131.98, 128.89, 128.69, 128.24, 128.03, 126.42, 122.80, 86.757, 85.166, 71.76, 58.149, 35.73, 30.63; HRMS calcd for C$_{19}$H$_{18}$O$_3$ (M+) 294.1255, found 294.1258.

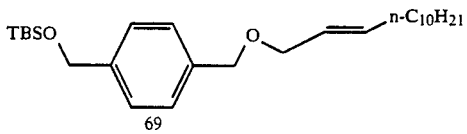

trans-1-(tert-Butyldimethylsilyloxymethyl)-4-(2-tridecenyloxymethyl)benzene (69): Method A: colorless oil; $^1$H NMR (CDCl$_3$) δ 7.35 (s, 4 H), 5.74 (tt, J$_1$=5.3 Hz, J$_2$=6.6 Hz, 1 H), 5.61 (tt, J$_1$=15.3 Hz, J$_2$=6.0 Hz, 1 H), 4.77 (s, 2 H), 4.51 (s, 2 H), 2.08 (q, J=6.6 Hz, 2 H), 1.30 (s, 16 H), 0.98 (s, 9 H), 0.91 (t, J=6 Hz, 3 H), 0.13 (s, 6 H); $^{13}$C NMR (CDCl$_3$) δ 140.91, 137.24, 135.15, 127.91, 126.36, 126.21, 71.80, 70.97, 64.96, 32.47, 32.06, 29.77, 29.65, 29.50, 29.36, 29.24, 26.09, 22.83, 18.54, 14.26, −5.10.

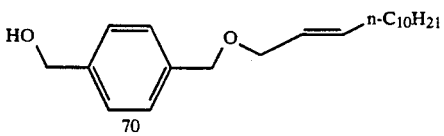

trans-1-(2-Tridecenyloxymethyl)phenylmethanol (70): yellow oil; $^1$H NMR (CDCl$_3$) δ 7.35 (s, 4 H), 5.72 (tt, J$_1$=15.3 Hz, J$_2$=6.6 Hz, 1 H), 5.58 (tt, J$_1$=15.3 Hz, J$_2$=6.0 Hz, 1 H), 4.61 (s, 2 H), 4.48 (s, 2 H), 2.54 (s, 1 H), 2.06 (q, J=6.6 Hz, 2 H), 1.28 (m, 16 H), 0.89 (t, J=6.9 Hz, 3 H); $^{13}$C NMR (CDCl$_3$) δ 140.51, 138.81, 135.39, 128.13, 127.12, 126.16, 71.63, 71.03, 64.97, 32.45, 32.04, 29.63, 29.47, 29.35, 29.22, 22.81, 14.24.

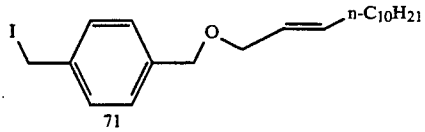

trans-1-Iodomethyl-4-(2-tridecenyloxymethyl)benzene (71): yellow oil; $^1$H NMR (CDCl$_3$) δ 7.35 (d, J=8.1 Hz, 2 H), 7.27 (d, J=8.1 Hz, 2 H), 5.73 (tt, J$_1$=15.3 Hz, J$_2$=6.6 Hz, 1 H), 5.58 (tt, J$_1$=15.3 Hz, J$_2$=6.0 Hz, 1 H), 4.45 (s, 2 H), 4.44 (s, 2 H), 3.84 (d, J=6.3 Hz, 2 H), 2.06 (q, J=6.6 Hz, 2 H), 1.27 (m, 16 H), 0.89 (t, J=6.9 Hz, 3 H); $^{13}$C NMR (CDCl$_3$) δ 138.51, 135.359, 134.56, 130.42, 128.92, 128.30, 126.17, 71.50, 71.23, 32.47, 32.06, 29.76, 29.64, 29.49, 29.35, 29.22, 22.83, 14.30, 5.70.

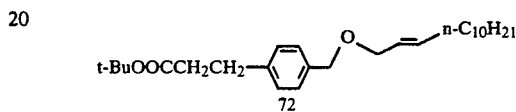

tert-butyl trans-3-[4-(2-Tridecenyloxymethyl)-phenyl]propanoate (72): yellow oil; $^1$H NMR (CDCl$_3$) δ 7.26 (d, J=7.8 Hz, 2 H), 7.18 (d, J=7.8 Hz, 2 H), 5.71 (tt, J$_1$=15.3 Hz, J$_2$=6.6 Hz, 1 H), 5.59 (tt, J$_1$=15.3 Hz, J$_2$=6.0 Hz, 1 H), 4.46 (s, 2 H), 3.82 (d, J=6 Hz, 2 H), 2.90 (t, J=8.1 Hz, 2 H), 2.53 (t, J=8.1 Hz, 2 H), 2.05 (q, J=6.6 Hz, 2 H), 1.42 (s, 9 H), 1.27 (m, 16 H), 0.89 (t, J=6.9 Hz, 3 H); $^{13}$C NMR (CDCl$_3$) δ 172.38, 140.27, 136.38, 135.19, 128.46, 128.13, 126.31, 80.43, 71.75, 70.99, 37.20, 32.44, 32.03, 30.94, 29.74, 29.62, 29.47, 29.33, 29.24, 28.18, 22.80, 14.24.

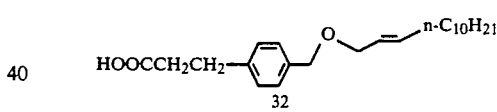

trans-3-[4-(2-Tridecenyloxymethyl)phenyl]propanoic Acid. (32): yellow oil; $^1$H NMR (CDCl$_3$) δ 9.05 (s, 1 H), 7.27 (d, J=7.8 Hz, 2 H), 7.19 (d, J=7.8 Hz, 2 H), 5.72 (tt, J$_1$=15.3 Hz, J$_2$=6.3 Hz, 1 H), 5.58 (tt, J$_1$=15.3 Hz, J$_2$=6.0 Hz, 1 H), 4.47 (s, 2 H), 3.96 (d, J=5.7 Hz, 2 H), 2.95 (t, J=7.8 Hz, 2 H), 2.66 (t, J=7.8 Hz, 2 H), 2.05 (m, 2 H), 1.27 (m, 16 H), 0.88 (t, J=6.3 Hz, 3 H); $^{13}$C NMR (CDCl$_3$) δ 178.79, 139.49, 136.42, 135.21, 128.24, 128.13, 126.00, 71.49, 70.89, 35.58, 32.30, 31.88, 30.27, 29.59, 29.47, 29.32, 29.18, 29.06, 22.66, 14.09; HRMS calcd for C$_{23}$H$_{36}$O$_3$ (M+) 360.2664, found 360.2658.

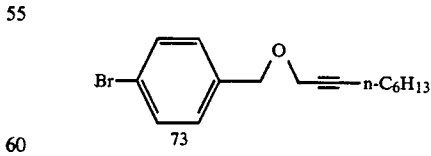

1-Bromo-4-(2-nonynyloxymethyl)benzene (73): Method B: colorless oil; $^1$H NMR (CDCl$_3$) δ 7.46 (d, J=8.4 Hz, 2 H), 7.22 (d, J=8.4 Hz, 2 H), 4.53 (s, 2 H), 4.15 (t, J=1.8 Hz, 2 H), 2.23 (tt, J$_1$=6.9 Hz, J$_2$=2.1 Hz, 2 H), 1.35 (m, 10 H), 0.89 (t, J=6.9 Hz, 3 H); $^{13}$C NMR (CDCl$_3$) δ 136.74, 131.43, 129.60, 121.57, 87.57, 75.51, 70.44, 57.84, 31.30, 28.54, 22.53, 18.75, 14.03.

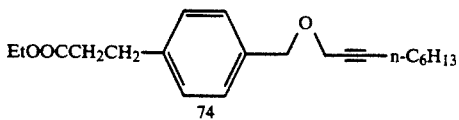

Ethyl 3-[4-(2-Nonynyloxymethyl)phenyl]propanoate (74): colorless oil; $^1$H NMR (CDCl$_3$) δ 7.28 (d, J=7.8 Hz, 2 H), 7.22 (d, J=8.1 Hz, 2 H), 4.55 (s, 2 H), 4.13 (m, 4 H), 2.94 (t, J=8.1 Hz, 2 H), 2.60 (t, J=8.1 Hz, 2 H), 2.23 (tt, J$_1$=7.2 Hz, J$_2$=2.1 Hz, 2 H) 1.4 (m, 10 H), 0.89 (t, J=6.9 Hz, 2 H); $^{13}$C NMR (CDCl$_3$) δ 172.95, 140.30, 135.77, 128.47, 87.40, 75.96, 60.50, 57.76, 36.02, 31.44, 30.78, 28.69, 22.66, 18.89, 14.30, 14.15.

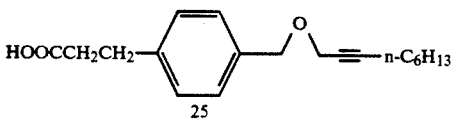

3-[4-(2-Nonynyloxymethyl)phenyl]propanoic Acid (25): colorless oil; $^1$H NMR (CDCl$_3$) δ 7.30 (d, J=7.8 Hz 2 H), 7.20 (d, J=8.1 Hz, 2 H), 4.57 (s, 2 H), 4.16 (t, J=2.1 Hz, 2 H), 2.96 (t, J=7.8 Hz, 2 H), 2.68 (t, J=7.8 Hz, 2 H), 2.25 (tt, J$_1$=7.2 Hz, J$_2$=2.1 Hz, 2 H), 1.4, (m, 10 H), 0.91 (t, J=6.9 Hz, 3 H); $^{13}$C NMR (CDCl$_3$) δ 179.18, 139.92, 135.87, 128.59, 128.45, 87.53, 75.90, 71.14, 57.78, 35.71, 31.45, 30.41, 28.68, 28.72, 22.67, 18.91 14.16; HRMS calcd for C$_{19}$H$_{26}$O$_3$ (M+) 302.1881, found 302.1887.

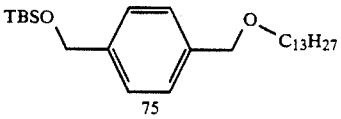

1-(tert-Butyldi-methylsilyloxymethyl)-4-(tridecyloxymethyl)benzene (75): colorless oil; $^1$H NMR (CDCl$_3$) δ 7.17 (s, 4 H), 4.76 (s, 2 H), 4.51 (s, 2 H), 3.47 (t, J=6.6 Hz, 2 H), 1.63 (q, J=6.6 Hz, 2 H), 1.28 (m, 20 H), 0.97 (m, 9 H), 0.91 (m, 3 H), 0.12 (s, 6 H); $^{13}$C NMR (CDCl$_3$) δ 140.85, 137.47, 127.73, 126.20, 72.84, 70.55, 64.96, 32.08, 29.93, 29.83, 29.65, 29.52, 26.35, 26.09, 22.84, 14.27, −5.11.

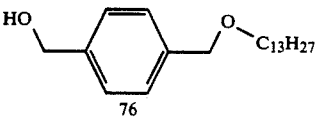

4-(2-Tridecyloxymethyl)phenylmethanol (76): colorless oil; $^1$H NMR (CDCl$_3$) δ 7.34 (s, 4 H), 4.81 (s, 2 H), 4.48 (s, 2 H), 3.44 (t, J=6.6 Hz, 2 H), 2.37 (s, 1 H), 1.6 (m, 2 H), 1.26 (m, 20 H), 0.89 (t, J=6.9 Hz, 3 H); $^{13}$C NMR (CDCl$_3$) δ 140.21, 137.90, 127.80, 126.86, 72.54, 70.49, 64.89, 31.92, 29.67, 29.49, 29.36, 22.16, 22.68, 14.12.

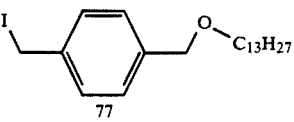

1-Iodomethyl-4-(2-tridecyloxymethyl)benzene (77): yellow oil; $^1$H NMR (CDCl$_3$) δ 7.35 (d, J=8.1 Hz, 2 H), 7.27 (d, J=8.1 Hz, 2 H), 4.46 (s, 2 H), 4.45 (s, 2 H), 3.47 (t, J=6.9 Hz, 2 H), 1.62 (m, 2 H), 1.27 (m, 20 H), 0.90 (t, J=6.9 Hz, 3 H); $^{13}$C NMR (CDCl$_3$) δ 13.55, 138.39, 128.73, 127.96, 72.41, 70.67, 31.94, 29.76, 29.51, 29.39, 29.64, 29.69, 26.20, 22.71, 14.17, 5.57.

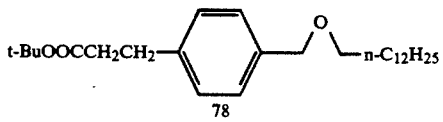

tert-Butyl 3-[4-(2-Tridecyloxymethyl) phenyl]propanoate (78): colorless oil; $^1$H NMR (CDCl$_3$) δ 7.26 (d, J=8.1 Hz, 2 H), 7.18 (d, J=8.1 Hz, 2 H), 4.46 (s, 2 H), 3.45 (t, J=6.9 Hz, 2 H), 2.90 (t, J=7.5 Hz, 2 H), 2.53 (t, J=7.5 Hz, 2 H), 1.60 (m, 2 H), 1.43 (s, 9 H), 1.27 (m, 20 H), 0.89 (t, J - 6.9 Hz, 3 H); $^{13}$C NMR (CDCl$_3$) δ 172.35, 140.18, 136.65, 128.44, 127.94, 80.38, 72.78, 70.56, 37.20, 32.06, 30.95, 29.80, 29.75, 29.50, 28.18, 26.33, 22.82, 12.24.

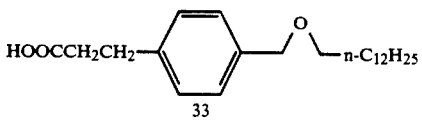

3-[4(Tridecyloxymethyl)phenyl]propanoic Acid (33): white crystals mp 59–60° C.; $^1$H NMR (CDCl$_3$) δ 10.5 (s, 1 H), 7.26 (d, J−8.1 Hz, 2 H), 7.18 (d, J=8.1 Hz, 2 H), 4.46 (s, 2 H), 3.45 (t, J=6.9 Hz, 2 H), 2.90 (t, J=7.5 Hz, 2 H), 2.53 (t, J=7.5 Hz, 2 H), 1.60 (m, 2 H), 1.27 (m, 20 H), 0.89 (t, J=6.9 Hz, 3 H); $^{13}$C NMR (CDCl$_3$) δ 172.35, 140.18, 136.65, 128.44, 127.94, 72.78, 70.56, 37.20, 32.06, 30.95, 29.80, 29.75, 29.50, 28.19, 26.33, 22.82, 12.24; HRMS calcd for C$_{23}$H$_{38}$O$_3$ (M+) 376.2977, found 376.2980.

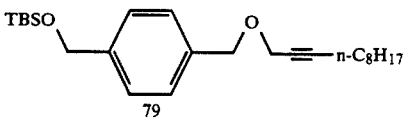

1-(tert-Butyldi-methylsilyloxymethyl)-4-(2-undecynyloxymethyl)benzene (79): colorless oil; $^1$H NMR (CDCl$_3$) δ 7.33 (s, 4 H), 4.76 (s, 2 H), 4.60 (s, 2 H), 4.16 (t, J=2.1 Hz, 2 H), 2.25 (tt, J$_1$=6.9 Hz, J$_2$=2.1 Hz, 2 H), 1.4 (m, 12 H), 0.97 (s, 9 H), 0.91 (t, J =6.6 Hz, 3 H), 0.11 (s, 6 H); $^{13}$C NMR (CDCl$_3$) δ 140.99, 136.25, 128.04, 126.05, 87.21, 75.85, 71.08, 64.77, 57.54, 31.83, 29.34, 29.24, 29.04, 28.76, 22.65, 18.77, 14.09, −5.27.

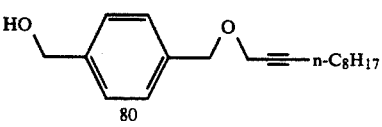

4-(2-Undecynyloxymethyl)phenylmethanol (864p): colorless oil; $^1$H NMR (CDCl$_3$) δ 7.30 (s, 4 H), 4.63 (s, 2 H), 4.59 (s, 2 H), 4.13 (t, J -=1.8 HZ, 2 H), 2.22 (tt, J$_1$=6.9 Hz, J$_2$=1.8 Hz, 2 H), 1.86 (t, J=5.7 Hz, 1 H), 1.4 (m, 12 H), 0.87 (t, J=6.6 Hz, 3 H); $^{13}$C NMR (CDCl$_3$)

δ 140.52, 136.89, 128.26, 126.95, 87.64, 75.81, 71.53, 65.34, 58.03, 31.97, 29.03, 29.23, 29.33, 28.76, 22.77, 18.92, 14.24.

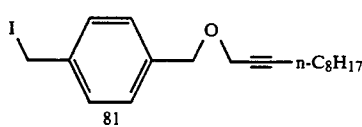

1-Iodomethyl-4-(2-undecynyloxymethyl)benzene (815p): yellow oil; $^1$H NMR (CDCl$_3$) δ 7.26 (d, J=8.1 Hz, 2 H), 7.18 (d, J=8.1 Hz, 2 H), 4.54 (s, 2 H), 4.46 (s, 2 H), 4.18 (t, J=2.1 Hz, 2 H), 2.25 (tt, J$_1$=7.2 Hz, J$_2$=2.1 Hz, 2 H), 1.4 (m, 12 H), 0.89 (t, J=6.9 Hz, 3 H); $^{13}$C NMR (CDCl$_3$) δ 139.57, 139.61, 129.05, 128.32, 127.65, 87.72, 75.75, 71.06, 58.11, 31.98, 29.34, 29.24, 29.03, 28.76, 22.79, 18.92, 14.24, 5.62.

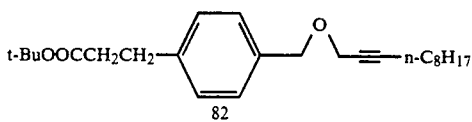

tert-Butyl 3-[4-(2-undecynyloxymethyl) phenyl]propanoate (82): colorless oil; $^1$H NMR (CDCl$_3$) δ 7.26 (d, J=8.1 Hz, 2 H), 7.18 (d, J=8.1 Hz, 2 H), 4.54 (s, 2 H), 4.13 (t, J=1.8 Hz, 2 H), 2.89 (t, J= 8.1 Hz, 2 H), 2.51 (t, J=8.1 Hz, 2 H), 2.23 (tt, J$_1$=6.9 Hz, J$_2$=1.8 Hz, 2 H), 1.4 (m, 12 H), 0.88 (t, J=6.9 Hz, 3 H); $^{13}$C NMR (CDCl$_3$) δ 172.32, 140.50, 135.60, 128.43, 87.37, 80.40, 75.96, 71.19, 57.70, 37.15, 31.96, 30.94, 29.32, 29.23, 29.00, 28.76, 28.13, 28.20, 22.77, 18.90, 14.26, 14.19.

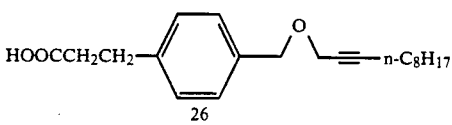

3-[4-(2-Undecynyloxymethyl)phenyl]propanoic Acid (26): colorless oil; IR (neat) 3200 (s), 2928, 2856, 1710, 1457, 1437, 1078 (s), 3057, 3028 cm$^{-1}$; $^1$H NMR (CDCl$_3$) δ 7.26 (d, J=8.1 Hz, 2 H), 7.18 (d, J=8.1 Hz, 2 H) 4.57 (s, 2 H), 4.17 (t, J=2 Hz, 2 H), 2.97 (t, J=7.55 Hz, 2 H), 2.69 (t, J=7.55 Hz, 2 H), 2.24 (tt, J$_1$=6.92 Hz, J$_2$=2.01 Hz, 2 H), 1.4 (m, 12 H), 0.88 (t, J=6.9 Hz, 3 H); $^{13}$C NMR (CDCl$_3$) δ 179.47, 139,76, 135.57, 128.46, 128.30, 87.45, 75.64, 70.97, 57.60, 35.57, 31.82, 30.24, 29.17, 29.07, 28.88, 28.62, 22.63, 18.77, 14.07; HRMS calcd for C$_{21}$H$_{30}$O$_3$ (M+) 330.2194, found 330.2199.

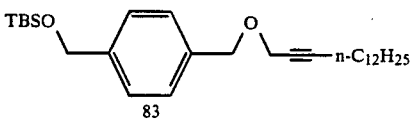

1-(tert-Butyldimethyl-oxymethyl)-4-(2-pentadecynyloxymethyl)benzene (83): colorless oil; $^1$H NMR (CDCl$_3$) δ 7.33 (s, 4 H), 4.76 (s, 2 H), 4.59 (s, 2 H), 4.16 (t, J=2.1 Hz, 2 H), 2.25 (tt, J$_1$=6.9 Hz, J$_2$=2.1 Hz, 2 H), 1.30 (m, 20 H), 0.97 (s, 9 H), 0.91 (t, J =6.9 Hz, 2 H), 0.12 (s, 6 H); $^{13}$C NMR (CDCl$_3$) δ 140.98, 136.25, 128.04, 126.04, 87.21, 75.83, 71.07, 64.76, 57.54, 31.92, 29.57, 29.65, 29.36, 29.15, 28.74, 28.35, 28.39, 28.66, 25.92, 22.68, 18.77, 14.10, −5.27.

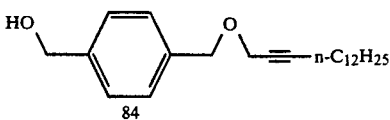

4-(2-Pentadecynyloxymethyl)phenylmethanol (84): colorless oil; $^1$H NMR (CDCl$_3$) δ 7.20 (s, 4 H), 4.61 (s, 2 H), 4.56 (s, 2 H), 4.13 (t, J=2.1 Hz, 2 H), 2.49 (s, 1 H), 2.23 (tt, J$_1$−6.9 Hz, J$_2$=2.1 Hz, 2 H), 1.30 (m, 20 H), 0.91 (t, J=6.9 Hz, 2 H); $^{13}$C NMR (CDCl$_3$) δ 140.55, 136.84, 128.25, 126.95, 87.42, 75.69, 70.96, 64.79, 57.62, 31.88, 29.63, 29.54, 29.33, 29.12, 28.88, 28.62, 22.66, 18.75, 14.09.

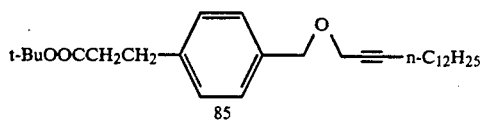

tert-Butyl 3-[4-(2-Pentadecynyloxymethyl) phenyl]propanoate (85): yellow oil; $^1$H NMR (CDCl$_3$) δ 7.27 (d, J=8.1 Hz, 2 H), 7.17 (d, J=8.1 Hz, 2 H), 4.54 (s, 2 H), 4.13 (t, J=1.8 Hz, 2 H), 2.89 (t, J=8.1 Hz, 2 H), 2.51 (t, J=8.1 Hz, 2 H), 2.23 (tt, J$_1$=6.9 Hz, J$_2$=1.8 Hz, 2 H), 1.4 (m, 29 H), 0.88 (t, J=6.9 Hz, 3 H); $^{13}$C NMR (CDCl$_3$) δ 172.32, 140.50, 135.60, 128.43, 87.37, 80.40, 75.96, 71.19, 57.70, 37.17, 32.04, 30.94, 29.48, 29.27, 29.02, 28.77, 28.22, 28.15, 22.82, 18.91, 14.22.

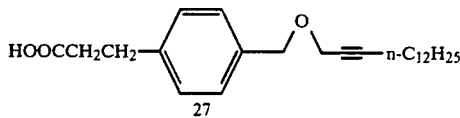

3-[4-(2-Pentadecynyloxymethyl)phenyl]propanoic Acid (27): white crystals mp 47–49° C.; $^1$H NMR (CDCl$_3$) δ 10.5 (s, 1 H), 7.26 (d, J=8.1 Hz, 2 H), 7.18 (d, J=8.1 Hz, 2 H}, 4.56 (s, 2 H), 4.15 (t, J=2.1 Hz, 2 H), 2.95 (t, J=7.5 Hz, 2 H), 2.67 (t, J=7.5 Hz, 2 H), 2.23 (tt, J$_1$=6.9 Hz, J$_2$=2.1 Hz, 2 H), 1.50 (m, 2 H), 1.27 (m, 18 H), 0.89 (t, J=6.9 Hz, 3 H); $^{13}$C NMR (CDCl$_3$) δ 178.81, 139.73, 135.65, 128.43, 128.29, 87.38, 75.68, 71.00, 57.63, 35.53, 31.89, 30.26, 29.62, 29.52, 29.33, 29.12, 28.42, 28.25, 22.66, 18.77, 14.09; HRMS calcd for C$_{25}$H$_{38}$O$_3$ (M+) 386.2821, found 386.2826.

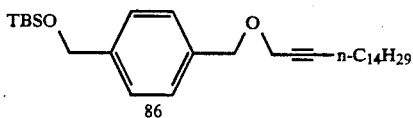

1-(tert-Butyldi-methylsilyloxymethyl)-4-(2-heptadecynyloxymethyl)benzene (86): colorless oil; $^1$H NMR (CDCl$_3$) δ 7.33 (s, 4 H), 4.76 (s, 2 H), 4.59 (s, 2 H), 4.16 (t, J=2.1 Hz, 2 H), 2.25 (tt, J$_1$=6.9 Hz, J$_2$=2.1 Hz, 2 H), 1.30 (m, 24 H), 0.97 (s, 9 H), 0.91 (t, J=6.9 Hz, 2 H), 0.12 (s, 6 H); $^{13}$C NMR (CDCl$_3$) δ 140.98, 136.25, 128.04, 126.04, 87.21, 75.83, 71.07, 64.76, 57.54, 31.92, 29.57, 29.65, 29.36, 29.15, 28.74, 28.35, 28.39, 28.66, 25.92, 22.68, 18.77, 14.10, −5.27.

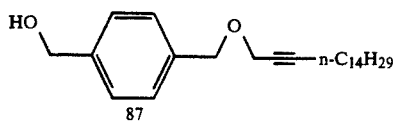

4-(2-Heptadecynyloxymethyl)phenylmethanol (87): colorless oil; $^1$H NMR (CDCl$_3$) δ 7.20 (s, 4 H), 4.61 (s, 2 H), 4.56 (s, 2 H), 4.13 (t, J=2.1 Hz, 2 H), 2.49 (s, 1 H), 2.23 (tt, J$_1$=6.9 Hz, J$_2$=2.1 Hz, 2 H), 1.30 (m, 24 H), 0.91 (t, J=6.9 Hz, 3 H); $^{13}$C NMR (CDCl$_3$) δ 140.54, 136.84, 128.24, 126.95, 87.42, 75.68, 70.96, 64.79, 57.62, 31.91, 29.67, 29.54, 29.35, 29.13, 28.89, 28.63, 28.46, 22.67, 18.76, 14.10.

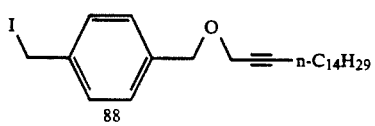

1-Iodomethyl-4-(2-heptadecynyloxymethyl) benzene (58): colorless oil; $^1$H NMR (CDCl$_3$) δ 7.36 (d, J=8.1 Hz, 2 H), 7.29 (d, J=8.1 Hz, 2 H), 4.55 (s, 2 H), 4.45 (s, 2 H), 4.17 (t, J=2.4 Hz, 2 H), 2.24 (tt, J$_1$=7.2 Hz, J$_2$=2.1 Hz, 2 H), 1.40 (m, 24 H), 0.90 (t, J=7.2 Hz, 3 H); $^{13}$C NMR (CDCl$_3$) δ 138.91, 137.74, 128.93, 128.59, 87.63, 75.84, 70.98, 58.01, 32.08, 29.84, 29.71, 29.53, 29.30, 29.05, 28.79, 22.85, 18.94, 14.30, 5.51.

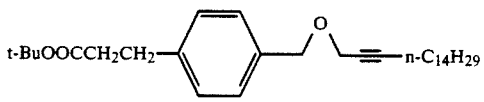

tert-Butyl 3-[4-(2-Heptadecynyloxymethyl) phenyl]-propanoate (89): colorless oil; $^1$H NMR (CDCl$_3$) δ 7.27 (d, J=8.1 Hz, 2 H), 7.17 (d, J=8.1 Hz, 2 H), 4.54 (s, 2 H), 4.13 (t, J=1.8 Hz, 2 H), 2.89 (t, J=8.1 Hz, 2 H), 2.51 (t, J=8.1 Hz, 2 H), 2.23 (tt, J$_1$=6.9 Hz, J$_2$=1.8 Hz, 2 H), 1.4 (m, 33 H), 0.88 (t, J=6.9 Hz, 3 H); $^{13}$C NMR (CDCl$_3$) δ 172.14, 140.34, 135.43, 138.30, 128.25, 87.23, 80.25, 75.78, 71.04, 57.56, 37.00, 31.89, 30.79, 29.64, 29.53, 29.33, 29.42, 28.86, 28.62, 22.65, 18.75, 14.09.

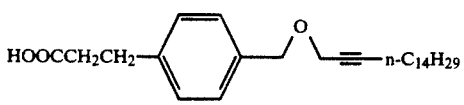

3-[4-(2-Heptadecynyloxymethyl)phenyl]propanoic Acid (2s); white crystals mp 60–61 ° C.; $^1$H NMR (CDCl$_3$) δ 10.5 (s, 1 H), 7.26 (d, J=8.1 Hz, 2 H), 7.18 (d, J=8.1 Hz, 2 H), 4.56 (s, 2 H), 4.15 (t, J=2.1 Hz, 2 H), 2.95 (t, J=7.5 Hz, 2 H), 2.67 (t, J=7.5 Hz, 2 H), 2.23 (tt, J$_1$−6.9 Hz, J$_2$=2.1 Hz, 2 H), 1.50 (m, 2 H), 1.27 (m, 22 H), 0.89 (t J=6.9 Hz, 3 H); $^{13}$C NMR (CDCl$_3$) δ 178.96, 139.70, 135.66, 87.37, 75.69, 71.00, 57.65, 31.90, 30.24, 29.65, 29.54, 29.35, 29.13, 28.88, 28.62, 22.68, 18.77, 14.12.

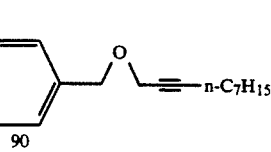

1-Bromo-3-(2-decynyl oxymethyl)benzene (90): Method B: colorless oil; $^1$H NMR (CDCl$_3$) δ 7.40 (m, 4 H), 4.56 (s, 2 H), 4.17 (t, J=2.1 Hz, 2 H), 2.24 (tt, J$_1$=6.9 Hz, J$_2$=2.1 Hz, 2 H), 1.40 (m, 10 H), 0.88 (t, J=6.9 Hz, 3 H); $^{13}$C NMR (CDCl$_3$) δ 141.00, 131.07, 130.92, 130.06, 126.53, 87.50, 75.60, 70.55, 58.15, 32.02, 29.70, 29.44, 29.26, 29.03, 28.73, 22.80, 18.90, 14.24.

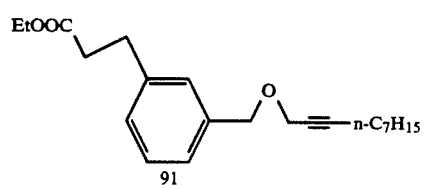

Ethyl 3-[3-(2-Decynyloxymethyl)phenyl]propanoate (91): colorless oil; $^1$H NMR (CDCl$_3$) δ 7.20 (m, 4 H), 4.55 (s, 2 H), 4.15 (t, J=2.1 Hz, 2 H), 4.12 (q, J=7.2 Hz, 2 H), 2.94 (t, J=8.1 Hz, 2 H), 2.61 (t, J=8.1 Hz, 2 H), 2.23 (tt, J$_1$=6.9 Hz, J$_2$=2.1 Hz, 2 H), 1.4 (m, 10 H), 0.87 (t, J=6.9 Hz, 3 H); $^{13}$C NMR (CDCl$_3$) δ 173.05, 140.90, 138.03, 128.68, 128.15, 127.88, 126.16, 87.53, 75.89, 60.55, 57.95, 36.03, 31.86, 31.00, 28.76, 28.96, 22.75, 18.92, 14.31, 14.21.

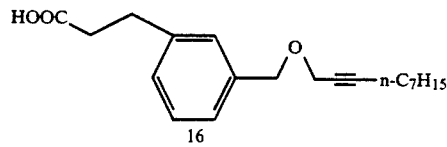

3-[3-(z-Decynyloxymethyl)phenyl]propanoic Acid (16): colorless oil; $^1$H NMR (CDCl$_3$) δ 10.50 (s, 1 H), 7.20 (m, 4 H), 4.57 (s, 2 H), 4.17 (t, J=1.8 Hz, 2 H), 2.96 (t, J=7.8 Hz, 2 H), 2.68 (t, J=7.8 Hz, 2 H), 2.23 (tt, J$_1$=6.9 Hz, J$_2$=1.8 Hz, 2 H), 1.4 (m, 10 H), 0.87 (t, J=6.9 Hz, 3 H); $^{13}$C NMR (CDCl$_3$) δ 178.05, 140.90, 138.03, 128.68, 128.15, 127.88, 126.16, 87.53, 75.89, 71.43, 60.55, 36.03, 31.86, 31.00, 28.76, 28.96, 22.75, 18.92, 14.21.

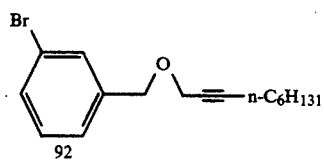

1-Bromo-3-(z-Nonynyloxymethyl)benzene (92): Method B: colorless oil; $^1$H NMR (CDCl$_3$) δ 7.40 (m, 4 H), 4.56 (s, 2 H), 4.17 (t, J=2.1 Hz, 2 H), 2.24 (tt, J$_1$=6.9 Hz, J$_2$=2.1 Hz, 2 H), 1.40 (m, 8 H), 0.88 (t, J=6.9 Hz, 3 H); $^{13}$C NMR (CDCl$_3$) δ 141.00, 131.07, 130.92, 130.06, 126.53, 87.50, 75.60, 70.55, 58.15, 30.62, 28.73, 22.68, 18.90, 14.20.

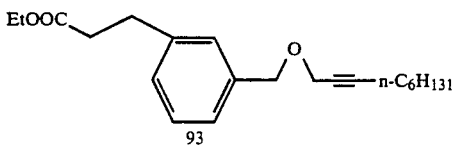

Ethyl 3-[3-(2-Nonynyloxymethyl)phenyl]propanoate (93): colorless oil; $^1$H NMR (CDCl$_3$) δ 7.19 (m, 4 H), 4.54 (s, 2 H), 4.14 (t, J=2.1 Hz, 2 H), 4.12 (q, J=7.2 Hz, 2 H), 2.94 (t, J=8.1 Hz, 2 H), 2.60 (t, J=8.1 Hz, 2 H), 2.23 (tt, J$_1$=6.9 Hz, J$_2$=2.1 Hz, 2 H), 1.40 (m, 8 H), 0.88 (t, J=6.9 Hz, 3 H); $^{13}$C NMR (CDCl$_3$) δ 172.83, 140.72, 137.86, 128.49, 127.97, 127.70, 125.98, 87.33, 75.71, 71.25, 60.38, 57.77, 35.87, 31.30, 30.84, 28.55, 22.54, 18.76, 14.19, 14.03.

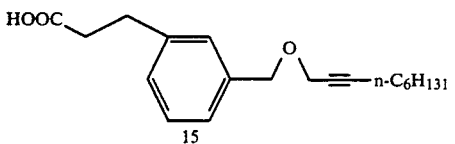

3-[3-(2-Nonynyloxymethyl)phenyl]propanoic Acid (15): colorless oil; $^1$H NMR (CDCl$_3$) δ 9.50 (s, 1 1 H), 7.22 (m, 4 H), 4.57 (s, 2 H), 4.17 (s, 2 H), 2.97 (t, J =8.1 Hz, 2 H), 2.69 (t, J=8.1 Hz, 2 H), 2.25 (m, 2 H), 1.4 (m, 8 H), 0.90 (t, J=7.2 Hz, 3 H); $^{13}$C NMR (CDCl$_3$) δ 179.00, 140.49, 138.11, 128.77, 128.13, 127.85, 126.33, 87.60, 75.84, 71.38, 57.95, 35.66, 31.46, 30.62, 28.75, 22.68, 18.92, 14.19.

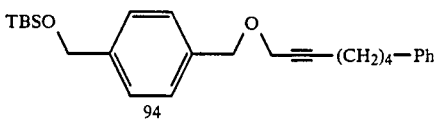

1-(tert-Butyldi-methylsilyloxymethyl)-4-(7-phenyl-2-heptynyloxymethyl) benzene (94): Method A: colorless oil; $^1$H NMR (CDCl$_3$) δ 7.26 (m, 9 H), 4.77 (s, 2 H), 4.60 (s, 2 H), 4.17 (t, J=2.1 Hz, 2 H), 2.67 (t, J=7.5 Hz, 2 H), 2.30 (tt, J$_1$=6.9 Hz, J$_2$=2.1 Hz, 2 H), 1.77 (m, 2 H), 1.60 (m, 2 H), 0.98 (s, 9 H), 0.13 (s, 6 H); $^{13}$C NMR (CDCl$_3$) δ 142.25, 141.04, 136.21, 128.39, 128.30, 128.07, 126.09, 125.73, 86.88, 76.12, 71.16, 64.78, 57.56, 33.40, 30.58, 28.15, 25.97, 18.68, −5.22.

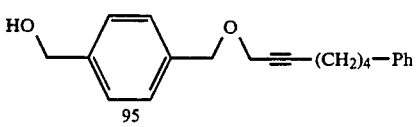

4-(7-Phenyl-2-heptynyloxymethyl)phenylmethanol (95): colorless oil; $^1$H NMR (CDCl$_3$) δ 7.30 (m, 9 H), 4.64 (s, 2 H), 4.61 (s, 2 H), 4.18 (t, J=1.5 Hz, 2 H), 2.68 (t, J=7.8 Hz, 2 H), 2.60 (s, 1 H), 2.32 (tt, J$_1$=7.2 Hz, J$_2$=1.5 Hz, 2 H), 1.77 (m, 2 H), 1.60 (m, 2 H); $^{13}$C NMR (CDCl$_3$) δ 142.44, 140.79, 137.02, 128.49, 128.59, 127.18, 125.95, 87.28, 76.22, 71.24, 64.97, 57.84, 35.56, 30.75, 28.32, 18.85.

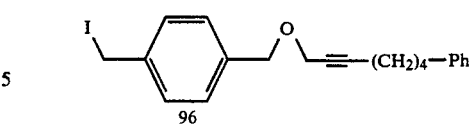

1-Iodomethyl-4-(7-phenyl-2-heptynyloxymethyl)benzene (96): colorless oil; $^1$H NMR (CDCl$_3$) δ 7.31 (m, 9 H), 4.59 (s, 2 H), 4.48 (s, 2 H), 4.21 (t, J =1.5 Hz, 2 H), 2.69 (t, J=7.8 Hz, 2 H), 2.32 (tt, J$_1$=7.2 Hz, J$_2$=1.5 Hz, 2 H), 1.80 (m, 2 H), 1.65 (m, 2 H); $^{13}$C NMR (CDCl$_3$) δ 142.44, 138.95, 137.75, 129.00, 128.61, 128.04, 125.97, 87.31, 76.23, 71.09, 58.08, 35.59, 30.77, 28.33, 18.89, 5.74.

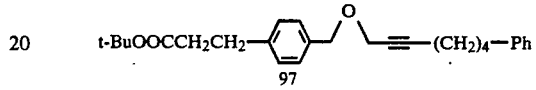

tert-Butyl 3-[4-(7-phenyl-2-heptynyloxymethyl)phenyl]propanoate (97): colorless oil; $^1$H NMR (CDCl$_3$) δ 7.25 (m, 9 H), 4.57 (s, 2 H), 4.16 (t, J=1.8 Hz, 2 H), 2.93 (t, J=8.1 Hz, 2 H), 2.66 (t, J=7.5 Hz, 2 H), 2.55 (t, J=7.5 Hz, 2 H), 2.30 (tt, J$_1$=6.9 Hz, J$_2$=1.8 Hz, 2 H), 1.76 (m, 2 H), 1.60 (m, 2 H); $^{13}$C NMR (CDCl$_3$) δ 172.37, 142.41, 140.56, 135.62, 128.46, 128.54, 125.90, 87.04, 76.29, 71.28, 57.75, 37.20, 35.54, 30.98, 30.71, 28.28, 28.23, 18.82.

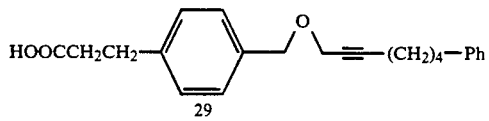

3-[4-(7-Phenyl-2-heptynyloxymethyl)phenyl]propanoic Acid (29): colorless oil; $^1$H NMR (CDCl$_3$) δ 7.25 (m, 9 H), 4.58 (s, 2 H), 4.18 (t, J=1.8 Hz, 2 H), 2.98 (t, J=7.8 Hz, 2 H), 2.68 (m, 4 H), 2.30 (tt, J$_1$=6.9 Hz, J$_2$=1.8 Hz, 2 H), 1.78 (m, 2 H), 1.61 (m, 2H); $^{13}$C NMR (CDCl$_3$) δ 179.12, 142.41, 139.96, 135.85, 128.57, 128.49, 125.92, 87.16, 76.22, 71.22, 57.81, 35.73, 35.54, 30.44, 30.71, 28.29, 18.82; HRMS calcd for C$_{24}$H$_{28}$O$_3$ (M$^+$) 350.1881, found 350.1876.

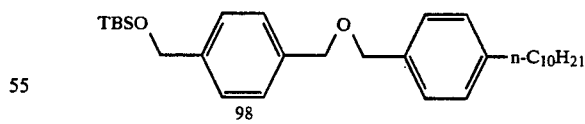

1-(tert-Butyldimethylsilyloxymethyl)-4-[4-(Decylphenylmethyl-oxymethyl]]benzene (98): Method A: colorless oil; $^1$H NMR (CDCl$_3$) δ 7.42 (s, 4 H), 7.36 (d, J=7.8 Hz, 2 H), 7.25 (d, J=7.8 Hz, 2 H), 4.84 (s, 2 H), 4.62 (s, 2 H), 4.60 (s, 2 H), 2.69 (t, J=8.1 Hz, 2 H), 1.70 (m, 2 H), 1.37 (m, 14 H), 1.05 (s, 9 H), 0.98 (t, J=6.9 Hz, 3 H), 0.20 (s, 6 H); $^{13}$C NMR (CDCl$_3$) δ 142.57, 141.03, 137.22, 135.71, 128.65, 128.09, 127.98, 126.31, 72.10, 72.05, 65.02, 35.93, 32.14, 31.76, 29.85, 29.77, 29.57, 26.18, 22.91, 18.62, 14.35, −5.02.

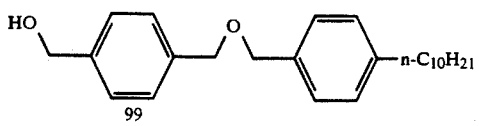

4-[4-(Decylphenylmethyl)oxymethyl]phenylmethanol (99): colorless oil; $^1$H NMR (CDCl$_3$) δ 7.38 (d, J=8.7 Hz, 2 H), 7.34 (d, J=8.7 Hz, 2 H), 7.31 (d, J=7.8 Hz, 2 H), 7.21 (d, J=8.7 Hz, 2 H), 4.64 (s, 2 H), 4.57 (s, 2 H), 4.54 (s, 2 H), 2.64 (t, J =8.1 Hz, 2 H), 2.45 (s, 1 H), 1.65 (m, 2H), 1.32 (m, 14 H), 0.93 (t, J=6.9 Hz, 3 H); $^{13}$C NMR (CDCl$_3$) δ 142.68, 140.57, 137.80, 135.46, 128.65, 128.18, 128.10, 127.21, 72.15, 71.87, 65.05, 35.87, 32.09, 31.71, 29.80, 29.71, 29.51, 22.87, 14.31.

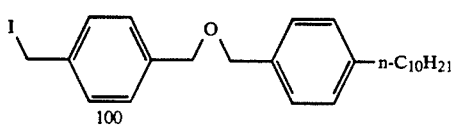

1-Iodomethyl-4-[4-(Decylphenylmethyl) oxymethyl]benzene (100): colorless oil; $^1$H NMR (CDCl$_3$) δ 7.33 (m, 8 H), 4.59 (s, 2H), 4.57 (s, 2 H), 4.50 (s, 2 H), 2.67 (t, J=7.8 Hz, 2 H), 1.68 (m, 2 H), 1.35 (m, 14 H), 0.97 (t, J=6.6 Hz, 3 H); $^{13}$C NMR (CDCl$_3$) δ 142.68, 138.77, 138.47, 135.51, 129.01, 128.68, 128.34, 128.09, 72.41, 71.76, 35.92, 32.14, 31.75, 29.85, 29.76, 29.56, 22.92, 14.39, 5.75.

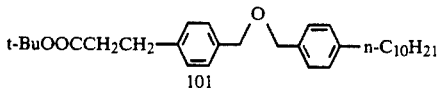

tert-Butyl 3-[4-[4-(Decylphenylmethyl)oxy methyl]phenyl]propanoate (101): colorless oil; $^1$H NMR (CDCl$_3$) δ 7.24 (m, 8 H), 4.55 (s, 2 H), 4.54 (s, 2 H), 2.94 (t, J=8.1 Hz, 2 H), 2.63 (t, J=7.8 Hz, 2 H), 2.57 (t, J=7.5 Hz, 2 H), 1.65 (m, 2 H), 1.46 (s, 9 H), 1.30 (m, 14 H) 0.92 (t, J=6.9 Hz, 3 H); $^{13}$C NMR (CDCl$_3$) δ 172.22, 142.37, 140.16, 136.15, 135.43, 128.42, 128.35, 127.98, 127.87, 80.30, 71.92, 71.79, 37.06, 35.70, 31.91, 31.55, 30.83, 29.62, 29.54, 29.33, 28.06, 22.70, 14.16.

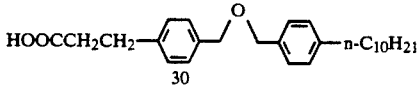

3-[4-[4-(Decylphenylmethyl)oxymethyl]phenyl]propanoic Acid (30): white crystals mp 79–80° C.; $^1$H NMR (CDCl$_3$) δ 7.26 (m, 8 H), 4.55 (s, 4 H), 2.98 (t, J=7.5 Hz, 2 H), 2.70 (t, J=7.8 Hz, 2 H), 2.63 (t, J =7.8 Hz, 2 H), 1.63 (m, 2 H), 1.30 (m, 14 H), 0.92 (t, J=6.6 Hz, 2 H); $^{13}$C NMR (CDCl$_3$) δ 178.95, 142.45, 139.57, 136.38, 135.31, 128.44, 128.30, 128.13, 127.90, 71.97, 71.69, 35.69, 35.60, 35.49, 31.90, 31.53, 30.29, 29.61, 29.52, 29.33, 22.68, 14.12.

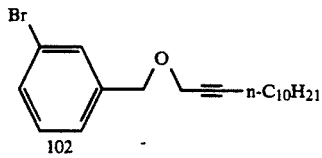

1-Bromo-3-(2-tridecynyloxymethyl)benzene (102): Method B: colorless oil; $^1$H NMR (CDCl$_3$) δ 7.36 (m, 4 H), 4.56 (s, 2 H), 4.18 (t, J=2.1 Hz, 2 H), 2.24 (tt, J$_1$=6.9 Hz, J$_2$=2.1 Hz, 2 H), 1.4 (m, 16 H), 0.88 (t, J=6.9 Hz, 3 H); $^{13}$C NMR (CDCl$_3$) δ 141.00, 131.07, 130.92, 130.06, 126.53, 121.05, 87.65, 75.60, 70.55, 58.15, 32.023, 29.70, 29.45, 29.27, 29.03, 28.735, 22.80, 18.90, 14.24.

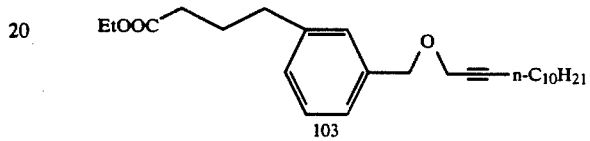

Ethyl 3-[3-(2-tridecynyloxymethyl)phenyl]butyrate (103): colorless oil; $^1$H NMR (CDCl$_3$) δ 7.18 (m, 4 H), 4.55 (s, 2 H), 4.16 (t, J=2.1 Hz, 2 H), 4.12 (q, J=7.2 Hz, 2 H), 2.64 (t, J=7.8 Hz, 2 H), 2.31 (t, J =7.5 Hz, 2 H), 2.33 (tt, J$_1$=7.2 Hz, J$_2$=2.1 Hz, 2 H), 1.95 (q, J=7.8 Hz, 2 H), 1.40 (m, 16 H), 0.87 (t, J=6.9 Hz, 3 H).

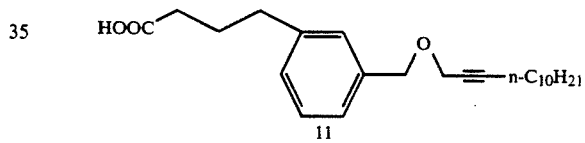

3-[3-(2-Tridecynyloxymethyl)phenyl]butyric Acid (11): colorless oil; $^1$H NMR (CDCl$_3$) δ 9.50 (s, 1 H), 7.20 (m, 4 H), 4.57 (s, 1 H), 4.17 (s, 1 H), 2.68 (t, J=7.8 Hz, 2 H), 2.38 (t, J=7.2 Hz, 2 H), 2.24 (m, 2 H), 1.97 (q, J=7.5 Hz, 2 H), 1.53 (m, 2 H), 1.27 (m, 14 H), 0.88 (t, J=6.9 Hz, 3 H); $^{13}$C NMR (CDCl$_3$) δ 179.44, 141.53, 137.94, 128.62, 128.33, 128.06, 126.03, 87.60, 75.60, 71.47, 57.94, 35.03, 33.38, 32.03, 29.69, 29.45, 29.20, 29.03, 28.77, 26.28, 22.79, 18.92, 14.24.

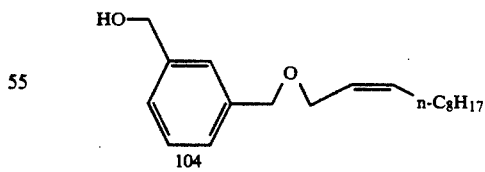

3-(2-Undecynyloxymethyl)phenylmethanol (104): Method A: colorless oil; $^1$H NMR (CDCl$_3$) δ 7.30 (m, 4 H), 5.60 (m, 2 H), 4.63 (s, 2 H), 4.49 (s, 2 H), 4.07 (d, J =5.1 Hz, 2 H), 2.39 (s, 2 H), 2.04 (q, J=6.6 Hz, 2 H), 1.27 (m, 12 H), 0.89 (t, J=6.6 Hz, 2 H); $^{13}$C NMR (CDCl$_3$) δ 140.47, 138.83, 134.27, 128.74, 127.84, 127.65, 126.01, 125.94, 71.88, 65.85, 65.03, 32.03, 29.76, 29.48, 29.37, 27.73, 22.82, 14.24.

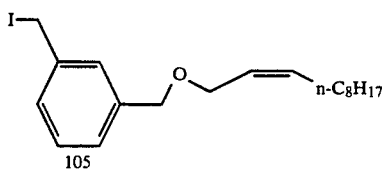

cis-1-Iodomethyl-3-(2-Undecenyloxymethyl) benzene (105): colorless oil; $^1$H NMR (CDCl$_3$) δ 7.30 (m, H), 5.62 (m, 2 H), 4.45 (s, 2 H), 4.40 (s 2 H), 4.05 (d, J=5.1 Hz, 2 H), 2.05 (m, 2 H), 1.37 (m, 12 H), 0.91 (t, J=6.6 Hz, 3 H); $^{13}$C NMR (CDCl$_3$) δ 140.47, 138.83, 134.27, 128.74, 127.84, 127.65, 126.01, 125.94, 71.74, 66.02, 32.06, 29.78, 29.51, 29.38, 27.78, 22.86, 14.30, 5.66.

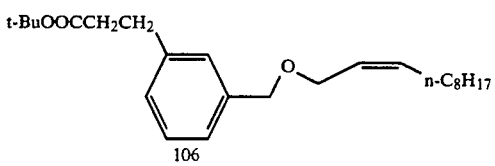

tert-Butyl cis-3-[3-(2-Undecenyloxymethyl) phenyl]-propanoate. (106): colorless oil; $^1$H NMR (CDCl$_3$) δ 7.30 (m, 4 H), 5.59 (m, 2 H), 4.47 (s, 2 H), 4.06 (d, J=4.5 Hz, 2 H), 2.90 (t, J=7.8 Hz, 2 H), 2.53 (t, J =7.8 Hz, 2 H), 2.04 (m, 2 H), 1.42 (s, 9 H), 1.27 (m, 12 H), 0.89 (t, J=6.9 Hz, 3 H); $^{13}$C NMR (CDCl$_3$) δ 172.32, 140.47, 138.83, 134.27, 128.74, 127.84, 127.65, 126.01, 125.94, 80.38, 71.96, 65.78, 37.18, 32.03, 30.95, 29.74, 29.47, 29.36, 28.18, 27.73, 22.79, 14.24.

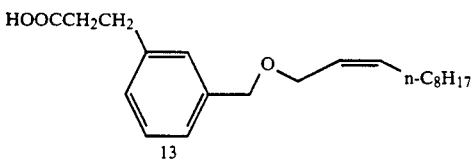

cis-3-[3-(2=Undecenyloxymethyl)phenyl]propanoic Acid (13): colorless oil; $^1$H NMR (CDCl$_3$) δ 7.21 (m, 4 H), 5.61 (m, 2 H), 4.50 (s, 2 H), 4.09 (d, J =5.4 Hz, 2 H), 2.96 (t, J=8.1 Hz, 2 H), 2.68 (t, J=8.4 Hz, 2 H), 2.04 (q, J=6.9 Hz, 2 H), 1.27 (m, 12 H), 0.90 (t, J=6.9 Hz, 3 H); $^{13}$C NMR (CDCl$_3$) δ 178.79, 140.47, 138.83, 134.27, 128.74, 127.84, 127.65, 126.01, 125.94, 72.07, 65.93, 35.67, 32.00, 30.66, 29.67, 29.58, 29.38, 27.74, 22.79, 14.23.

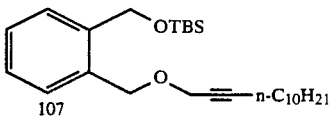

1-(tert-Butyldimethyl silyloxymethyl)-2-(2-tridecynyloxymethyl)benzene (107): colorless oil; $^1$H NMR (CDCl$_3$) δ 7.35 (m, 4 H), 4.85 (s, 2 H), 4.64 (s, 2 H), 4.16 (t, J=2.1 Hz, 2 H), 2.25 (tt, J$_1$=7.2 Hz, J$_2$=1.8 Hz, 2 H), 1.55 (m, 2 H), 1.29 (m, 14 H), 0.97 (s, 9 H), 0.90 (t, J=6.9 Hz, 3 H), 0.12 (s, 6 H); $^{13}$C NMR (CDCl$_3$) δ 140.04, 134.45, 128.88, 128.09, 126.96, 126.91, 87.42, 75.93, 69.05, 62.60, 57.85, 32.02, 29.68, 29.44, 29.28, 29.05, 28.81, 26.07.22.79, 18.93, 14.22, −5.18.

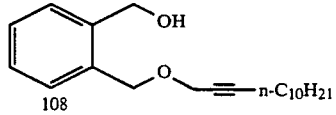

2-(2-Tridecynyloxymethyl)phenylmethanol (108): colorless oil; $^1$H NMR (CDCl$_3$) δ 7.34 (m, 4 H), 4.69 (s, 2 H), 4.18 (t, J=2.1 Hz, 2 H), 2.92 (t, J=6.3 Hz, 1 H), 2.24 (tt, J$_1$=6.9 Hz, J$_2$=2.1 Hz, 2 H), 1.40 (m, 16 H), 0.88 (t, J=6.9 Hz, 3 H); $^{13}$C NMR (CDCl$_3$) δ 140.53, 135.39, 130.18, 129.59, 128.91, 127.89, 88.11, 75.13, 70.20, 63.58, 57.90, 31.86, 29.55, 29.52, 29.29, 29.10, 28.88, 28.57, 22.65, 18.74, 14.08.

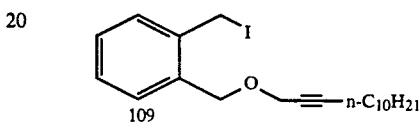

1-Iodomethyl-2-(2-tridecynyloxymethyl)benzene (109): colorless oil; $^1$H NMR (CDCl$_3$) δ 7.28 (m, 4 H), 4.67 (s, 2 H), 4.61 (s, 2H), 4.20 (t, J=2.1 Hz, 2 H), 2.27 (tt, J=6.9 Hz, J$_2$−2.1 Hz, 2 H), 1.40 (m, 16 H), 0.88 (t, J=7.2 Hz, 3 H); $^{13}$C NMR (CDCl$_3$) δ 131.66 131.31, 130.27, 130.22, 128.72, 128.22, 88.11, 75.13, 68.74, 58.11, 31.87, 29.55, 29.29, 29.13, 28.92, 28.64, 22.66, 18.87, 14.07, 3.24.

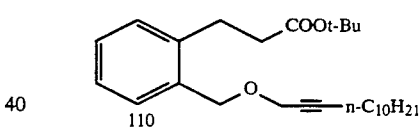

tert-Butyl 3-[2-(2-tridecynyloxymethyl)phenyl]-propanoate (110): colorless oil; $^1$H NMR (CDCl$_3$) δ 7.20 (m, 4 H), 4.55 (s, 2 H), 4.13 (t, J=2.1 Hz, 2 H), 2.90 (m, 4 H), 2.23 (m, 2 H), 1.42 (s, 9 H), 1.24 (m, 16 H), 0.85 (t, J=6.9 Hz, 3 H); $^{13}$C NMR (CDCl$_3$) δ 166.53, 140.21, 135.41, 130.22, 129.52, 128.62, 126.45, 81.97, 75.83, 69.68, 57.97, 50.70, 44.56, 31.99, 29.66, 29.42, 29.25, 29.02, 28.76, 28.04, 26.32, 22.77, 18.86, 14.21.

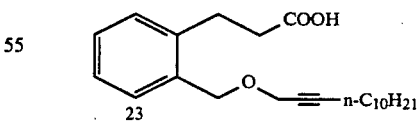

3-[2-(2=Tridecynyloxymethyl)phenyl]propanoic Acid (23): white crystals, mp 48–50° C.; $^1$H NMR (CDCl$_3$) δ 7.24 (m, 4 H), 4.58 (s, 2 H), 4.15 (m, 2 H), 2.95 (m, 2 H), 2.12 (m, 2 H), 1.40 (m, 16 H), 0.85 (t, J=6.9 Hz, 3 H); $^{13}$C NMR (CDCl$_3$) δ 182.31, 139.78, 135.12, 130.33, 129.47, 128.64, 126.45, 87.67, 75.58, 69.68, 57.78, 31.86, 29.55, 29.40, 29.30, 29.12, 28.90, 28.62, 26.18, 22.65, 18.72, 14.09.

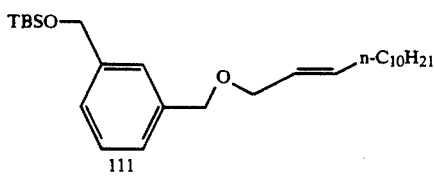

cis-1-(tert-Butyldimethylsilyloxymethyl-3-(2-Tridecenyloxy methyl)benzene (111): Method A: colorless oil; $^1$H NMR (CDCl$_3$) δ 7.35 (m, 4 H), 5.74 (tt, J$_1$=15.3 Hz, J$_2$=6.6 Hz, 1 H), 5.61 (tt, J$_1$=15.3 Hz, J$_2$=6.0 Hz, 1 H), 4.77 (s, 2 H), 4.51 (s, 2 H), 2.08 (q, J=6.6 Hz, 2 H), 1.30 (s, 16 H), 0.98 (s, 9 H), 0.91 (t, J=6 Hz, 3 H), 0.13 (s, 6 H); $^{13}$C NMR (CDCl$_3$) δ 140.91, 138.87, 135.26, 128.65, 127.83, 127.62, 126.23, 125.80, 71.80, 70.97, 64.96, 32.47, 32.06, 29.77, 29.65, 29.50, 29.36, 29.24, 26.09, 22.83, 18.54, 14.26, −5.10.

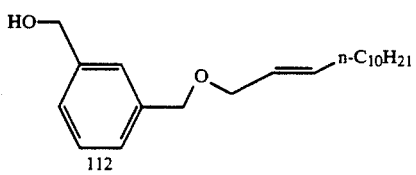

trans-3-(2-Tridecenyloxymethyl)phenylmethanol (112): yellow oil; $^1$H NMR (CDCl$_3$) δ 7.35 (m, 4 H), 5.72 (tt, J$_1$=15.3 Hz, J$_2$=6.6 Hz, 1 H), 5.58 (tt, J$_1$=15.3 Hz, J$_2$=6.0 Hz, 1 H), 4.61 (s, 2 H), 4.48 (s, 2 H), 2.54 (s, 1 H), 2.06 (q, J=6.6 Hz, 2 H), 1.28 (m, 16 H), 0.89 (t, J=6.9 Hz, 3 H); $^{13}$C NMR (CDCl$_3$) δ 140.91, 138.87, 135.26, 128.65, 127.83, 127.62, 126.23, 125.80, 71.63, 71.03, 64.97, 32.45, 32.04, 29.63, 29.47, 29.35, 29.22, 22.81, 14.24.

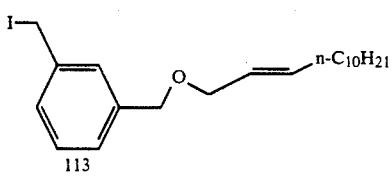

trans-1-Iodomethyl-3-(2-Tridecenyloxymethyl) benzene (113): yellow oil; $^1$H NMR (CDCl$_3$) δ 7.30 (m, 4 H), 5.73 (tt, J$_1$=15.3 Hz, J$_2$=6.6 Hz, 1 H), 5.58 (tt, J$_1$=15.3 Hz, J$_2$=6.0 Hz, 1 H), 4.45 (s, 2 H), 4.44 (s, 2 H), 3.84 (d, J=6.3 Hz, 2 H), 2.06 (q, J=6.6 Hz, 2 H), 1.27 (m, 16 H), 0.89 (t, J=6.9 Hz, 3 H); $^{13}$C NMR (CDCl$_3$) δ 140.91, 138.87, 135.26, 128.65, 127.83, 127.62, 126.23, 125.80, 71.50, 71.23, 32.47, 32.06, 29.76, 29.64, 29.49, 29.35, 29.22, 22.83, 14.30, 5.70.

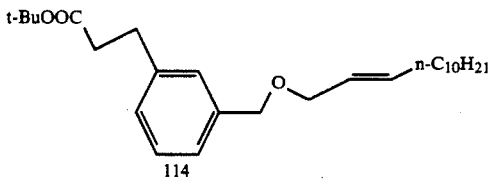

tert-Butyl trans-3-[3-(2-Tridecenyloxymethyl) phenyl]propanoate (114): yellow oil; $^1$H NMR (CDCl$_3$) δ 7.25 (m, 4 H), 5.71 (tt, J$_1$=15.3 Hz, J$_2$=6.6 Hz, 1 H), 5.59 (tt, J$_1$=15.3 Hz, J$_2$=6.0 Hz, 1 H), 4.46 (s, 2 H), 3.96 (d, J=6 Hz, 2 H), 2.88 (m, 4 H), 2.05 (q, J=6.6 Hz, 2 H), 1.42 (s, 9 H), 1.27 (m, 16 H), 0.89 (t, J=6.9 Hz, 3H); $^{13}$C NMR (CDCl$_3$) δ 172.38, 140 91, 138.87, 135.26, 128.65, 127.83, 127.62, 126.23, 125.80, 80.43, 71.75, 70.99, 37.20, 32.44, 32.03, 30.94, 29.74, 29.62, 29.47, 29.33, 29.24, 28.18, 22.80, 14.24.

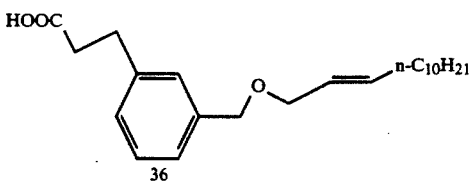

trans-3-[3-(2=Tridecenyloxymethyl)phenyl]-propanoic Acid (36): white crystals, mp 46.5–47.5° C.; $^1$H NMR (CDCl$_3$) δ 9.50 (s, 1 H), 7.18 (m, 4 H), 5.72 (tt, J$_1$=5.3 Hz, J$_2$=6.3 Hz, 1 H), 5.58 (tt, J$_1$=15.3 Hz, J$_2$=6.0 Hz, 1 H), 4.47 (s, 2 H), 3.96 (d, J=5.7 Hz, 2 H), 2.95 (m, 2 H), 2.05 (m, 2 H), 1.27 (m, 16 H), 0.88 (t, J=6.3 Hz, 3 H); $^{13}$C NMR (CDCl$_3$) δ 178.79, 140.91, 138.87, 135.26, 128.65, 127.83, 127.62, 126.23, 125.80, 71.49, 70.89, 35.58, 32.30, 31.88, 30.27, 29.59, 29.47, 29.32, 29.18, 29.06, 22.66, 14.09.

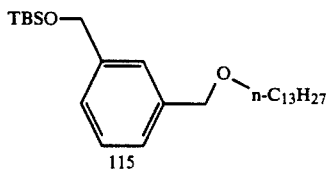

1-(tert-Butyldimethylsilyloxymethyl)-3-(tridecyloxymethyl)benzene (115): Method A: colorless oil; $^1$H NMR (CDCl$_3$) δ 7.27 (s, 4 H), 4.76 (s, 2 H), 4.51 (S, 2 H), 3.47 (t, J=6.6 Hz, 2 H), 1.63 (m, 2 H), 1.28 (m, 20 H), 0.96 (s, 9 H), 0.91 (m, 3 H), 0.12 (s, 6 H); $^{13}$C NMR (CDCl$_3$); δ 140.85, 137.47, 127.73, 126.20, 72.84, 70.55, 64.96, 32.08, 29.93, 29.83, 29.77, 29.65, 29.53, 26.35, 26.09, 22.84, 14.27, −5.11.

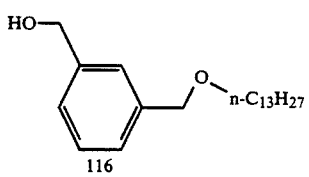

3-(2=Tridecyloxymethyl)phenylmethanol (116): colorless Oil; $^1$H NMR (CDCl$_3$) δ 7.30 (s, 4 H), 4.61 (s, 2 H), 4.48 (s, 2 H), 3.44 (t, J=6.6 Hz, 2 H), 2.37 (s, 1 H), 1.60 (m, 2 H), 1.26 (m, 20 H), 0.89 (t, J=6.9 Hz, 3 H); $^{13}$C NMR (CDCl$_3$) δ 140.21, 137.90, 127.80, 126.96, 72.54, 70.49, 64.89, 31.92, 29.67, 29.49, 29.36, 26.16, 22.68, 14.12.

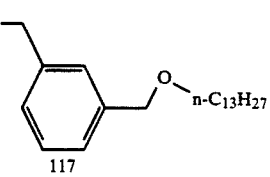

1-Iodomethyl-3-(2-tridecyloxymethyl)benzene (117): colorless oil; $^1$H NMR (CDCl$_3$) δ 7.36 (d, J=8.1 Hz, 2

H), 7.27 (d, J=8.1 Hz, 2 H), 4.46 (s, 2 H), 4.45 (s, 2 H), 3.47 (t, J=6.6 Hz, 2 H), 1.62 (m, 2 H), 1.27 (m, 20 H), 0.90 (t, J=6.9 Hz, 3 H); $^{13}$C NMR (CDCl$_3$) δ 138.5, 138.39, 128.73, 127.96, 72.41, 70.67, 31.94, 29.76, 29.69, 29.51, 29.39, 26.20, 22.71, 14.17, 5.57.

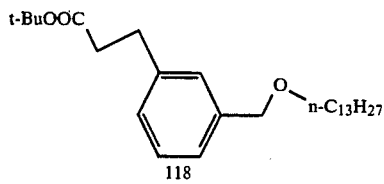

tert-Butyl 3-[3-(2-Tridecyloxymethyl)phenyl]-propanoate (118): colorless oil; $^1$H NMR (CDCl$_3$) δ 7.26 (d, J=8.1 Hz, 2 H), 7.18 (d, J=8.1 Hz, 2 H), 4.46 (s, 2 H), 3.45 (t, J=6.9 Hz, 2 H), 2.90 (t, J=8.1 Hz, 2 H), 2.53 (t, J=8.1 Hz, 2 H), 1.43 (s, 9 H), 1.27 (m, 22 H), 0.89 (t, J=6.9 Hz, 3 H); $^{13}$C NMR (CDCl$_3$) δ 172.35, 140.18, 136.65, 128.44, 127.94, 80.38, 72.78, 70.56, 37.20, 32.06, 30.95, 29.80, 29.75, 29.63, 29.55, 29.50, 28.18, 26.33, 22.82, 14.24.

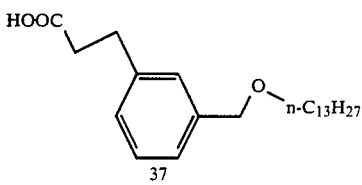

3-[3-(2-Tridecyloxymethyl)phenyl]propanoic Acid (37): colorless oil; $^1$H NMR (CDCl$_3$) δ 9.50 (s, 1 H), 7.26 (d, J=8.1 HZ, 2 H), 7.18 (d, J=8.1 Hz, 2 H), 4.46 (s, 2 H), 3.45 (t, J=6.9 Hz, 2 H), 2.90 (t, J=8.1 Hz, 2 H), 2.53 (t, J=8.1 Hz, 2 H), 1.27 (m, 22 H), 0.89 (t, J=6.9 Hz, 3 H); $^{13}$C NMR (CDCl$_3$) δ 178.40, 140.18, 136.65, 128.44, 127.94, 72.78, 70.56, 37.20, 32.06, 30.95, 29.80, 29.75, 29.63, 29.55, 29.50, 26.33, 22.82, 14.24; HRMS Calcd for C$_{23}$H$_{38}$O$_3$ (M+) 376.2977, found 376.2980.

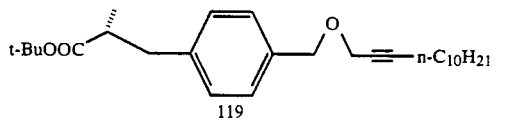

tert-Butyl 2,2-Dimethyl-3-[4-[(2-tridecenyloxy)methyl]phenyl]propanoate (119): Method A: Colorless oil; $^1$H NMR (CDCl$_3$) δ 7.26 (d, J=8.1 Hz, 2 H), 7.14 (d, J=8.1 Hz, 2 H), 4.55 (s, 2 H), 4.15 (t, J=1.8 Hz, 2 H), 2.82 (s, 2 H), 2.24 (tt, J$_1$=7.2 Hz, J$_2$=2.1 Hz, 2 H), 1.44 (s, 9 H), 1.27 (m, 16 H), 1.11 (s, 6 H), 0.88 (t, J=6.9 Hz, 3 H); $^{13}$C NMR (CDCl$_3$) δ 176.94, 137.97, 135.71, 130.48, 127.86, 87.46, 80.17, 75.96, 71.29, 57.81, 45.77, 43.92, 32.02, 29.69, 29.44, 29.27, 29.02, 28.77, 28.12, 25.16, 22.08, 18,91, 14.24.

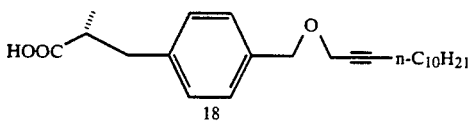

2,2-Dimethyl-3-[4-[(2- tridecynyloxy) methyl]-phenyl]propanoic acid (18): Colorless oil; $^1$H NMR (CDCl$_3$) δ 9.50 (s, 1 H), 7.27 (d, J=7.8 Hz, 2 H), 7.15 (d, J=7.8 Hz, 2 H), 4.56 (s, 2 H), 4.16 (t, J=1.8 Hz, 2 H), 2.89 (s, 2 H), 2.23 (m, 2 H), 1.40 (m, 16 H), 1.20 (s, 6 H), 0.88 (t, J=6.9 Hz, 3 H); $^{13}$C NMR (CDCl$_3$) δ 183.80, 137.06, 135.86, 130.28, 127.86, 87.34, 75.76, 71.10, 57.75, 45.45, 43.31, 31.86, 29.52, 29.29, 29.11, 28.87, 28.62, 24.59, 22.65, 18.77, 14.08.

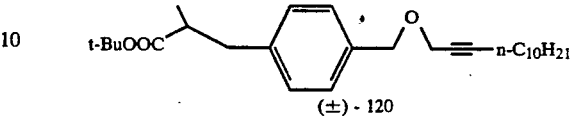

tert-Butyl 2-Methyl-3-[4-[(2-tridecenyloxy) methyl]-phenyl]propanoate (121): Method A: Colorless oil; $^1$H NMR (CDCl$_3$) δ 7.25 (d, J=7.8 Hz, 2 H), 7.14 (d, J=7.5 Hz, 2 H), 4.54 (s, 2 H), 4.12 (s, 2 H), 2.95 (q, J=9.9 Hz, 1 H), 2.60 (q, J=7.5 Hz, 2 H), 2.22 (t, J =6.9 Hz, 2 H), 1.40 (m, 25 H), 1.09 (d, J=6.0 Hz, 3 H), 0.87 (t, J=6.6 Hz, 3 H); $^{13}$C NMR (CDCl$_3$) δ 175.33, 139.22, 135.46, 129.02, 128.07, 87.19, 79.94, 75.80, 71.04, 57.53, 42.19, 39.45, 31.86, 29.52, 29.29, 29.11, 28.85, 28.61, 27.94, 22.63, 18.75, 16.86, 14.07.

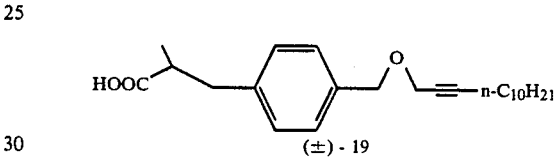

2-Methyl-3-[4-[(2-tridecynyloxy)methyl]phenyl]-propanoic acid (±-19): Colorless oil; $^1$H NMR (CDCl$_3$) δ 11.00 (s, 1 H), 7.29 (d, J=7.8 Hz, 2 H), 7.16 (d, J=7.8 Hz, 2 H), 4.56 (s, 2 H), 4.16 (t, J=1.8 Hz, 2 H), 3.08 (dd, J$_1$=12.9 Hz, J$_2$=5.4 Hz, 1 H), 2.70 (m, 2 H), 1.40 (m, 16 H), 1.17 (d, J=6.6 Hz, 3 H), 0.88 (t, J=5.1 Hz, 3 H); $^{13}$C NMR (CDCl$_3$) δ 182.46, 138.61, 135.72, 129.03, 128.30, 87.37, 75.74, 71.05, 57.69, 41.19, 38.93, 31.88, 29.55, 29.32, 29.14, 28.88, 28.62, 22.67, 18.77, 16.42, 14.11.

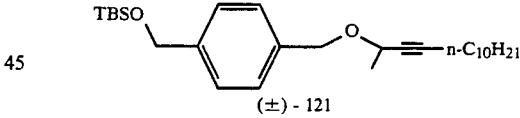

1-(tert-Butyldimethylsilyloxymethyl)-4-(1-methyl-2-tridecynyloxymethyl)benzene [(±)-121]): Method A: Colorless oil; $^1$H NMR (CDCl$_3$) δ 7.36 (d, J=8.4 Hz, 2 H), 7.31 (d, J=8.4 Hz, 2 H), 4.78 (d, J=11.4 Hz, 1 H), 4.76 (s, 2 H), 4.51 (d, J=11.4 Hz, 1 H), 4.21 (m, 1 H), 2.27 (m, 2 H), 1.56 (m, 2 H), 1.46 (d, J=6.6 Hz, 3 H), 1.31 (m, 14 H), 0.98 (s, 9 H), 0.92 (t, J=6.9 Hz, 3 H), 0.13 (s, 6 H); $^{13}$C NMR (CDCl$_3$) δ 140.78, 136.80, 127.95, 126.02, 85.77, 79.99, 70.00, 64.79, 64.46, 31.92, 29.39, 29.35, 29.16, 28.87, 28.76, 25.94, 22.70, 22.51, 18.70, 18.40, 14.13, −5.25.

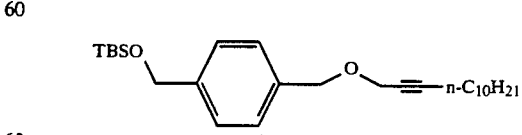

(R)-(+)-1-(tert-Butyldimethylsilyloxymethyl)-4-(1-methyl-2-tridecynyloxymethyl)benzene ([(+)-121]):

All spectral data were identical with those of the previously described racemate: $[\alpha]^{23}D$ +74.1° (c 1.26, CHCl₃).

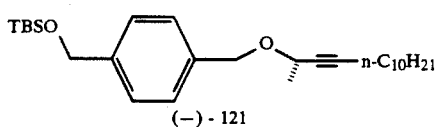

(s)-(−)-1-(tert-Butyldimethylsilyloxymethyl)-4-(1-methyl-2-tridecynyloxymethyl)benzene ([(−)-121]): All spectral data were identical with those of the previously described racemate: $[\alpha]^{23}D$ −75.3° (c 1.36, CHCl₃).

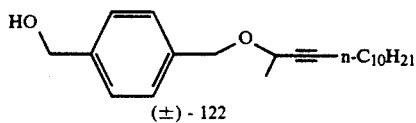

4-(1-Methyl-2-tridecynyloxymethyl)phenyl methanol ([(±)-122]): Colorless oil; ¹H NMR (CDCl₃) δ 7.35 (d, J=8.1 Hz, 2 H), 7.29 (d, J=8.1 Hz, 2 H), 4.76 (d, J=11.7 Hz, 1 H), 4.61 (s, 2 H), 4.48 (d, J=11.7 Hz, 1 H), 4.20 (m, 2 H), 2.50 (s, 1 H), 2.24 (m, 2 H), 1.54 (m, 2 H), 1.43 (d, J=6.6 Hz, 3 H), 1.28 (m, 14 H) 0.89 (t, J=6.9 Hz, 3 H); ¹³C NMR (CDCl₃) δ140.52, 137.62, 128.36, 127.09, 86.11, 80.02, 70.04, 64.97, 64.77, 32.03, 29.70, 29.46, 29.27, 28.87, 22.59, 22.79, 18.81, 14.24.

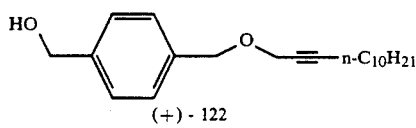

(R)-(+)-4-(1-Methyl-2-tridecynyloxymethyl) phenylmethanol ([(+)-122]): A]) spectral data Were identical with those of the previously described racemate: $[\alpha]^{23}D$ +96.4° (c 1.36, CHCl₃).

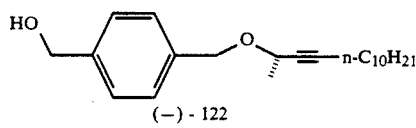

(S)-(−)-4-(1-Methyl-2-tridecynyloxymethyl) phenylmethanol ([(−)-122]): All spectral data were identical with those of the previously described racemate: $[\alpha]^{23}D$ −97.1 ° (c 1.29, CHCl₃).

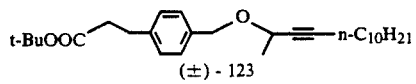

tert-Butyl 3-[4-[(1; -Methyl-2=tridecynyloxy methyl)methyl]phenyl]propanoate ([(±)-123]): Colorless oil; ¹H NMR (CDCl₃) δ 7.28 (d, J=7.8 Hz, 2 H), 7.17 (d, J=7.8 Hz, 2 H), 4.74 (d, J=11.4 Hz, 1 H), 4.46 (d, J=11.4 Hz, 1 H), 4.19 (m, 2 H), 2.90 (t, J=7.8 Hz, 2 H), 2.52 (t, J=7.8 Hz, 2 H), 2.24 (m, 2 H), i.54 (m, 2 H), 1.43 (m, 9 H), i.28 (s, i4 H), 0.89 (t, J=7.2 Hz, 3 H); ¹³C NMR (CDCl₃) δ 172.36, 140.31, 136.18, 128.44, 128.36, 85.93, 80.40, 80.13, 70.11, 64.65, 37.20, 32.02, 30.95, 29.69, 29.44, 29.25, 28.97, 28.86, 28.18, 22.79, 22.62, 18.81, 14.22.

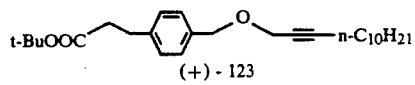

(R)-(+)-tert-Butyl 3-[4-[(1-Methyl-2-tridec ynyloxymethyl)methyl]phenyl]propanoate ([(+)-123]): All spectral data were identical with those of the previously described racemate: $[\alpha]^{23}D$ +77.2° (c 1.14, CHCl₃).

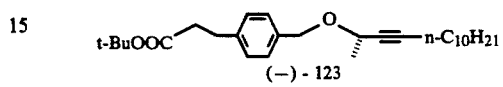

(S)-(−)-tert-Butyl 3-[4-[(1-Methyl-2-tri decynyloxymethyl)methyl]phenyl]propanoate ([(−)-123]): All spectral data were identical with those of the previously described racemate: $[\alpha]^{23}D$ −77.8° (c 11.7, CHCl₃).

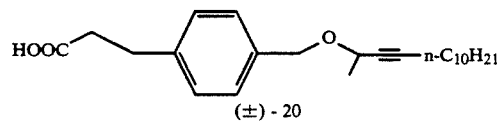

3-[4-[(1-Methyl-2=tridecynyloxy)methyl]phenyl]-propanoic Acid ([(±)-20]): Method A: White crystals: mp 57–59° C.; ¹H NMR (CDCl₃) δ11.00 (s, 1 H), 7.32 (d, J=7.8 Hz, 2 H), 7.20 (d, J=7.8 Hz, 2 H), 4.76 (d, J=18 Hz, 1 H), 4.48 (d, J=18 Hz, 1 H), 4.21 (q, J=6.6 Hz, 1 H), 2.97 (t, J=7.8 Hz, 2 H), 2.68 (t, J=7.8 Hz, 2 H), 2.25 (t, J=6.6 Hz, 2 H), 1.55 (m, 2 H), 1.45 (d, J=6.6 Hz, 3 H), 1.29 (m, 14 H), 0.90 (t, J=6.6 Hz, 3 H); ¹³C NMR (CDCl₃) δ 179.11 139.51, 136.28, 128.34, 128.23, 85.90, 79.92, 69.91, 64.63, 35.62, 31.89, 30.28, 29.56, 29.31, 29.12, 28.85, 28.73, 22.66, 22.47, 18.68, 14.09.

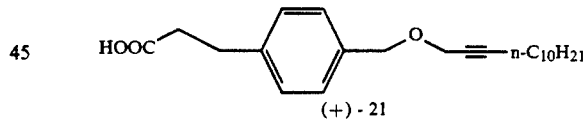

(R)-(+)-3-[4-[(1=Methyl-2-tridecenyloxy) methyl]phenyl]propanoic Acid ((+)-21]): The synthesis, isolation, and purification were performed as described above. Alcohol 8 was used instead of racemate 6. All spectral data were identical with those of the previously described racemate: $[\alpha]^{23}D$ +69.7° (c 1.01, MeOH).

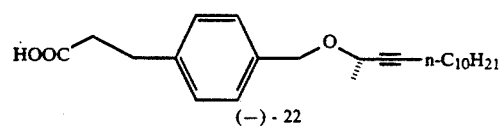

(S)-(−)-3-[4-[(1-Methyl-2-tridecynyloxy) methyl]phenyl]propanoic acid ([(−)-22]): The synthesis, isolation, and purification were performed as described above. Alcohol 7 was used instead of racemate 6. All spectral data were identical with those of the previously described racemate: $[\alpha]^{23}D$ −70.6° (c 1.02, MeOH).

Pharmacological Activity

The compounds of the present invention of the general formula

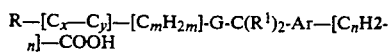

possess an inhibitory activity on 12-lipoxygenase, described before, for example, in standard laboratory tests, the results in the Table I were found. Table I: Inhibition of 12-lipoxygenase activity by aryl aliphatic acids.

| Compound | IC$_{50}$ ($\mu$M) |
| --- | --- |
| 25 | 2.0 |
| 27 | 0.32 |
| 26 | 0.10 |
| 24 | 0.035 |
| 31 | 1.0 |
| 32 | 0.40 |
| 34 | 0.28 |
| 35 | 0.45 |
| 30 | 5.0 |

The standard assay procedure is as follows:

Compounds of the present invention were added in 3 $\mu$L of DMSO at an appropriate concentration to porcine leukocyte cytosol containing 12-lipoxygenase in buffer (final protein concentration of 0.075 mg/ml in 0.1 M HEPES, 2 mM CaCl$_2$, 1 mM MgCl$_2$, pH 8.0) and preincubated for 5 minutes at 37° C. [1-$^{14}$C] Arachidonic acid was added (final concentration of 5 mM) and the reactions were incubated for 15 minutes at 37° C. and terminated by the addition of HCl. Total reaction volume was 100 $\mu$L. Assays also included reduced glutathione in the assay at 25 mM or following the assay at 1 mM and/or cold carrier 12-HETE and arachidonic acid added at the end of the incubation at concentrations of 5 and 100 mM, respectively. Samples were extracted with water-saturated ethyl acetate and the extracts were spotted onto TLC plates. The plates were developed with dichloromethane/ethyl acetate/acetic acid in a ratio of 70:30:1. Under these conditions, the RF's of 12-HETE and arachidonic acid are 0.30 and 0.45, respectively. The percentage conversion to 12-HETE was calculated from the percentage of the total $^{14}$C on the TLC plate that coelutes with a standard of 12-HETE.

Toxicity

Toxicities of the compounds of the present invention were very low, and are therefore, estimated to be safe for pharmaceutical use.

Applications for Pharmaceuticals

Inhibition of 12-lipoxygenase to suppress the production of 12-HETE appears to be useful for prevention and/or treatment of inflammation, immune disease, psoriasis, arteriosclerosis and/or ischaemic cardiovascular diseases and also suppressing metastasis of cancer in animals including humans.

Since the compounds of the present invention possess an inhibitory activity against 12-lipoxygenase in vitro, it is expected to be useful for prevention and/or treatment of the above disease.

For the purposes described above, the compounds of the present invention may normally be administered systemically or parenterally.

The doses to be administered are determined depending upon age, body weight, symptom, the desired therapeutic effect, the route of administration, and the duration of the treatment, etc. In a human adult, the doses per person per administration are generally between 1 mg and 500 mg, by oral administration, up to several times per day, and between 1 mg and 100 mg, by parenteral administration up to several times per day.

Since, the doses to be used depend upon various conditions, as mentioned above, there may be a case in which doses are lower than or greater than the ranges specified above.

Solid compositions for oral administration include compressed tablets, pills, dispersible powders, capsules, and granules. In such compositions, one or more of the active compound(s) is or are, admixed with at least one inert diluent (lactose, mannitol, glucose, hydroxypropyl-cellulose, microcrystalline cellulose, starch, polyvinyl pyrrolidone, magnesium metasilicate alminate, etc.). The compositions may also comprise, as is normal practice, additional substance other than inert diluents: e.g., lubricating agents (magnesium stearate, etc.), disintegrating agents (cellulose calcium glycolate, etc.), and assisting agent for dissolving (glutamic acid, aspartic acid, etc.) stabilizing agent (lactose etc.).

The tablets or pills may, if desired, be coated with gastric or enteric material (sugar, gelatin, hydroxypropyl-cellulose or hydroxypropylmethyl cellulose phthalate, etc.).

Capsules include soft ones and hard ones.

Liquid compositions for oral administration include pharmaceutically-acceptable emulsions, solutions, suspensions, syrups, and elixirs. in such compositions, one or more of the active compound(s) is or are admixed with inert diluent(s) commonly used in the art (purified water, ethanol, etc.). Besides inert diluents, such compositions may also comprise adjuvants (wetting agents, suspending agents, etc.), sweeting agents, flavoring agents, perfuming agents and preserving agents.

Other compositions for oral and nasal administration include spray compositions which may be prepared by known methods and which comprise one or more of the active compound(s).

Spray compositions may comprise additional substances other than inert diluents; e.g. preserving agents (sodium sulfite, etc.), isotonic buffer (sodium chloride, sodium citrate, citric acid, etc.).

For preparation of such spray compositions, for example, the method described in the U.S. Pat. Nos. 2,868,691 or 3,095,355 may be used.

Injections for parenteral administration include sterile aqueous or non-aqueous solution, suspensions and emulsions. In such compositions, one or more of active compound(s) is or are admixed with at least one inert aqueous diluent(s) (distilled water for injection, physiological salt solution, etc.) or inert non-aqueous diluent(s) (propylene glycol, polyethylene glycol, olive oil, ethanol, POLYSOLBATE 80 (registered trademark) and the like.

Injections may comprise additional other than inert diluents: e.g. preserving agents, wetting agents, emulsifying agents, dispersing agents, stabilizing agents (lactose etc.), assisting agents such as for dissolving (glutamic acid, aspartic acid etc.). They may be sterilized, for example, by filtration through a bacteria-retaining filter, by incorporation of sterilizing agents in the compositions or by irradiation. They also may be manufactured in the form of sterile solid compositions, for example, by freeze-drying, and which can be dissolved in sterile water or some other sterile diluents for injection immediately before use.

Other compositions for administration include liquids for external use, and endermic liniments (ointment, etc.), suppositories and pessaries which comprise one or more of the active compound(s) and may be prepared by known methods It is intended that the foregoing description be only illustrative of the present invention and that the present invention be limited only by the hereinafter appended claims.

We claim:

1. An aryl aliphatic acid or derivatives thereof of the formula

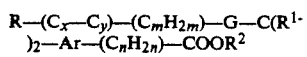

wherein m and n are an integer between 1 and 6;
wherein the pattern of substitution in the aryl ring (Ar) is selected from the group consisting of orth-, meta- and para-,
wherein G is selected from the group consisting of O and S;
wherein ($C_x$–$C_y$) is selected from the group consisting of ethynylene, cis-vinylene, trans-vinylene, propadienylene, and arylene;
wherein R is selected from the group consisting of heptyl, octyl, nonyl, decyl, undecyl, dodecyl, tridecyl, tetradecyl, phenyl, benzyl, phenethyl, phenylpropyl, phenylbutyl, and phenylpentyl and isomers thereof;
wherein each $R^1$ is independently H or lower alkyl or a combination thereof;
wherein $R^2$ is H, a salt, lower alkyl or aralkyl.

2. The compound of claim 1 wherein ($C_nH_{2n}$) and ($C_mH_{2m}$) are selected from the group consisting of methylene, ethylene, trimethylene, tetramethylene, pentamethylene, hexamethylene, and isomers thereof.

3. The compound of claim 1 wherein Ar is phenylene.

4. The compound of claim 1 wherein the salts are selected from the group consisting of alkali metal, alkaline earth metal salts, ammonium salts, and pharmaceutically acceptable organic amine salts.

5. The compound of claim 4 wherein the salts are selected from the group consisting of tetramethylammonium, trimethylamine, dimethylamine, cyclopentylamine, benzylamine, phenethylamine, piperidine, monoethanolamine, diethanolamine, tris(hydroxymethyl)amine, lysine, arginine and N-methyl-D-glucamine salts.

6. The compound of claim 1 which is cis-3-(4-(2-tridecenyloxymethyl)-phenyl) propanoic acid.

7. The compound of claim 1 which is 3-(3-(3-nonynloxymethyl)phenyl) propanoic acid.

8. The compound of claim 1 which is 3-(4-(1,1-dimethyl-2-tridecynyloxy)methyl)phenyl)propanoic acid.

9. The compound of claim which is 3-(3-(2-undecynyloxymethyl)phenyl)propanoic acid.

10. The compound of claim 1 which is 3-(3-(2-tridecynyloxymethyl)phenyl)propanoic acid.

11. The compound of claim 1 which is (S)-3-(4-(2,3-tetradecadienyloxymethyl)phenyl)propanoic acid.

12. The compound of claim 1 which is (R)-3-(4-(2,3-tetradecadienyloxymethyl)phenyl)propanoic acid.

13. The compound of claim 1 which is 3-(3-(2-undecynylthiomethyl)phenyl)propanoic Acid.

14. The compound of claim 1 which is 3-(4-(2-tridecynloxymethyl)phenyl)propanoic acid.

15. The compound of claim 1 which is 3-(3-(3-phenyl-2-propynyloxymethyl)phenyl)propanoic acid.

16. The compound of claim 1 which is trans-3-(4-(2-tridecenyloxymethyl)phenyl)propanoic acid.

17. The compound of claim 1 which is 3-(4-(2-nonynyloxymethyl)phenyl)propanoic acid.

18. The compound of claim 1 which is 3-(4-(tridecyloxymethyl)phenyl)propanoic acid.

19. The compound of claim 1 which is 3-(4-(2-undecynyloxymethyl)phenyl)propanoic acid.

20. The compound of claim 1 which is 3-(4-(2-heptadecynyloxymethyl)phenyl)propanoic acid.

21. The compound of claim 1 which is 3-(4-(2-pentadecynyloxymethyl)phenyl)propanoic acid.

22. The compound of claim 1 which is 3-(3-(2-decynyloxymethyl)phenyl)propanoic acid.

23. The compound of claim 1 which is 3-(3-(2-nonynyloxymethyl)phenyl)propanoic acid.

24. The compound of claim 1 which is 3-(4-(7-phenyl-2-heptynyloxymethyl)phenyl)propanoic acid.

25. The compound of claim 1 which is 3-(4-(4-decylphenylmethyl)oxymethyl)phenyl)propanoic acid.

26. The compound of claim 1 which is 3-(3-(2-tridecynyloxymethyl)phenyl)butyric acid.

27. The compound of claim 1 which is cis-3-(3-(2-undecenyloxymethyl)phenyl)propanoic acid.

28. The compound of claim 1 which is 3-(3-(2-tridecyloxymethyl)phenyl)propanoic acid.

29. The compound of claim 1 which is 3-(2-(2-tridecynyloxymethyl)phenyl)propanoic acid.

30. The compound of claim 1 which is trans-3-(3-(2-tridecenyloxymethyl)phenyl)propanoic acid.

31. The compound of claim 1 which is 2,2-dimethyl-3-(4-((2-tridecynyloxy)methyl]phenyl)propanoic acid.

32. The compound of claim 1 which is 3-methyl-3-]4-(2-tridecynyloxy)methyl)phenyl)propanoic acid.

33. The compound of claim 1 which is 3-(4-((1-methyl-2-tridecynyloxy)methyl)phenyl)propanoic acid.

34. The compound of claim 1 which is (R)-(+)-3-(4-((1-methyl-2-tridecynyloxy)methyl)phenyl)propanoic acid.

35. The compound of claim 1 which is (S)-(−)-3-(4-((1-methyl-2-tridcynyloxy)methyl)phenyl)propanoic acid.

36. A method for inhibiting 12-lipoxygenase in vitro which comprises exposing the 12-lipoxygenase in vitro to an effective amount of an aryl aliphatic acid of the formula:

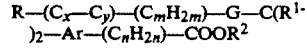

wherein m and n are an integer between 1 and 6;
wherein the pattern of substitution in the aryl ring (Ar) is selected from the group consisting of ortho-, meta- and para-,
wherein G is selected from the group consisting of O and S;
wherein ($C_x$–$C_y$) is selected from the group consisting of ethynylene, cis-vinylene, trans-vinylene, propadienylene, and arylene;
wherein R is selected from the group consisting of heptyl, octyl, nonyl, decyl, undecyl, dodecyl, tridecyl, tetradecyl, phenyl, benzyl, phenethyl, phenylpropyl, phenylbutyl, and phenylpentyl and isomers thereof;

wherein each $R^1$ is independently H or lower alkyl or a combination thereof;

wherein $R^2$ is H, a salt, lower alkyl or aralkyl.

37. The method of claim 36 wherein ($C_nH_{2n}$) and ($C_mH_{2m}$) are selected from the group consisting of methylene, ethylene, trimethylene, tetramethylene, pentamethylene, hexamethylene, and isomers thereof.

38. The method of claim 36 wherein Ar is phenylene.

39. The method of claim 36 wherein the salts are selected from the group consisting of alkali metal, alkaline earth metal salts, ammonium salts, and pharmaceutically acceptable organic amine salts.

40. The method of claim 36 wherein the salts are selected from the group consisting of tetramethylammonium, trimethylamine, dimethylamine, cyclopentylamine, benzylamine, phenethylamine, piperidine, monoethanolamine, diethanolamine, tris(hydroxymethyl)amine, lysine, arginine and N-methyl-D-glucamine salts.

41. The method of claim 36 wherein the said is cis-3-(4-(2-tridecenyloxymethyl)-phenyl) propanoic acid.

42. The method of claim 36 wherein the said is 3-(3-(3-thyl)phenyl) propanoic acid.

43. The method of claim 36 wherein the said is 3-(4-(1,1-dimethyl-2-tridecynyloxy)methyl)phenyl)-propanoic acid.

44. The method of claim 36 wherein the said is 3-(3-(2-undecynyloxymethyl)phenyl)propanoic acid.

45. The method of claim 36 wherein the said is 3-(3-(2-tridecynyloxymethyl)phenyl)propanoic acid 46. The method of claim 36 wherein the said is (S)-3-(4-(2,3-tetradecadienyloxymethyl)phenyl)propanoic acid.

47. The method of claim 36 wherein the said is (R)-3-(4-(2,3-tetradecadienyloxymethyl)phenyl)propanoic acid.

48. The method of claim 36 wherein the said is 3-(3-(2-undecynylthiomethyl)phenyl)propanoic Acid.

49. The method of claim 36 wherein the said is 3-(4-(2-tridecynloxymethyl)phenyl)propanoic acid.

50. The method of claim 36 wherein the said is 3-(3-(3-phenyl-2-propynyloxymethyl)phenyl)propanoic acid.

51. The method of claim 36 wherein the said is trans-3-(4-(2-tridecenyloxymethyl)phenyl)propanoic acid.

52. The method of claim 36 wherein the said is 3-(4-(2-nonynyloxymethyl)phenyl)propanoic acid.

53. The method of claim 36 wherein the said is 3-(4-(tridecyloxymethyl)phenyl)propanoic acid.

54. The method of claim 36 wherein the said is 3-(4-(2-undecynyloxymethyl)phenyl)propanoic acid.

55. The method of claim 36 wherein the said is 3-(4-(2-heptadecynyloxymethyl)phenyl)propanoic acid.

56. The method of claim 36 wherein the said is 3-(4-(2-pentadecynyloxymethyl)phenyl)propanoic acid.

57. The method of claim 36 wherein the said is 3-(3-(2-decynyloxymethyl)phenyl)propanoic acid.

58. The method of claim 36 wherein the said is 3-(3-(2-nonynyloxymethyl)phenyl)propanoic acid.

59. The method of claim 36 wherein the said is 3-(4-(7-phenyl-2-heptynyloxymethyl)phenyl)propanoic acid.

60. The method of claim 36 wherein the said is 3-(4-(4-decylphenylmethyl)oxymethyl)phenyl)propanoic acid.

61. The method of claim 36 wherein the said is 3-(3-(2-tridecynyloxymethyl)phenyl)butyric acid.

62. The method of claim 36 wherein the said is cis-3-(3-(2-undecynyloxymethyl)phenyl)propanoic acid.

63. The method of claim 36 wherein the said is 3-(3-(2-tridecyloxymethyl)phenyl)propanoic acid.

64. The method of claim 36 wherein the said is 3-(2-(2-tridecynyloxymethyl)phenyl)propanoic acid.

65. The method of claim 36 wherein the said is trans-3-(3-(2-tridecenyloxymethyl)phenyl)propanoic acid.

66. The method of claim 36 wherein the said is 2,2-dimethyl-3-(4-((2-tridecynyloxy)methyl]phenyl)-propanoic acid.

67. The method of claim 36 wherein the said is 3-methyl-3-[4-(2-tridecynyloxy)methyl)phenyl)propanoic acid.

68. The method of claim 36 wherein the said is 3-(4-((1-methyl-2-tridecynyloxy)methyl)phenyl)propanoic acid.

69. The method of claim 36 wherein the said is (R)-(+)-3-(4-((1-methyl-2-tridecynyloxy)methyl)-phenyl)propanoic acid.

70. The method of claim 36 wherein the said is (S)-(−)-3-(4-((1-methyl-2-tridecynyloxy)methyl),phenyl)-propanoic acid.

* * * * *

UNITED STATES PATENT AND TRADEMARK OFFICE
CERTIFICATE OF CORRECTION

PATENT NO. : 5,238,832

DATED : August 24, 1993

INVENTOR(S) : Carl R. Johnson, Gilles Gorins, Kenneth V. Honn, and Lawrence J. Marnett It is certified that error appears in the above—identified patent and that said Letters Patent is hereby corrected as shown below:

Column 1, line 14, "$(C_mH_{2m})$-B-" should read --$(C_mH_{2m})$-G- --.

Column 1, line 27, "5(X)-" should be --5(S)- --.

Column 1, line 28, "lipoxygenae" should be --lipoxygenase--.

Column 1, line 29, "6(E), 8(Z)-14(Z)-" should be --6(E), 8(Z), 11(Z)-14(Z)- --.

Column 6, line 44, the colon ":" should be deleted before "H".

Column 7, line 41, "Commun. 157 (1981))" should read --Commun. 11, 157 (1981))--.

Column 7, line 63, a bracket "]" should be inserted after "oxymethyl".

Column 9, line 29, "Of" should be --of-- and "tridecen" should be --tridecenyl--.

Column 9, line 68, "239" should be --23.9--.

Column 10, line 1, "J 6.6" should read --J = 6.6 --.

UNITED STATES PATENT AND TRADEMARK OFFICE
CERTIFICATE OF CORRECTION

PATENT NO. : 5,238,832
DATED : August 24, 1993
INVENTOR(S) : Carl R. Johnson, Gilles Gorins, Kenneth V. Honn, and Lawrence J. Marnett It is certified that error appears in the above—identified patent and that said Letters Patent is hereby corrected as shown below:

Column 10, line 13, "-4-(z-tridecenyoxymethyl--  should read -- -4-(2-tridecenyloxymethyl --.

Column 10, line 14, "Ph:P" should read --Ph$_3$P--.

Column 10, line 44, "3-[4-(z-Tri" should read -- 3-[4-(2-Tri --.

Column 11, line 42, "(250 mg, mmol)" should read --250 mg, 1 mmol)--.

Column 12, line 14, "i N" should read --1 N--.

Column 12, line 41, "3-[4-3=Nonynloxymethyl" should read --3-[4-3-Nonynloxymethyl--.

Column 13, line 1, "[tert=Butyldiphen. ." should read --[tert-Butydiphen. . --

Column 13, line 2, "(S)-i-" should read --(S)-1- --.

Column 13, line 30, "warm t" should read --warm to--.

Column 13, line 48, "129" should read --1.29--.

Column 13, line 61, --1-- should be inserted before "hour".

UNITED STATES PATENT AND TRADEMARK OFFICE
CERTIFICATE OF CORRECTION

PATENT NO. : 5,238,832  Page 3 of 13
DATED : August 24, 1993
INVENTOR(S) : Carl R. Johnson, Gilles Gorins, Kenneth V. Honn and Lawrence J. Marnett It is certified that error appears in the above—identified patent and that said Letters Patent is hereby corrected as shown below:

Column 13, line 67, "(3) 30 (0.33 g" should read --(3) (0.33 g--.

Column 14, line 46, "p-toluenesufonic" should read --p-toluenesulfonic--.

Column 15, line 61, "MgSO$_2$)" should read --MgSO$_4$)--.

Column 15, line 65, "130" should read --1.30--.

Column 16, line 9, "1;-nonyne" should read --1-nonyne--.

Column 16, line 14, "(361 mg, 2" should read --(361 mg, 1--.

Column 16, line 29, "136,38" should read --136.38--.

Column 16, line 41, "CH:CN" should read --CH$_3$CN--.

Column 16, line 44, "NaHCO3" should read --NaHCO$_3$--.

Column 16, line 53, "is a" should read --as a--.

UNITED STATES PATENT AND TRADEMARK OFFICE
CERTIFICATE OF CORRECTION

PATENT NO. : 5,238,832
DATED : August 24, 1993
INVENTOR(S) : Carl R. Johnson, Gilles Gorins, Kenneth V. Honn and Lawrence J. Marnett It is certified that error appears in the above—identified patent and that said Letters Patent is hereby corrected as shown below:

Column 16, line 60, the formula " 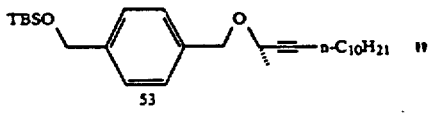 "

should read as follows: --  --.

Column 17, line 45, the formula " 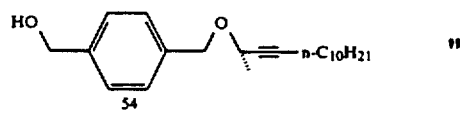 "

should read as follows: --  --.

Column 17, line 48, "Dimethyl-2=" should read -- Dimethyl-2- --.

Column 17, line 59, "12687" should read --126.87--.

UNITED STATES PATENT AND TRADEMARK OFFICE
CERTIFICATE OF CORRECTION

PATENT NO. : 5,238,832
DATED : August 24, 1993
INVENTOR(S) : Carl R. Johnson, Gilles Gorins, Kenneth V. Honn and Lawrence J. Marnett It is certified that error appears in the above—identified patent and that said Letters Patent is hereby corrected as shown below:

Column 17, line 65, the formula "  "

should read as follows: -- 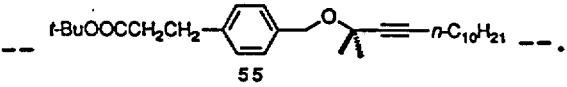 --.

Column 18, line 5, "(s, 6 3H); $^{13}$C" should read --(s, 6 H), 1.44 (s, 9 H), 1.28 (m, 16 H), 0.89 (t, J = 6.9 Hz, 3 H); $^{13}$C--.

Column 18, line 12, the formula " 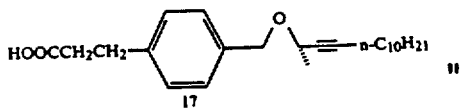 "

should read as follows: -- 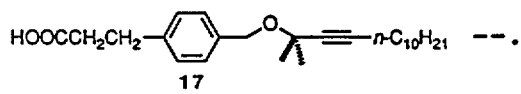 --.

Column 18, line 29, "3 H); $^{13}$; C NMR" should read --3 H); $^{13}$C NMR --.

Column 19, line 25, "3-[3=(2-" should read --3-[3-(2- --.

UNITED STATES PATENT AND TRADEMARK OFFICE
CERTIFICATE OF CORRECTION

PATENT NO. : 5,238,832

DATED : August 24, 1993

INVENTOR(S) : Carl R. Johnson, Gilles Gorins, Kenneth V. Honn and Lawrence J. Marnett It is certified that error appears in the above-identified patent and that said Letters Patent is hereby corrected as shown below:

Column 19, line 26, "Acid (lo)" should read --Acid (10)--.

Column 20, line 15, "J = 6.9 Hz, J: = 2.1 Hz" should read --$J_1$ = 6.9 Hz, $J_2$ = 2.1 Hz --.

Column 20, line 48, "J: = 2.7 Hz" should read --$J_2$ = 2.7 Hz--.

Column 21, line 31, "CHC$_3$l)" should read --CHCl$_3$) --.

Column 21, line 36, "2.7 Hz, H)" should read --2.7 Hz, 2H)--.

Column 22, line 63, "(z4)" should read --(24)--.

Column 23, line 28, "Acid (3s)" should read --Acid (38)--.

Column 23, line 45, "J, = 5.3" should read --$J_1$ = 15.3--

Column 26, line 39, "28.19, 26.33" should read --28.18, 26.33--.

Column 27, line 27, "phenyl-" should read -- phenyl] --.

Column 29, line 26, "(58):" should read --(88):--.

Column 29, line 59, "Acid (2s)" should read --Acid (28)--

UNITED STATES PATENT AND TRADEMARK OFFICE
CERTIFICATE OF CORRECTION

PATENT NO. : 5,238,832
DATED : August 24, 1993
INVENTOR(S) : Carl R. Johnson, Gilles Gorins, Kenneth V. Honn and Lawrence J. Marnett It is certified that error appears in the above—identified patent and that said Letters Patent is hereby corrected as shown below:

Column 30, line 44, "3-[3-(z-" should read --3-[3-(2- --.

Column 30, line 62, "(z-Nonyn" should read --(2-Nonyn--.

Column 31, line 29, "s, I 1H)," should read --(s, 1 H),--.

Column 35, line 12, "H), 5.62", should read --4 H), 5.62--

Column 35, line 44, "[3-(2=Undec" should read --[3-(2-Undec--.

Column 36, line 29, "$J_2$ - 2.1" should read --$J_2$ = 2.1--.

Column 36, line 60, "3-[2-2=Tri" should read --3-[2-2-Tri--.

Column 38, line 15, "[3-(2=Tridec" should read --[3-(2-Tridec--.

Column 38, line 18, "$J_1$=5.3 Hz" should read --$J_1$=15.3 Hz--.

Column 38, line 51, "3-(2=Tridec" should read --3-(2-Tridec--

Column 36, line 29, "J=" should read --$J_1$ --

UNITED STATES PATENT AND TRADEMARK OFFICE
CERTIFICATE OF CORRECTION

PATENT NO. : 5,238,832
DATED : August 24, 1993
INVENTOR(S) : Carl R. Johnson, Gilles Gorins, Kenneth V. Honn and Lawrence J. Marnett It is certified that error appears in the above—identified patent and that said Letters Patent is hereby corrected as shown below:

Column 39, line 45, the formula "  "

should be -- 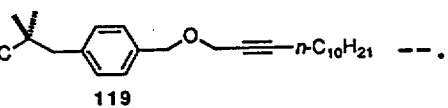 --.

Column 39, line 62, the formula " 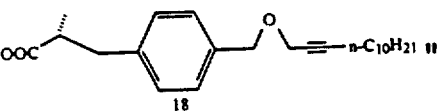 "

should be -- 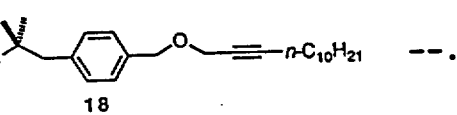 --.

UNITED STATES PATENT AND TRADEMARK OFFICE
CERTIFICATE OF CORRECTION

PATENT NO. : 5,238,832
DATED : August 24, 1993
INVENTOR(S) : Carl R. Johnson, Gilles Gorins, Kenneth V. Honn and Lawrence J. Marnett It is certified that error appears in the above—identified patent and that said Letters Patent is hereby corrected as shown below:

Column 40, line 62, the formula "  "

should be -- 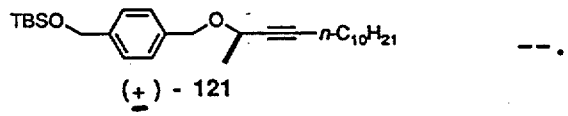 --.

Column 41, line 35, the formula " 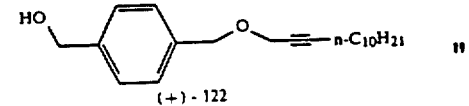 "

should be -- 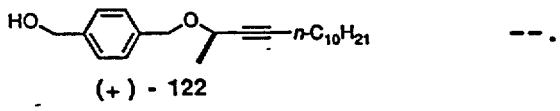 --.

Column 41, line 40, "A]) spectral data Were identical" should read --All spectral data were identical--.

Column 41, line 65, "i.54" should read --1.54--.

Column 41, line 66, "i.28 (s, i4 H)" should read --1.28 (s, 14 H)--.

UNITED STATES PATENT AND TRADEMARK OFFICE
CERTIFICATE OF CORRECTION

PATENT NO. : 5,238,832
DATED : August 24, 1993
INVENTOR(S) : Carl R. Johnson, Gilles Gorins, Kenneth V. Honn and Lawrence J. Marnett It is certified that error appears in the above—identified patent and that said Letters Patent is hereby corrected as shown below:

Column 42, line 5, the formula "  "

should be -- 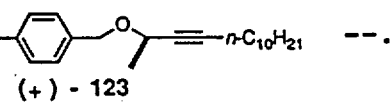 --.

Column 42, line 22, "(C 11.7," should read --(C 1.17, --.

Column 42, line 30, "Methyl-2=tridec" should read -- Methyl-2-tridec--.

Column 42, line 45, the formula " 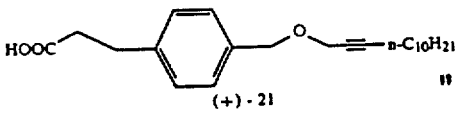 "

should be -- 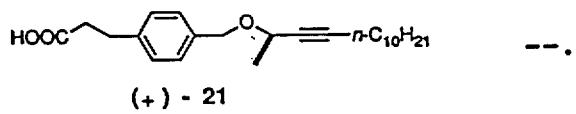 --.

Column 42, line 49, "[(1=Methyl", should read -- [C1-Methyl --.

UNITED STATES PATENT AND TRADEMARK OFFICE
CERTIFICATE OF CORRECTION

PATENT NO. : 5,238,832

DATED : August 24, 1993

INVENTOR(S) : Carl R. Johnson, Gilles Gorins, Kenneth V. Honn and Lawrence J. Marnett It is certified that error appears in the above-identified patent and that said Letters Patent is hereby corrected as shown below:

Column 45, line 22 (Claim 1), "orth-" should read --ortho- --.

Column 45, line 59 (Claim 9), after "Claim", --1-- should be inserted.

Column 46, line 45 (Claim 35), "tridcynyloxy" should be --tridecynyloxy--.

Column 47, line 20 (Claim 41), "said" should be --acid--.

Column 47, line 22 (Claim 42), "said" should be --acid--.

Column 47, line 23 (Claim 42), "(3-thyl)phenyl" should read --(3-nonynloxymethyl)phenyl--.

Column 47, line 24 (Claim 43), "said" should be --acid--.

Column 47, line 27 (Claim 44), "said" should be --acid--.

Column 47, line 29 (Claim 45), "said" should be --acid--.

Column 47, line 31 (Claim 46), "said" should be --acid--.

Column 47, line 34 (Claim 47), "said" should be --acid--.

Column 47, line 37 (Claim 48), "said" should be --acid--.

UNITED STATES PATENT AND TRADEMARK OFFICE
CERTIFICATE OF CORRECTION

PATENT NO. : 5,238,832
DATED : August 24, 1993
INVENTOR(S) : Carl R. Johnson, Gilles Gorins, Kenneth V. Honn and Lawrence J. Marnett It is certified that error appears in the above—identified patent and that said Letters Patent is hereby corrected as shown below:

Column 47, line 40 (Claim 49), "said" should be --acid--.

Column 47, line 42 (Claim 50), "said" should be --acid--.

Column 47, line 45 (Claim 51), "said" should be --acid--.

Column 48, line 1 (Claim 52), "said" should be --acid--.

Column 48, line 3 (Claim 53), "said" should be --acid--.

Column 48, line 5 (Claim 54), "said" should be --acid--.

Column 48, line 7 (Claim 55), "said" should be --acid--.

Column 48, line 9 (Claim 56), "said" should be --acid--.

Column 48, line 11 (Claim 57), "said" should be --acid--.

Column 48, line 13 (Claim 58), "said" should be --acid--.

Column 48, line 15 (Claim 59), "said" should be --acid--.

Column 48, line 18 (Claim 60), "said" should be --acid--.

Column 48, line 21 (Claim 61), "said" should be --acid--.

Column 48, line 23 (Claim 62), "said" should be --acid--.

UNITED STATES PATENT AND TRADEMARK OFFICE
CERTIFICATE OF CORRECTION

PATENT NO. : 5,238,832
DATED : August 24, 1993
INVENTOR(S) : Carl R. Johnson, Gilles Gorins, Kenneth V. Honn and Lawrence J. Marnett It is certified that error appears in the above—identified patent and that said Letters Patent is hereby corrected as shown below:

Column 48, line 25 (Claim 63), "said" should be --acid--.

Column 48, line 27 (Claim 64), "said" should be --acid--.

Column 48, line 29 (Claim 65), "said" should be --acid--.

Column 48, line 31 (Claim 66), "said" should be --acid--.

Column 48, line 34 (Claim 67), "said" should be --acid--.

Column 48, line 37 (Claim 68), "said" should be --acid--.

Column 48, line 40 (Claim 69), "said" should be --acid--.

Column 48, line 43 (Claim 70), "said" should be --acid--.

Signed and Sealed this

Twenty-fourth Day of May, 1994

Attest:

BRUCE LEHMAN

Attesting Officer        Commissioner of Patents and Trademarks